(12) United States Patent
Brenner et al.

(10) Patent No.: US 9,863,937 B2
(45) Date of Patent: Jan. 9, 2018

(54) FLUORESCENT MOLECULAR ROTORS

(71) Applicant: Agency for Science, Technology and Research, Singapore (SG)

(72) Inventors: Sydney Brenner, Singapore (SG); Yin Nah Teo, Singapore (SG); Farid Ghadessy, Singapore (SG); Leng Peng Walter Goh, Singapore (SG); Min Yen Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 82 days.

(21) Appl. No.: 14/431,723

(22) PCT Filed: Sep. 26, 2013

(86) PCT No.: PCT/SG2013/000420
§ 371 (c)(1),
(2) Date: Mar. 26, 2015

(87) PCT Pub. No.: WO2014/051521
PCT Pub. Date: Apr. 3, 2014

(65) Prior Publication Data
US 2016/0195519 A1 Jul. 7, 2016

(30) Foreign Application Priority Data

Sep. 26, 2012 (SG) ............................. 201207166-8
Aug. 2, 2013 (SG) ............................. 201305898-7

(51) Int. Cl.
*C07C 255/41* (2006.01)
*G01N 33/542* (2006.01)
(Continued)

(52) U.S. Cl.
CPC ......... *G01N 33/542* (2013.01); *C07C 255/41* (2013.01); *C07D 219/08* (2013.01);
(Continued)

(58) Field of Classification Search
CPC . C07C 255/41; C07C 2603/50; C07D 519/00; C07D 495/04; C07D 455/04; C07D 401/14; C07D 219/08; C07D 417/06; G01N 33/542; G01N 33/582
See application file for complete search history.

(56) References Cited

FOREIGN PATENT DOCUMENTS

| JP | H07287405 | 10/1995 |
|---|---|---|
| WO | WO-2007/041241 | 4/2007 |
| WO | WO-2014/051521 | 4/2014 |

OTHER PUBLICATIONS

Dumat et al. Vinyl-triphenylamine dyes, a new family of switchable fluorescent probes for targeted two-photon cellular imaging: from DNA to protein labeling. Org. Biomol. Chem. 2012, vol. 10, pp. 6054-6061.*

(Continued)

*Primary Examiner* — Shafiqul Haq
(74) *Attorney, Agent, or Firm* — Schwegman Lundberg & Woessner, P.A.

(57) ABSTRACT

The present invention relates to methods and compositions for detecting an interaction between a protein and a ligand, comprising: (i) binding at least one fluorescent molecular rotor to said ligand or protein; and (ii) detecting a change in fluorescence emitted by said fluorescent molecular rotor after contact of the bound fluorescent molecular rotor with the other of said ligand or protein, thereby detecting an interaction between the ligand and the protein, wherein the fluorescent molecular rotor comprises: a rotating ?-bond; an electron-donating moiety; an electron-accepting moiety; and a ?-conjugated linker.

1 Claim, 32 Drawing Sheets

(51) Int. Cl.
*C07D 219/08* (2006.01)
*C07D 401/14* (2006.01)
*C07D 417/06* (2006.01)
*C07D 455/04* (2006.01)
*C07D 495/04* (2006.01)
*C07D 519/00* (2006.01)
*G01N 33/58* (2006.01)

(52) U.S. Cl.
CPC ......... *C07D 401/14* (2013.01); *C07D 417/06* (2013.01); *C07D 455/04* (2013.01); *C07D 495/04* (2013.01); *C07D 519/00* (2013.01); *G01N 33/582* (2013.01); *C07C 2603/50* (2017.05)

(56) References Cited

OTHER PUBLICATIONS

"International Application No. PCT/SG2013/000420, International Preliminary Report on Patentability dated Jan. 13, 2015", (Jan. 13, 2015), 112 pgs.

"International Application No. PCT/SG2013/000420, International Search Report and Written Opinion dated Jan. 15, 2014", (Jan. 15, 2014), 15 pgs.

Tsai, Yu-Lin, et al., "Effect of different electronic properties on 9-aryl-substituted BMVC derivatives for new fluorescence probes", Journal of Luminescence 127 (2007) 41-47, (Mar. 6, 2007), 41-47.

* cited by examiner

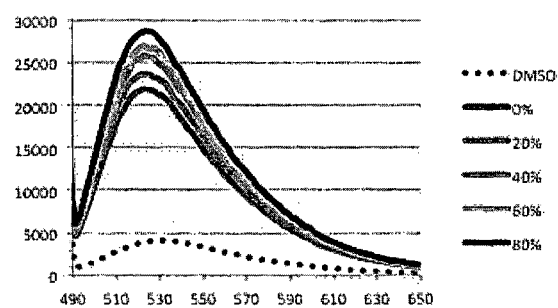

| Peptide ID | Aminoacid sequence | $K_d^\#$ |
|---|---|---|
| JP1 | MPRFMDYWEGLSK | 18.83 ± 5.03 |
| JP2 | MPRFMDYWEGLNK | 239.81 ± 53.79 |

\# Without lysine residue at C-terminus

JP1-R

JP2-R

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: A synthetic polypeptide

<400> SEQUENCE: 1

Met Pro Arg Phe Met Asp Tyr Trp Glu Gly Leu Ser Lys
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: A synthetic polypeptide

<400> SEQUENCE: 2

Met Pro Arg Phe Met Asp Tyr Trp Glu Gly Leu Asn Lys
 1               5                  10
```

FLUORESCENT MOLECULAR ROTORS

PRIORITY CLAIM TO RELATED APPLICATIONS

This application is a U.S. national stage application filed under 35 U.S.C. §371 from International Application Serial No. PCT/SG2013/000420, which was filed Sep. 26, 2013, and published as WO 2014/051521 on Apr. 3, 2014, and which claims priority to Singapore Application No. 201207166-8, filed Sep. 26, 2012, and to Singapore Application No. 201305898-7, filed Aug. 2, 2013, which applications and publication are incorporated by reference as if reproduced herein and made a part hereof in their entirety, and the benefit of priority of each of which is claimed herein.

TECHNICAL FIELD

The present invention generally relates to fluorescent molecular rotors and compositions comprising the same. The present invention also relates to the use of fluorescent molecular rotors in detecting protein-ligand interactions.

BACKGROUND

Fluorescent Molecular Rotors

Molecular rotors are a collective group of fluorescent compounds that possess the ability to undergo twisted intramolecular charge transfer (TICT) and are typically used as viscosity sensor probes. They typically consist of three parts: an electron-donating unit, an electron-accepting unit and a π-conjugated linking moiety which allows electron transfer to occur in the planar conformation. However, electrostatic forces upon irradiation result in the molecule adopting a twisted conformation around the σ-bond in the linker region. This non-planar, twisted conformation has a lower excited state energy and thus is associated with either a red-shifted fluorescence emission or can undergo a non-radiative torsional relaxation pathway, depending on the molecular structure of the rotor. If the intramolecular rotation is hindered, the non-radiative pathway is prevented and the molecule adopts a planar configuration, thus restoring fluorescence.

Protein Labelling Techniques

Progress in understanding complex biological systems depends on characterizing the underlying interactions of biomolecules, in particular proteins. The interaction of proteins with ligands, such as peptides, DNA or small molecules, offers biologists powerful tools for visualizing protein dynamics.

For example, the investigation of protein-peptide interactions. The p53 tumour suppressor protein is the key determinant of cell fate. It is mutated in 50% of all cancers. It is primarily regulated by the ubiquitin ligase MDM2 which targets it for proteosomal degradation. The interaction between MDM2 and p53 has been mapped to the N-terminal of p53 (residues 18-26) and the N-terminal domain of MDM2 (residues 1-110). In 50% of cancers with wild-type p53, inhibition of MDM2 leading to increased p53 levels and cell death represents an attractive therapeutic modality. Several compounds that bind to the N-terminal domain of MDM2 and abrogate p53 binding have shown promise in preclinical development. Both the further development of these pre-existing compounds and high-throughput screens for novel compounds will benefit greatly from robust, facile and sensitive methods enabling detection of the p53-MDM2 interaction.

Additionally, the interactions of proteins with DNA are essential cellular processes. Compromised protein-DNA interactions can give rise to severe disease phenotypes, notably cancer. There exists therefore, a requirement for robust assays enabling both fundamental understanding of interactions at the molecular level, and high-throughput screening of compound libraries for drugs capable of "reactivating" a mutant protein with diminished or absent DNA-binding.

One way to determine protein-DNA binding is through electrophoretic mobility shift assay (EMSA). EMSA identifies protein-DNA binding by the shift in the electrophoretic migration of DNA through a gel when it is bound by a protein. Another way is through and DNA footprinting. DNA footprinting identifies protein-DNA complexes through resistance of DNA to nucleolytic degradation when it is bound by a protein. However, these methods are technically demanding, semi-quantitative, not-easily reproduced, low-throughput and typically require the use of radioisotopes for optimal results.

Another way is based on the ELISA format involving the use of biotinylated DNA to capture protein-DNA (p53 protein bound to target DNA) complexes on streptavidin plates. The complexes are subsequently detected through the use of an anti-p53 monoclonal antibody that does do not disrupt the complex. A variation of this technique has also been described using microspheres and flow analysis. Other techniques include surface plasmon resonance (SPR), and fluorescence anisotropy. Whilst powerful and insightful, these methods require expensive instrumentation, are laborious, and are not suited for high-throughput applications.

One way of detecting protein-DNA binding occurs through a combination of immunoprecipitation and real-time PCR. However, this method is not optimal for high-throughput screening as it requires multiple washing steps and real-time PCR which can be costly.

There is therefore a need to provide a quantitative, label-free, homogenous, non-radioactive, reproducible and high-throughput method to measure protein-ligand binding.

There is also a need to provide a high-throughput screening method for measuring protein-ligand interactions which is non-laborious and does not require the use of expensive instrumentation.

There is also a need to provide a high-throughput screening method for measuring protein-ligand interactions which lessens the requirement for multiple washing steps.

Therefore, there is a need for methods for detecting interactions between a protein and ligands that ameliorate the above problems. The present invention seeks to fulfill these needs and provides further related advantages.

SUMMARY

According to a first aspect, there is provided a method for detecting an interaction between a protein and a ligand, comprising:
(i) binding at least one fluorescent molecular rotor to said ligand or protein; and
(ii) detecting a change in fluorescence emitted by said fluorescent molecular rotor after contact of the bound fluorescent molecular rotor with the other of said ligand or protein, thereby detecting an interaction between the ligand and the protein.
with the proviso that the fluorescent molecular rotor is not a compound selected from the following table:

| | Structure | R groups |
|---|---|---|
| 1 | 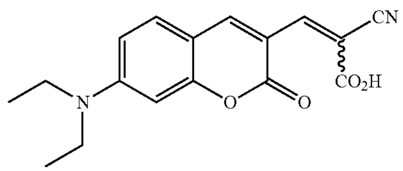 [SMILES: CCN(CC)c1ccc2cc(C=C(C#N)C(=O)O)c(=O)oc2c1] | |
| 2 | 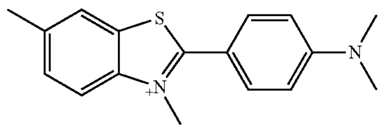 | |
| 3 | 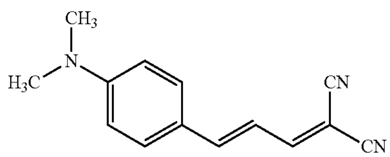 [SMILES: CN(C)c1ccc(/C=C/C=C(C#N)C#N)cc1] | |
| 4 | 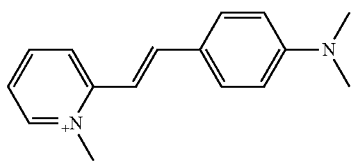 [SMILES: CN(C)c1ccc(/C=C/c2cccc[n+]2C)cc1] | |
| 5 | 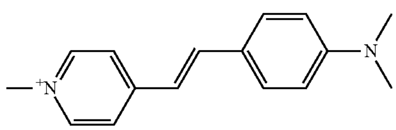 | |
| 6 | 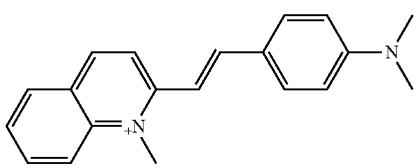 [SMILES: CN(C)c1ccc(/C=C/c2ccc3ccccc3[n+]2C)cc1] | |
| 7 | 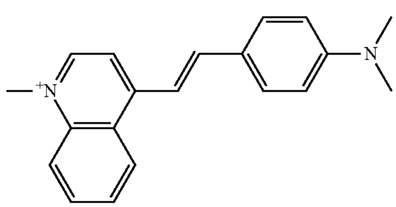 | |
| 8 | 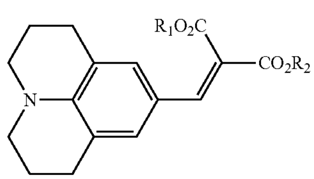 | |
| 9 | 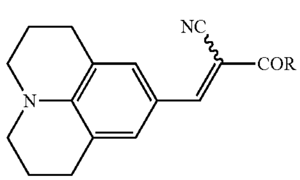 | R = OH, OEt, $NH_2$ |

-continued

| | Structure | R groups |
|---|---|---|
| 10 | 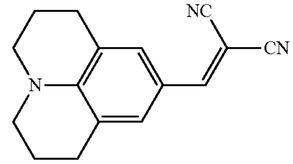 [SMILES: N#CC(C#N)=Cc1cc2c3c(c1)CCCN3CCC2] | |
| 11 | 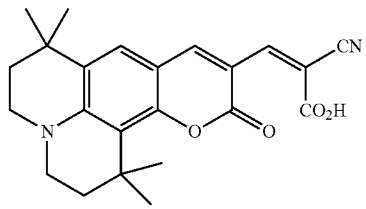 [SMILES: CC1(C)CCN2CCC(C)(C)c3c2c1cc1cc(/C=C(/C#N)C(=O)O)c(=O)oc31] | |
| 12 | 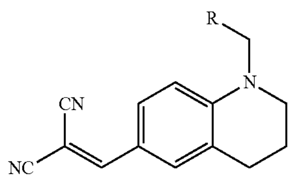 | R = COOH, CO₂Et, CH₂OH, CH₂OAc, CH₂Cl |
| 13 | 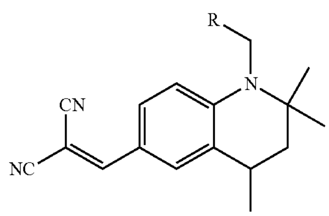 | R = CO₂CO₂Ph |
| 14 | 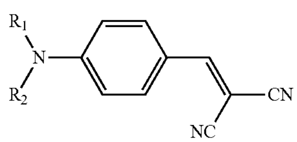 | $R_1, R_2 = CH_3$ |
| 15 | 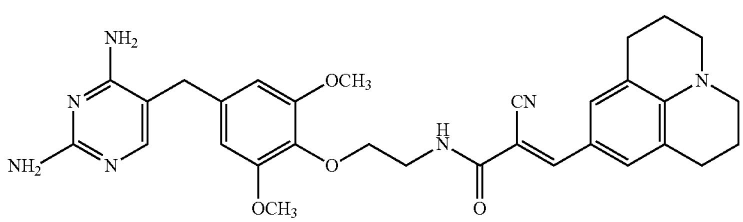 [SMILES: COc1cc(Cc2cnc(N)nc2N)cc(OC)c1OCCNC(=O)/C(C#N)=C/c1cc2c3c(c1)CCCN3CCC2] | |
| 16 | 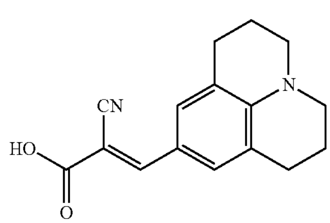 [SMILES: N#C/C(=C\c1cc2c3c(c1)CCCN3CCC2)C(=O)O] | |
| 17 | 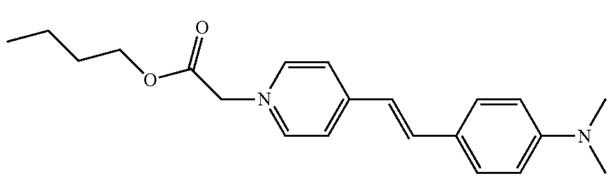 | |

In a second aspect, there is provided a method for detecting an interaction between a protein and a ligand, comprising:

(i) binding at least one fluorescent molecular rotor to said ligand or protein; and (ii) detecting a change in fluorescence emitted by said fluorescent molecular rotor after contact of the bound fluorescent molecular rotor with the other of said ligand or protein, thereby detecting an interaction between the ligand and the protein, wherein the fluorescent molecular rotor is selected from the group consisting of:

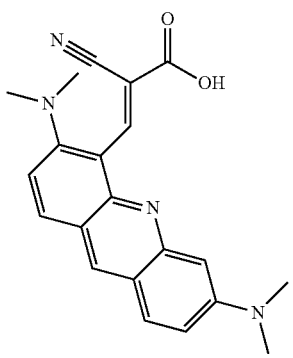

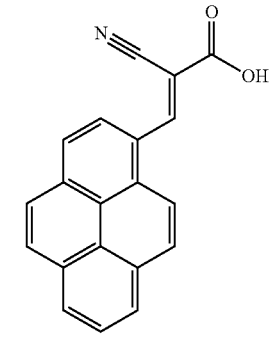

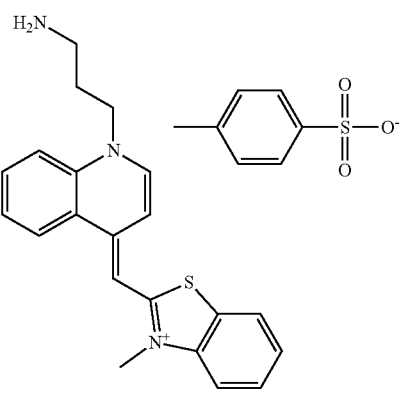

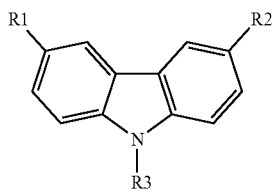

wherein at least one of R1, R2 or R3 is

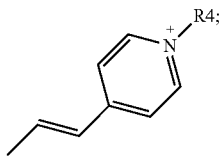

R1, R2, R3 and R4 are independently chosen from the group consisting of: optionally substituted alkyl, optionally substituted alkenyl, optionally substituted alkynyl, optionally substituted aryl, optionally substituted heteroaryl, optionally substituted cycloalkyl or optionally substituted heterocyclyl.

In a third aspect, there is provided a method for detecting an interaction between (a) DNA and protein, (b) MDM2 protein and a peptide, or (c) biotin and streptavidin, the method comprising:

(i) binding at least one fluorescent molecular rotor to said ligand or protein; and (ii) detecting a change in fluorescence emitted by said fluorescent molecular rotor after contact of the bound fluorescent molecular rotor with the other of said ligand or protein, thereby detecting an interaction between the ligand and the protein, wherein the fluorescent molecular rotor is selected from the group consisting of:
a rotating σ-bond;
an electron-donating moiety;
an electron-accepting moiety; and
a π-conjugated linker.

Advantageously, the fluorescent molecular rotors may be useful as fluorescent probes for determining protein-ligand interactions. The fluorescent molecular rotors may be useful as a fluorescent probe due to the restriction of intramolecular rotation within the molecular rotor through binding to a ligand.

The fluorescent molecular rotors may display a change in fluorescence upon being displaced from the ligand, perturbed by protein binding or from greater restriction of their intramolecular rotation.

Advantageously, the fluorescent molecular rotors may be used to investigate protein-DNA interactions. The fluorescent molecular rotors may be engineered such that the intercalating moiety of the rotor encompasses the entire base pair region of DNA, so that the rotating bond will be protruding out of the DNA duplex.

The fluorescent molecular rotors capable of intercalating DNA can first be bound to DNA then incubated with a protein. Interaction of the protein with the DNA could displace the fluorescent molecular rotor from DNA, or result in a greater restriction of its intramolecular rotation. In both cases, a change in fluorescence may be measured.

Advantageously, the fluorescent molecular rotors may be used to investigate protein-peptide interactions. The peptide may be a protein-binding peptide which is conjugated to fluorescent molecular rotor(s). The peptide binding site on the protein may restrict the motion of the fluorescent molecular rotor(s) attached to the peptide sufficiently to bring about a detectable fluorescence turn-on signal.

In a fourth aspect, there is provided a composition comprising a fluorescent molecular rotor. The composition may further comprise a ligand and a protein, wherein at least one fluorescent molecular rotor is bound to the ligand or the protein, with the proviso that the fluorescent molecular rotor is not a compound selected from the following table:

| | Structure | R groups |
|---|---|---|
| 1 | (7-diethylamino-2-oxo-2H-chromen-3-yl) with CN and CO₂H substituents | |
| 2 | methylbenzothiazolium with dimethylaminophenyl | |
| 3 | dimethylaminophenyl dienedinitrile | |
| 4 | 1-methyl-2-[(E)-2-(4-dimethylaminophenyl)vinyl]pyridinium | |
| 5 | 1-methyl-4-[(E)-2-(4-dimethylaminophenyl)vinyl]pyridinium | |
| 6 | 1-methyl-2-[(E)-2-(4-dimethylaminophenyl)vinyl]quinolinium | |
| 7 | 1-methyl-4-[(E)-2-(4-dimethylaminophenyl)vinyl]quinolinium | |
| 8 | julolidine with CH=C(CO₂R₁)(CO₂R₂) | |
| 9 | julolidine with CH=C(CN)(COR) | R = OH, OEt, NH₂ |

-continued
| | Structure | R groups |
|---|---|---|
| 10 | 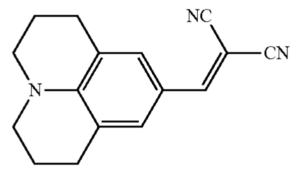 | |
| 11 | 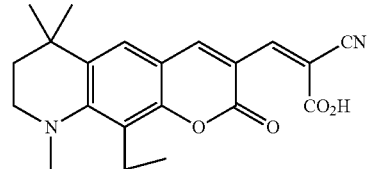 | |
| 12 | 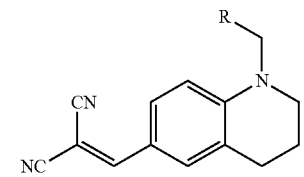 | R = COOH, CO₂Et, CH₂OH, CH₂OAc, CH₂Cl |
| 13 | 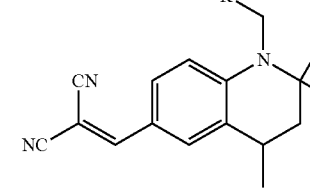 | R = CO₂CO₂Ph |
| 14 | 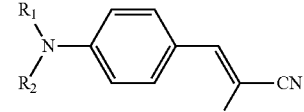 | R₁, R₂ = CH₃ |
| 15 | 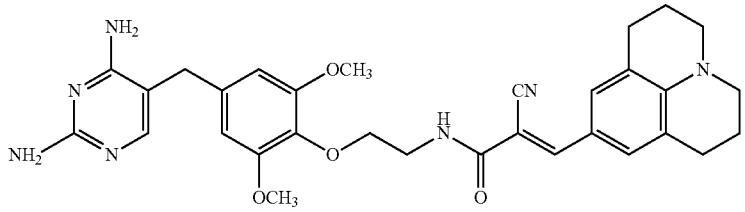 | |
| 16 | 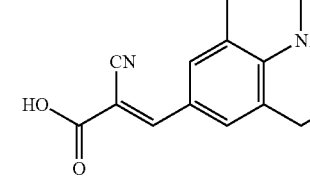 | |
| 17 | 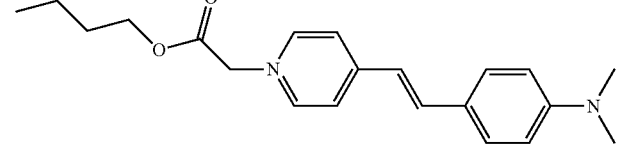 | |

In a fifth aspect, there is provided a composition comprising a fluorescent molecular rotor, wherein the fluorescent molecular rotor is selected from the group consisting of:

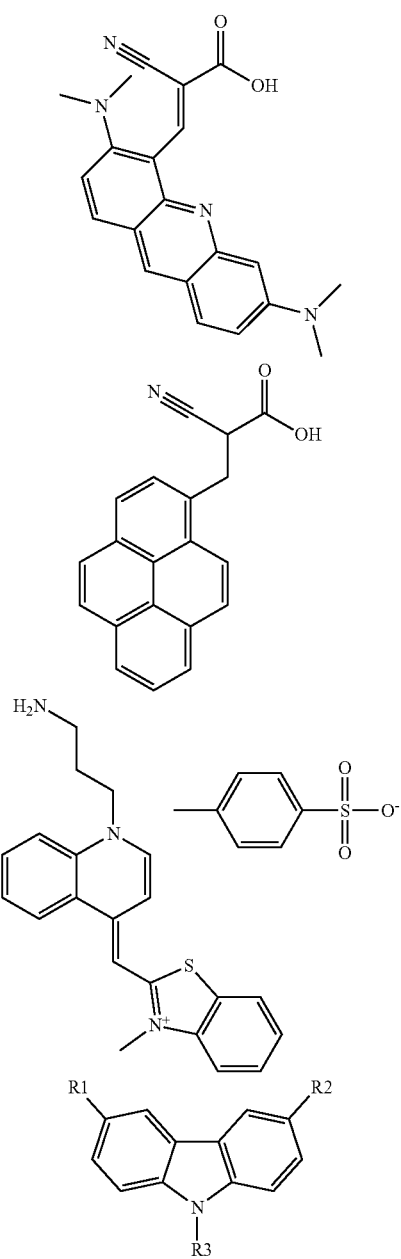

wherein at least one of R1, R2 or R3 is

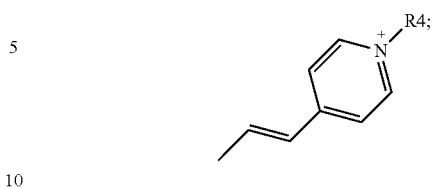

and R1, R2, R3 and R4 are independently chosen from the group consisting of: optionally substituted alkyl, optionally substituted alkenyl, optionally substituted alkynyl, optionally substituted aryl, optionally substituted heteroaryl, optionally substituted cycloalkyl or optionally substituted heterocyclyl.

In a sixth aspect, there is provided a composition comprising:

(i) fluorescent molecular rotor, DNA and protein;

(ii) fluorescent molecular rotor, peptide and MDM2; or (iii) fluorescent molecular rotor, biotin and streptavidin, wherein said fluorescent molecular rotor is bound to one of DNA or protein in (a), one of peptide or MDM2 in (b), or one of biotin or streptavidin in (c), and wherein the fluorescent molecular rotor(s) comprises:

a rotating σ-bond;

an electron-donating moiety;

an electron-accepting moiety; and a π-conjugated linker.

In a seventh aspect, there is provided a screening assay for identifying a ligand, the assay comprising:

(i) providing a protein to be tested for binding affinity with a candidate ligand;

(ii) providing candidate ligands bound to at least one fluorescent molecular rotor;

(iii) testing the candidate ligands for binding affinity by contacting said protein with said candidate ligands bound to at least one fluorescent molecular rotor; and identifying relevant candidate ligands by measuring a change in fluorescence emitted by the fluorescent molecular rotor(s), with the proviso that the fluorescent molecular rotor is not a compound selected from the following table:

| | Structure | R groups |
|---|---|---|
| 1 | 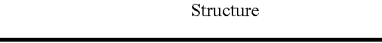 | |

-continued

| | Structure | R groups |
|---|---|---|
| 2 | 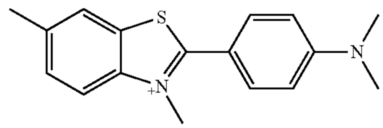 | |
| 3 | 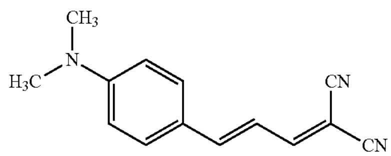 [SMILES: CN(C)c1ccc(/C=C/C=C(C#N)C#N)cc1] | |
| 4 | 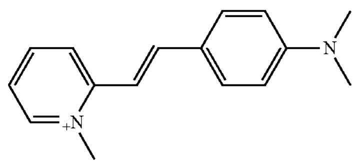 [SMILES: CN(C)c1ccc(/C=C/c2cccc[n+]2C)cc1] | |
| 5 | 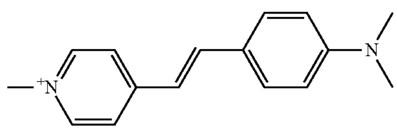 | |
| 6 | 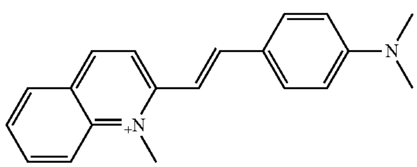 [SMILES: CN(C)c1ccc(/C=C/c2ccc3ccccc3[n+]2C)cc1] | |
| 7 | 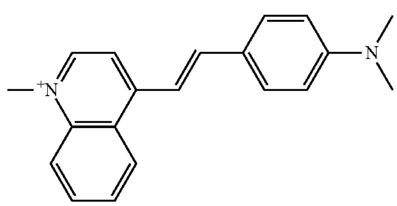 | |
| 8 | 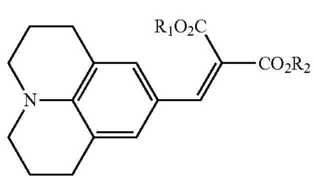 | |
| 9 | 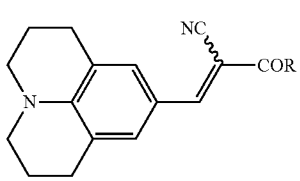 | R = OH, OEt, NH$_2$ |
| 10 | 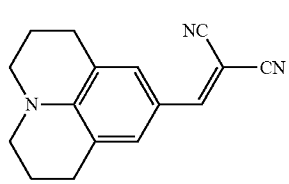 [SMILES: N#CC(C#N)=Cc1cc2c3c(c1)CCCN3CCC2] | |

| | Structure | R groups |
|---|---|---|
| 11 | 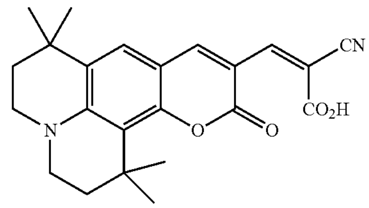 [SMILES: CC1(C)CCN2CCC(C)(C)c3c2c1cc1cc(/C=C(/C#N)C(=O)O)c(=O)oc31] | |
| 12 | 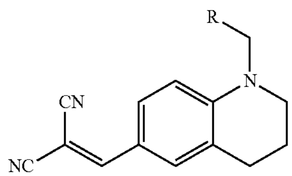 | R = COOH, CO₂Et, CH₂OH, CH₂OAc, CH₂Cl |
| 13 | 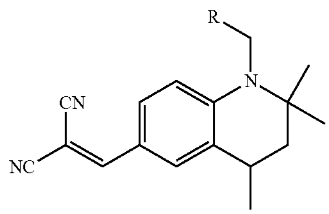 | R = CO₂CO₂Ph |
| 14 | 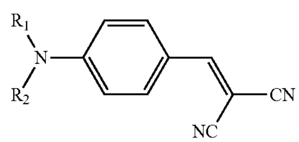 | R₁, R₂ = CH₃ |
| 15 | 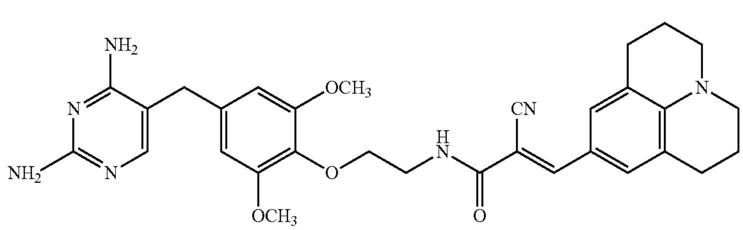 [SMILES: COc1cc(Cc2cnc(N)nc2N)cc(OC)c1OCCNC(=O)/C(C#N)=C/c1cc2c3c(c1)CCCN3CCC2] | |
| 16 | 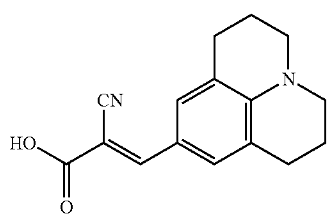 [SMILES: N#C/C(=C\c1cc2c3c(c1)CCCN3CCC2)C(=O)O] | |
| 17 | 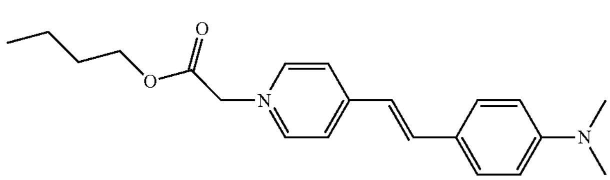 | |

In an eighth aspect, there is provided screening assay for identifying an interaction between a protein and ligand, the assay comprising:

a) providing a protein to be tested for binding affinity with a candidate ligand;

b) providing candidate ligands bound to at least one fluorescent molecular rotor;

c) testing the candidate ligands for binding affinity by contacting said protein with said candidate ligands bound to at least one fluorescent molecular rotor; and d) identifying a relevant interaction by measuring a change in fluorescence emitted by the fluorescent molecular rotor(s), wherein the fluorescent molecular rotor is selected from the group consisting of:

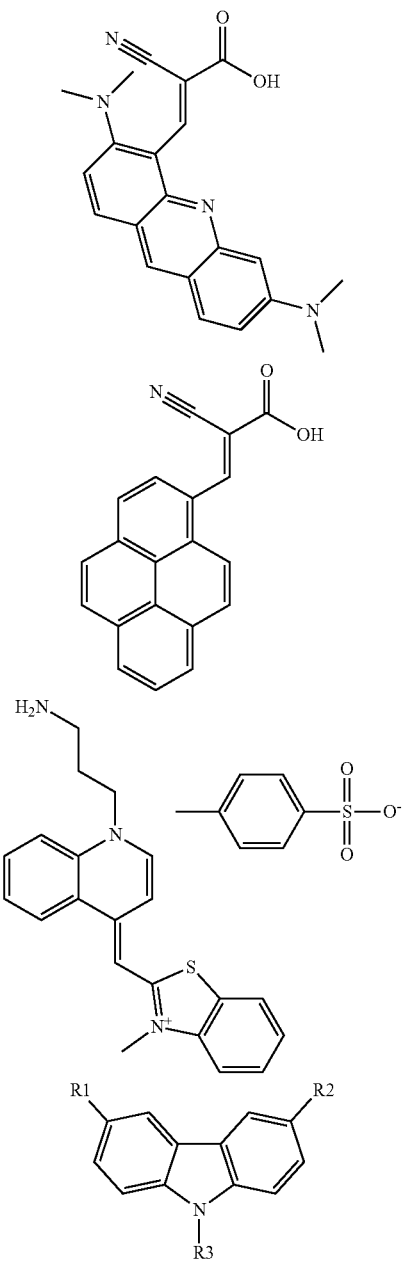

wherein at least one of R1, R2 or R3 is

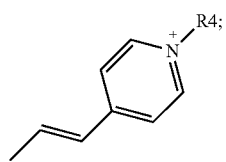

and R1, R2, R3 and R4 are independently chosen from the group consisting of: optionally substituted alkyl, optionally substituted alkenyl, optionally substituted alkynyl, optionally substituted aryl, optionally substituted heteroaryl, optionally substituted cycloalkyl or optionally substituted heterocyclyl.

In a ninth aspect, there is provided a screening assay for identifying an interaction between DNA and protein, or peptide and MDM2, the assay comprising:
a) providing a protein to be tested for binding affinity with candidate DNA or peptide;
b) providing candidate DNA or peptide bound to at least one fluorescent molecular rotor;
c) testing the candidate DNA or peptide for binding affinity by contacting said protein with said candidate DNA or peptide bound to at least one fluorescent molecular rotor; and
d) identifying a relevant interactions by measuring a change in fluorescence emitted by the fluorescent molecular rotor(s),
wherein the fluorescent molecular rotor(s) comprises:
a rotating σ-bond;
an electron-donating moiety;
an electron-accepting moiety; and
a π-conjugated linker.

In a tenth aspect, there is provided a screening assay for identifying a candidate compound, comprising:
(a) providing a candidate compound to be tested for binding affinity with protein;
(b) providing a complex comprising a probe bound to protein, wherein said probe comprises at least one fluorescent molecular rotor bound to peptide;
(c) testing the candidate compound for binding affinity with said protein by contacting said candidate compound with said complex; and
(d) identifying a relevant candidate compound by measuring the change in fluorescence emitted when said complex is disrupted, wherein the fluorescent molecular rotor(s) comprises:
a rotating σ-bond;
an electron-donating moiety;
an electron-accepting moiety; and
a π-conjugated linker.

Advantageously, the screening assay may be high-throughput, quantitative, label-free, homogenous, non-radioactive and a reproducible method to measure protein-ligand binding.

Advantageously, the screening assay may be non-laborious and may not require the use of expensive instrumentation.

Advantageously, the screening method may not require multiple washing steps.

Advantageously, the assay is single-well, low volume and non-radioactive with minimal pipetting steps and fluorescent readout.

Advantageously, the screening assay may be a small molecule drug screening assay which may identify small molecules which may be missed in assays, such as fluorescence polarization.

In an eleventh aspect, there is provided a kit for carrying out the first or sixth aspects of the invention, comprising a ligand, protein and fluorescent molecular rotor(s), and a means to detect a change in fluorescence.

In a twelfth aspect, there is provided a kit for carrying out the second or seventh aspects of the invention comprising the ligand, protein and fluorescent molecular rotor(s), and a means to detect a change in fluorescence.

In a thirteenth aspect, there is provided a kit for carrying out the third or eighth aspects of the invention comprising the ligand, protein and fluorescent molecular rotor(s), and a means to detect a change in fluorescence.

In a fourteenth aspect, there is provided a chemical compound selected from the group consisting of:

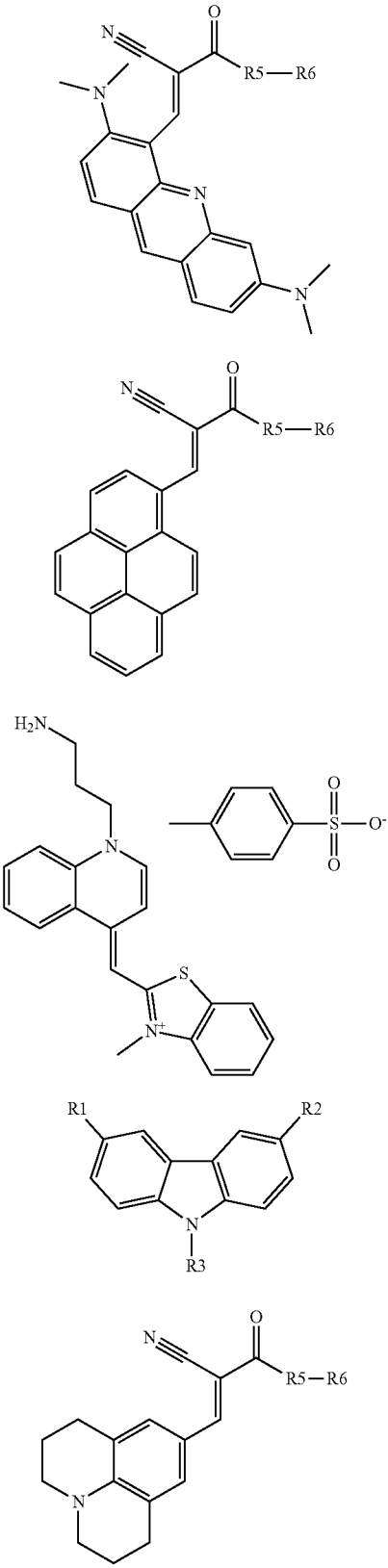

wherein at least one of R1, R2 or R3 is

R1, R2, R3 and R4 are independently chosen from the group consisting of: optionally substituted alkyl, optionally substituted alkenyl, optionally substituted alkynyl, optionally substituted aryl, optionally substituted heteroaryl, optionally substituted cycloalkyl or optionally substituted heterocyclyl;

R5 is a OH or a linking moiety selected from the group consisting of a single bond; or optionally substituted heteroalkyl, wherein the main chain atoms of said optionally substituted heteroalkyl are optionally interrupted by one or more optionally substituted cyclic groups; and R6 is absent or a ligand, with the proviso that R5 is not OH in formula (v).

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

As used herein, unless otherwise specified, the following terms have the following meanings, and unless otherwise specified, the definitions of each term (i.e. moiety or substitutent) apply when that term is used individually or as a component of another term (e.g., the definition of aryl is the same for aryl and for the aryl portion of arylalkyl, alkylaryl, arylalkynyl, and the like).

As used herein, the term "alkyl" includes within its meaning monovalent ("alkyl") and divalent ("alkylene") straight chain or branched chain saturated aliphatic groups having from 1 to 6 carbon atoms, eg, 1, 2, 3, 4, 5 or 6 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl and the like. Alkyl groups may be optionally substituted.

As used, herein, the term "alkenyl" refers to divalent straight chain or branched chain unsaturated aliphatic groups containing at least one carbon-carbon double bond and having from 2 to 6 carbon atoms, eg, 2, 3, 4, 5 or 6 carbon atoms. For example, the term alkenyl includes, but is not limited to, ethenyl, propenyl, butenyl, 1-butenyl, 2-butenyl, 2-methylpropenyl, 1-pentenyl, 2-pentenyl, 2-methylbut-1-enyl, 3-methylbut-1-enyl, 2-methylbut-2-enyl, 1-hexenyl, 2-hexenyl, 3-hexenyl, 2,2-dimethyl-2-butenyl, 2-methyl-2-hexenyl, 3-methyl-1-pentenyl, 1,5-hexadienyl and the like. Alkenyl groups may be optionally substituted.

As used herein, the term "alkynyl" refers to trivalent straight chain or branched chain unsaturated aliphatic groups containing at least one carbon-carbon triple bond and having from 2 to 6 carbon atoms, eg, 2, 3, 4, 5 or 6 carbon atoms. For example, the term alkynyl includes, but is not limited to, ethynyl, propynyl, 1-butynyl, 2-butynyl, 1-pentynyl, 2-pentynyl, 1-hexynyl, 2-hexynyl, 3-hexynyl, 3-methyl-1-pentynyl, and the like, alkynyl groups may be optionally substituted.

The term "aryl", or variants such as "aromatic group" or "arylene" as used herein refers to monovalent ("aryl") and divalent ("arylene") single, polynuclear, conjugated or fused residues of aromatic hydrocarbons having from 6 to 10 carbon atoms. Such groups include, for example, phenyl, biphenyl, naphthyl, phenanthrenyl, and the like. Aryl groups may be optionally substituted.

The term "cycloalkyl" as used herein refers to a non-aromatic mono- or multicyclic ring system comprising about 3 to about 10 carbon atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

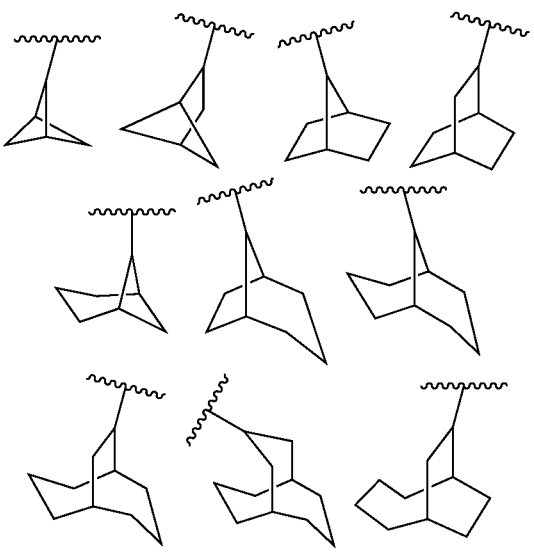

-continued

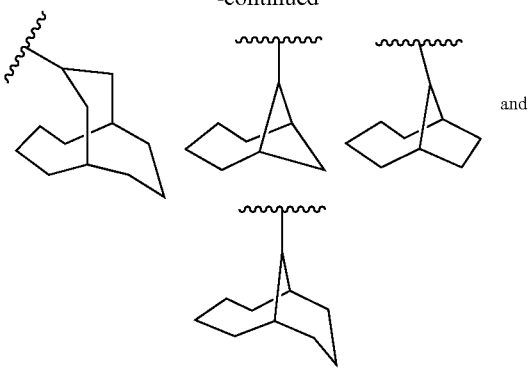

and

The term "cycloalkenyl" as used herein refers to a non-aromatic mono or multicyclic ring system comprising about 3 to about 10 carbon atoms which contains at least one carbon-carbon double bond. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl, as well as unsaturated moieties of the examples shown above for cycloalkyl. Cycloalkenyl groups may be optionally substituted.

The term "heteroalkyl" as used herein refers to an alkyl moiety as defined above, having one or more carbon atoms, for example 1, 2, 3, 4, 5, 6, 7, 8, 9, 10 carbon atoms, replaced with one or more heteroatoms, which may be the same or different, where the point of attachment to the remainder of the molecule is through a carbon atom of the heteroalkyl radical, or the heteroatom. Suitable heteroatoms include O, S, and N. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like. Heteroalkyl groups may be optionally substituted.

The term "heteroaryl" as used herein refers to an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. Heteroaryl groups may be optionally substituted.

The term "heterocycle" as used herein refers to a group comprising a covalently closed ring herein at least one atom forming the ring is a carbon atom and at least one atom forming the ring is a heteroatom. Heterocyclic rings may be formed by three, four, five, six, seven, eight, nine, or more than nine atoms, any of which may be saturated, partially unsaturated, or aromatic. Any number of those atoms may be heteroatoms (i.e., a heterocyclic ring may comprise one, two, three, four, five, six, seven, eight, nine, or more than nine heteroatoms). Herein, whenever the number of carbon atoms in a heterocycle is indicated (e.g., C1-C6 heterocycle), at least one other atom (the heteroatom) must be present in the ring. Designations such as "C1-C6 heterocycle" refer only to the number of carbon atoms in the ring and do not refer to the total number of atoms in the ring. It is understood that the heterocylic ring will have additional heteroatoms in the ring. In heterocycles comprising two or more heteroatoms, those two or more heteroatoms may be the same or different from one another. Heterocycles may be optionally substituted. Binding to a heterocycle can be at a heteroatom or via a carbon atom. Examples of heterocycles include heterocycloalkyls (where the ring contains fully saturated bonds) and heterocycloalkenyls (where the ring contains one or more unsaturated bonds) such as but are not limited to the following:

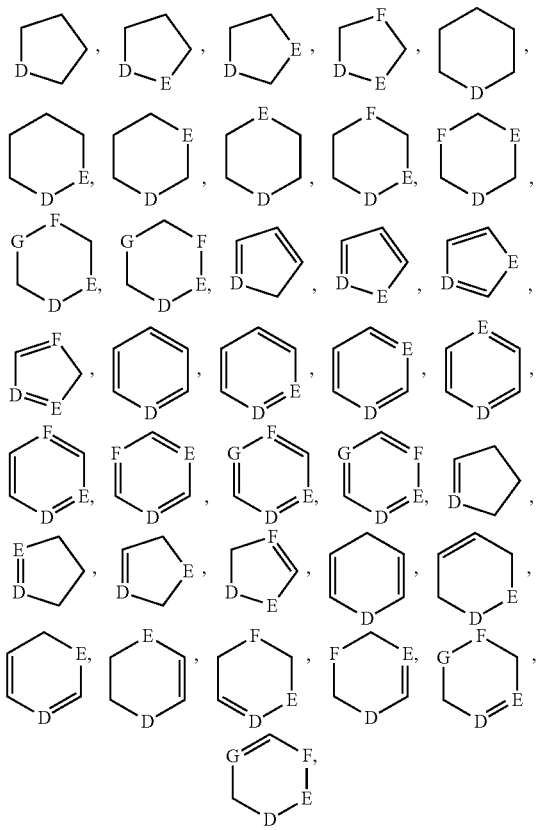

wherein D, E, F, and G independently represent a heteroatom. Each of D, E, F, and G may be the same or different from one another.

The term "cyclic group" as used herein refers to an aryl, heteroaryl, cycloalkyl, cycloalkenyl or heterocycle as defined above. Cyclic groups may be optionally substituted.

The term "optionally substituted" as used herein means the group to which this term refers may be unsubstituted, or may be substituted with one or more groups other than hydrogen provided that the indicated atom's normal valency is not exceeded, and that the substitution results in a stable compound.

The term "linking moiety" as used herein refers to a single bond or optionally substituted heteroalkyl as defined above, wherein the main chain atoms of said optionally substituted heteroalkyl are optionally interrupted by one or more optionally substituted cyclic groups as defined above.

As used herein, the term "main chain atom" refers to only those atoms between the fluorescent molecular rotor and the ligand that are joined in a continuous lines. In one embodiment, main chain atoms are selected from the group consisting of: C, O, N, S, P and Si.

As used herein, the term "ligand" refers to molecules that bind to proteins. Accordingly, a ligand may be a small molecule as defined below, nucleic acid such as RNA or DNA, a polynucleoside or peptide.

"Peptide" as used herein includes a peptide, dipeptide or polypeptide.

A ligand variant peptide may be substantially identical to a native peptide sequence. The amino acid sequence of the variant at times is 50%, 55%, 60%, 65%, 70%, 75%, 80%, 85%, 89%, 90%, 91%, 92%, 93%, 94%, 95%, 96%, 97%, 98%, 99%, or more identical to a native peptide sequence.

Naturally occurring amino acids in a native ligand or receptor protein polypeptide or protein may be are substituted with unnatural or non-classical amino acids, which include, but are not limited to, ornithine (hereinafter referred to as Z), diaminobutyric acid (hereinafter referred to as B), norleucine (hereinafter referred to as O), pyrylalanine, thienylalanine, naphthylalanine and phenylglycine. Other examples of non-naturally occurring amino acids and non-classical amino acid replacements are alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, beta-alanine*, L-arpha-amino butyric acid*, L-gamma-amino butyric acid*, L-alpha-amino isobutyric acid*, L-epsilon-amino caproic acid#, 7-amino heptanoic acid*, L-methionine sulfone*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid, L-Phe (4-benzyl)*, 2,4-diaminobutyric acid, 4-aminobutyric acid (gamma-Abu), 2-amino butyric acid (alpha-Abu), 6-amino hexanoic acid (epsilon-Ahx), 2-amino isobutyric acid (Aib), 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, fluoroamino acids, designer amino acids such as beta-methyl amino acids, Ca-methyl amino acids, Na-methyl amino acids, naphthyl alanine, and the like. The notation * indicates a derivative having hydrophobic characteristics, # indicates a derivative having hydrophilic characteristics, and #* indicates a derivative having amphipathic characteristics.

Variant amino acid sequences may include suitable spacer groups inserted between any two amino acid residues of the sequence including alkyl groups such as methyl, ethyl or propyl groups in addition to amino acid spacers such as glycine or [beta]-alanine residues. Also, peptides and polypeptides may comprise or consist of peptoids. The term "peptoids" refers to variant amino acid structures where the [alpha]-carbon substituent group is on the backbone nitrogen atom rather than the [alpha]-carbon.

Peptides may be prepared by known recombinant molecular biology procedures. A polypeptide also may be synthesized by peptide ligation methods. This method allows native backbone proteins to be assembled from fully unprotected polypeptide building blocks. To facilitate the ligation reactions, the alpha-carboxylate group of the N-terminal polypeptide fragment is mildly activated as an aryl thioester and the C-terminal polypeptide fragment contains an amino-terminal cysteine. The reaction often is carried out in aqueous buffer at about neutral pH. The initial step is a reversible transthioesterification reaction involving the thiol group of the N-terminal Cys-polypeptide (the C-terminal fragment) and the alpha-thioester moiety of the N-terminal polypeptide fragment. This intermediate undergoes a spontaneous rearrangement to form a natural peptide bond at the ligation site. An advantage of the chemical approach is the site-specific incorporation of unnatural amino acids, post-translational modifications, and biochemical/biophysical probes into the target molecule. Polypeptide fragments of about 50 amino acids or less, and mimetics and variants thereof, may be produced by standard chemical synthetic methods known in the art.

The ligands, variant polypeptides and proteins thereof may be isolated using standard purification procedures. An "isolated" or "purified" peptide, polypeptide or protein is substantially free of cellular material or other contaminating proteins from the cell or tissue source from which the protein is derived, or substantially free from chemical precursors or other chemicals when chemically synthesized. "Substantially free" means preparation of a ligand, receptor, or peptide, polypeptide or protein variant thereof having less than about 30%, 20%, 10% and more preferably 5% (by dry weight), of non-receptor or ligand polypeptides (also referred to herein as a "contaminating proteins"), or of chemical precursors or non-receptor or ligand chemicals. When the polypeptide or a biologically active portion thereof is produced recombinantly, it often is substantially free of culture medium, specifically, where culture medium represents less than about 20%, less than about 10%, and often less than about 5% of the volume of the polypeptide preparation. Isolated or purified polypeptide preparations may be 0.01 milligrams or more or 0.1 milligrams or more, and often 1.0 milligrams or more and 10 milligrams or more in dry weight.

As used herein, the term "small molecule" refers to peptides, peptidomimetics (e.g., peptoids), amino acids, amino acid analogs, polynucleotides, polynucleotide analogs, nucleotides, nucleotide analogs, organic or inorganic compounds (i.e., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this specification, unless the context requires otherwise, the word "comprise", or variations such as "comprises" or "comprising", will be understood to imply the inclusion of a stated step or element or integer or group of steps or elements or integers, but not to the exclusion of any other step or element or integer or group of elements or integers. Thus, in the context of this specification, the term "comprising" means "including peripherally, but not necessarily solely".

The word "substantially" does not exclude "completely" e.g. a composition which is "substantially free" from Y may be completely free from Y. Where necessary, the word "substantially" may be omitted from the definition of the invention.

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

DETAILED DISCLOSURE OF EMBODIMENTS

Exemplary, non-limiting embodiments of the invention will now be disclosed.

In a first aspect, there is a provided a method for detecting an interaction between a protein and a ligand, comprising:
(i) binding at least one fluorescent molecular rotor to said ligand or protein; and
(ii) detecting a change in fluorescence emitted by said fluorescent molecular rotor after contact of the bound fluorescent molecular rotor with the other of said ligand or protein, thereby detecting an interaction between the ligand and the protein,
wherein the fluorescent molecular rotor comprises:
 a rotating σ-bond;
 an electron-donating moiety;
 an electron-accepting moiety; and
 a π-conjugated linker,
with the proviso that the fluorescent molecular rotor is not a compound selected from the following table:

| | Structure | R groups |
|---|---|---|
| 1 | 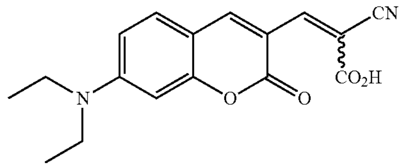 [SMILES: CCN(CC)c1ccc2cc(C=C(C#N)C(=O)O)c(=O)oc2c1] | |
| 2 | 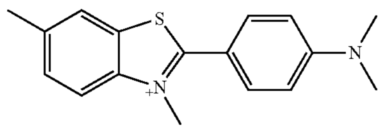 | |
| 3 | 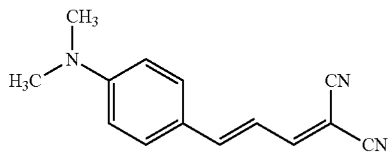 [SMILES: CN(C)c1ccc(/C=C/C=C(C#N)C#N)cc1] | |
| 4 | 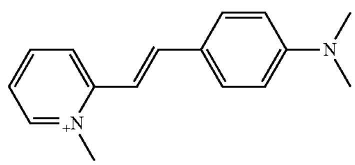 [SMILES: CN(C)c1ccc(/C=C/c2cccc[n+]2C)cc1] | |
| 5 | 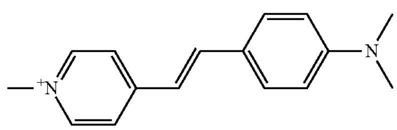 | |
| 6 | 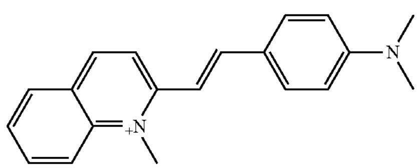 [SMILES: CN(C)c1ccc(/C=C/c2ccc3ccccc3[n+]2C)cc1] | |
| 7 | 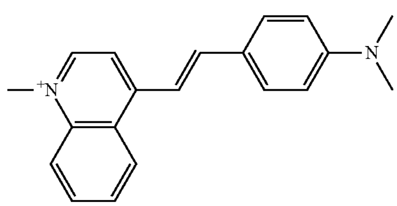 | |
| 8 | 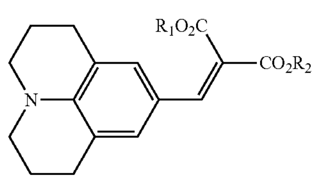 | |
| 9 | 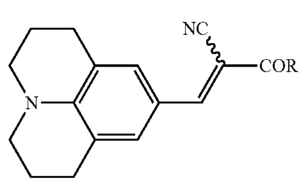 | R = OH, OEt, $NH_2$ |

| | Structure | R groups |
|---|---|---|
| 10 | 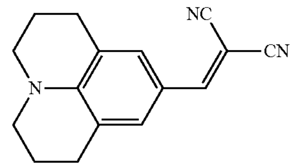 [SMILES: N#CC(C#N)=Cc1cc2c3c(c1)CCCN3CCC2] | |
| 11 | 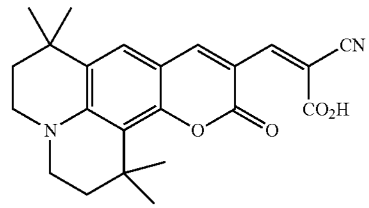 [SMILES: CC1(C)CCN2CCC(C)(C)c3c2c1cc1cc(/C=C(/C#N)C(=O)O)c(=O)oc31] | |
| 12 | 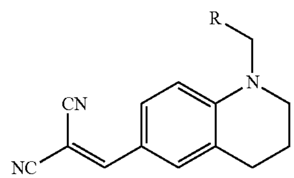 | R = COOH, CO₂Et, CH₂OH, CH₂OAc, CH₂Cl |
| 13 | 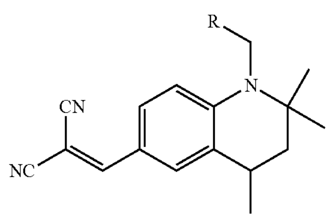 | R = CO₂CO₂Ph |
| 14 | 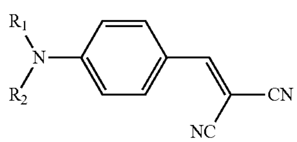 | R₁, R₂ = CH₃ |
| 15 | 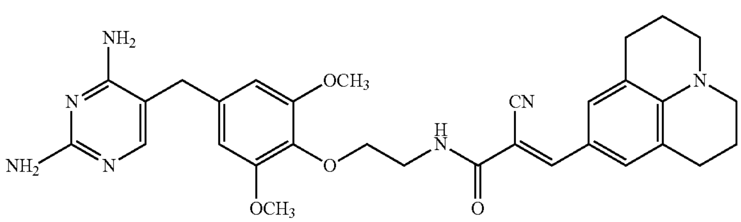 [SMILES: COc1cc(Cc2cnc(N)nc2N)cc(OC)c1OCCNC(=O)/C(C#N)=C/c1cc2c3c(c1)CCCN3CCC2] | |
| 16 | 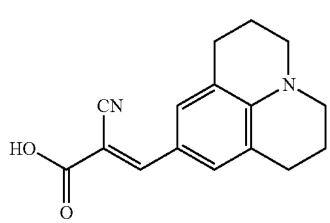 [SMILES: N#C/C(=C\c1cc2c3c(c1)CCCN3CCC2)C(=O)O] | |
| 17 | 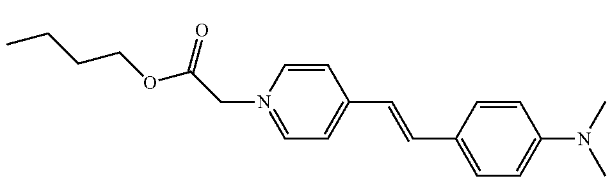 | |

In the method for detecting an interaction between a protein and a ligand according to the first aspect, the fluorescent molecular rotor(s) may exhibit a change in fluorescence when the ligand binds to the protein.

There is also provided a composition according to a fourth aspect, comprising a fluorescent molecular rotor, wherein the fluorescent molecular rotor comprises:

a rotating σ-bond;
an electron-donating moiety;
an electron-accepting moiety; and
a π-conjugated linker,
with the proviso that the fluorescent molecular rotor is not a compound selected from the following table:

| | Structure | R groups |
|---|---|---|
| 1 | [structure: 7-diethylamino coumarin with CN/CO₂H vinyl substituent] | |
| 2 | [structure: methylbenzothiazolium with dimethylaminophenyl] | |
| 3 | [structure: 4-dimethylaminophenyl diene with dicyanomethylene] | |
| 4 | [structure: N-methyl-2-pyridinium styryl dimethylaminophenyl] | |
| 5 | [structure: N-methyl-4-pyridinium styryl dimethylaminophenyl] | |
| 6 | [structure: N-methyl-2-quinolinium styryl dimethylaminophenyl] | |
| 7 | [structure: N-methyl-4-isoquinolinium styryl dimethylaminophenyl] | |
| 8 | [structure: julolidine with R₁O₂C and CO₂R₂ substituents] | |

-continued

| | Structure | R groups |
|---|---|---|
| 9 | 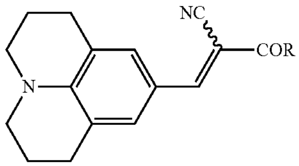 | R = OH, OEt, NH$_2$ |
| 10 | 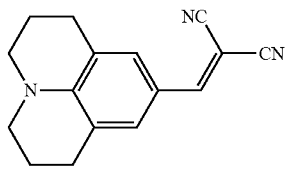 [SMILES: N#CC(C#N)=Cc1cc2c3c(c1)CCCN3CCC2] | |
| 11 | 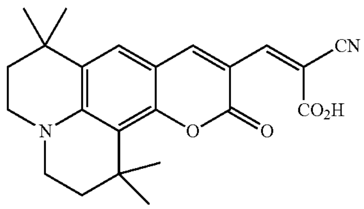 [SMILES: CC1(C)CCN2CCC(C)(C)c3c2c1cc1cc(/C=C(/C#N)C(=O)O)c(=O)oc31] | |
| 12 | 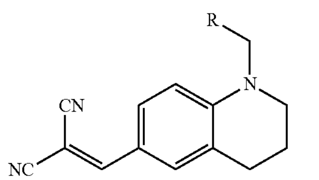 | R = COOH, CO$_2$Et, CH$_2$OH, CH$_2$OAc, CH$_2$Cl |
| 13 | 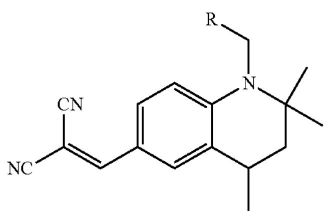 | R = CO$_2$CO$_2$Ph |
| 14 | 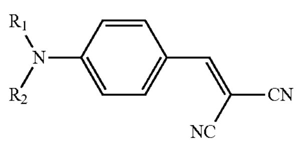 | R$_1$, R$_2$ = CH$_3$ |
| 15 | 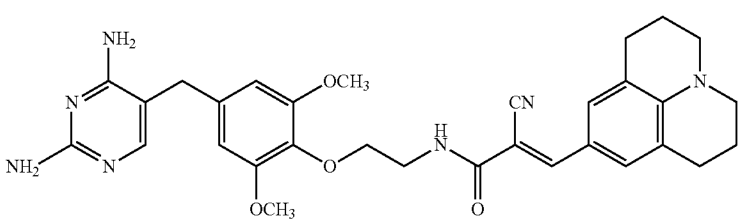 [SMILES: COc1cc(Cc2cnc(N)nc2N)cc(OC)c1OCCNC(=O)/C(C#N)=C/c1cc2c3c(c1)CCCN3CCC2] | |
| 16 | 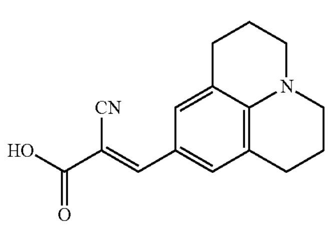 [SMILES: N#C/C(=C\c1cc2c3c(c1)CCCN3CCC2)C(=O)O] | |

| Structure | R groups |
|---|---|
| 17 ![structure 17] | |

The fluorescent molecular rotor(s) of the first or fourth aspects may be bound to a ligand or a protein via a linking moiety.

In one embodiment of the first or fourth aspects, the fluorescent molecular motor(s) may be bound via a linking moiety to the ligand.

In another embodiment of the first or fourth aspects, the fluorescent molecular motor(s) may be bound via a linking moiety to the protein.

The linking moiety of the first or fourth aspects may comprise 1 to 20 main chain atoms, 1 to 15 main chain atoms, 1 to 10 main chain atoms, or 1 to 5 main chain atoms.

The linking moiety of the first or fourth aspects may be a single bond or optionally substituted heteroalkyl. Said heteroalkyl may be optionally substituted heteroalkyl selected from ethers, thioethers, amines, hydroxymethyl, 3-hydroxypropyl, 1,2-dihydroxyethyl, 2-methoxyethyl, 2-aminoethyl, 2-dimethylaminoethyl, alkoxyalkylamines, alkoxyalkylamides, aminoheteroalkyl substituted with oxo or aminoalkyls. The linking moiety may be:

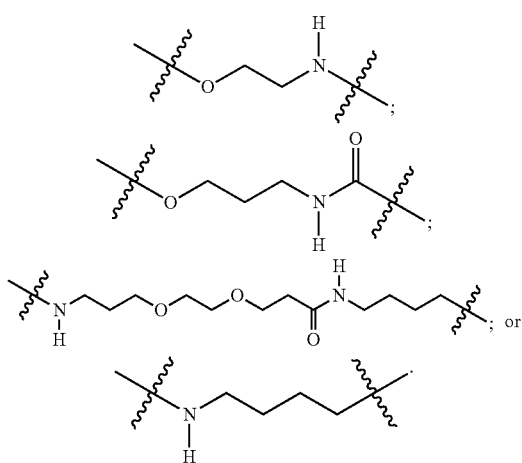

The optionally substituted heteroalkyl may be optionally interrupted by one or more optionally substituted cyclic groups. Said cyclic groups may be aryl, heteroaryl, cycloalkyl, cycloalkenyl or heterocycle. Cyclic groups may be selected from phenyl, biphenyl, naphthyl, phenanthrenyl, cyclopropyl, cyclopentyl, cyclohexyl, cycloheptyl, 1-decalinyl, norbornyl, adamantyl, cyclopentenyl, cyclohexenyl, cyclohepta-1,3-dienyl, norbornylenyl, piperidyl, pyrrolidinyl, piperazinyl, morpholinyl, thiomorpholinyl, thiazolidinyl, 1,4-dioxanyl, tetrahydrofuranyl, tetrahydrothiophenyl, lactam or lactone. Cyclic, groups may be optionally substituted.

In one embodiment of the first or fourth aspects, the change in fluorescence may occur when the binding of protein to ligand displaces the fluorescent molecular rotor(s) from the ligand or perturbs the fluorescent molecular rotor(s).

In another embodiment of the first or fourth aspects, the change in fluorescence may occur when the binding of protein to ligand displaces the fluorescent molecular rotor(s) from the protein or perturbs the fluorescent molecular rotor(s).

The ligand of the first or fourth aspects may be a molecule that binds to protein. Accordingly, a ligand may be a small molecule, nucleic acid such as RNA or DNA, a polynucleoside or peptide. "Peptide" may refer to a peptide, dipeptide or polypeptide. A ligand variant peptide may be substantially identical to a native peptide sequence. The amino acid sequence of the variant at times is 50%, 55%, 60%, 65%, 70%, 75%, 80%, 85%, 89%, 90%, 91%, 92%, 93%, 94%, 95%, 96%, 97%, 98%, 99%, or more identical to a native peptide sequence. In one embodiment, the ligand may be a binding peptide derived from p53 protein. In another embodiment, the ligand may be a peptide selected from JP1: MPRFMDYWEGLSK or JP2: MPRFMDYWEGLNK.

In another embodiment of the first or fourth aspects, the ligand may be DNA.

In yet another embodiment of the first or fourth aspects, the ligand may be a small molecule. The small molecule may be peptidomimetics (e.g., peptoids), amino acids, amino acid analogs, polynucleotides, polynucleotide analogs, nucleotides, nucleotide analogs, organic or inorganic compounds (i.e., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. The small molecule may be biotin.

The protein of the first or fourth aspects may contain a region that interacts with a ligand. The protein may be a DNA transacting protein that a DNA molecule having a particular sequence binds to. The DNA transacting protein may be a transcription factor, polymerase, telomerase or recombinase. The protein may be wild-type or mutant p53.

In another embodiment of the first or fourth aspects, the protein may be wild-type or mutant MDM2. The wild-type or mutant MDM2 may bind to a binding peptide derived from p53 protein. The interaction between MDM2 and the binding peptide may be mapped to the N-terminal domain of MDM2 (residues 1-100) and the N-terminal domain of p53 (residues 18-26).

In yet another embodiment of the first or fourth aspects, the protein may be streptavidin.

There is further provided a screening assay according to a seventh aspect for identifying an interaction between protein and ligand, the assay comprising:
(i) providing a protein to be tested for binding affinity with a candidate ligand;
(ii) providing candidate ligands bound to at least one fluorescent molecular rotor;
(iii) testing the candidate ligands for binding affinity by contacting said protein with said candidate ligands bound to at least one fluorescent molecular rotor; and
(iv) identifying relevant interactions by measuring a change in fluorescence emitted by the fluorescent molecular rotor(s), wherein the fluorescent molecular rotor(s) comprises:
a rotating σ-bond;
an electron-donating moiety;
an electron-accepting moiety; and
a π-conjugated linker,
with the proviso that the fluorescent molecular rotor(s) is not a compound selected the following table:

| | Structure | R groups |
|---|---|---|
| 1 | [structure: 7-diethylamino-coumarin with CH=C(CN)(CO2H) substituent] | |
| 2 | [structure: methylbenzothiazolium-phenyl-N(CH3)2] | |
| 3 | [structure: (CH3)2N-phenyl-CH=CH-CH=C(CN)2] | |
| 4 | [structure: N-methylpyridinium-CH=CH-phenyl-N(CH3)2] | |
| 5 | [structure: N-methyl-4-pyridinium-CH=CH-phenyl-N(CH3)2] | |
| 6 | [structure: N-methylquinolinium-CH=CH-phenyl-N(CH3)2] | |
| 7 | [structure: N-methylisoquinolinium-CH=CH-phenyl-N(CH3)2] | |
| 8 | [structure: julolidine with =C(CO2R1)(CO2R2) substituent] | |

-continued
| | Structure | R groups |
|---|---|---|
| 9 | 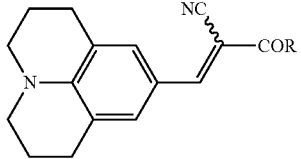 | R = OH, OEt, $NH_2$ |
| 10 | 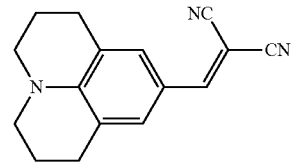 | |
| 11 | 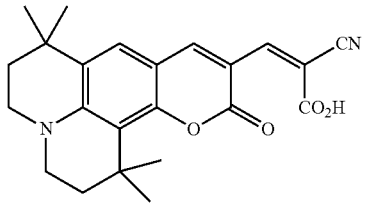 [SMILES: CC1(C)CCN2CCC(C)(C)c3c2c1cc1cc(/C=C(/C#N)C(=O)O)c(=O)oc31] | |
| 12 | 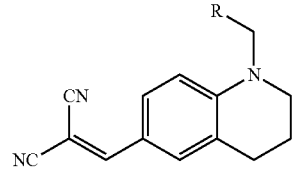 | R = COOH, $CO_2Et$, $CH_2OH$, $CH_2OAc$, $CH_2Cl$ |
| 13 | 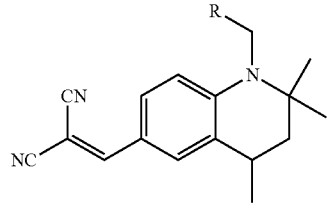 | R = $CO_2CO_2Ph$ |
| 14 | 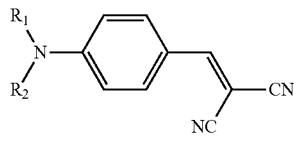 | $R_1, R_2 = CH_3$ |
| 15 | 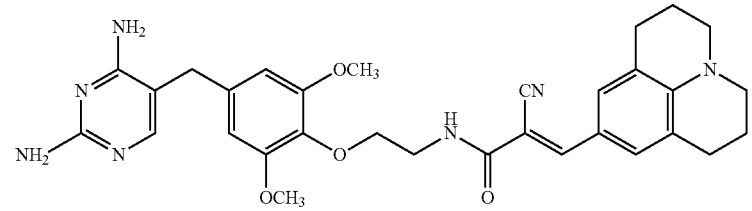 [SMILES: COc1cc(Cc2cnc(N)nc2N)cc(OC)c1OCCNC(=O)/C(C#N)=C/c1cc2c3c(c1)CCCN3CCC2] | |

| Structure | R groups |
|---|---|
| 16 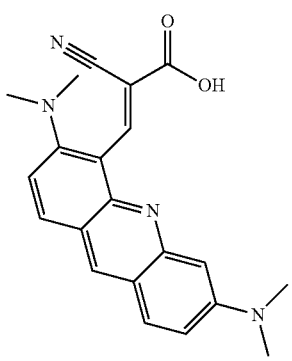 | |
| 17 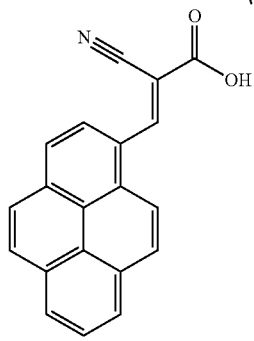 | |

There is also provided a kit according to an eleventh aspect for carrying out a method for detecting an interaction between a protein and a ligand. The kit may comprise ligand, protein, fluorescent molecular rotor(s) and a means to detect a change in fluorescence.

There is further provided a method for detecting an interaction between a protein and a ligand according to a second aspect, comprising:
(i) binding at least one fluorescent molecular rotor to said ligand or protein; and
(ii) detecting a change in fluorescence emitted by said fluorescent molecular rotor after contact of the bound fluorescent molecular rotor with the other of said ligand or protein, thereby detecting an interaction between the ligand and the protein,
wherein the fluorescent molecular rotor is selected from the group consisting of:

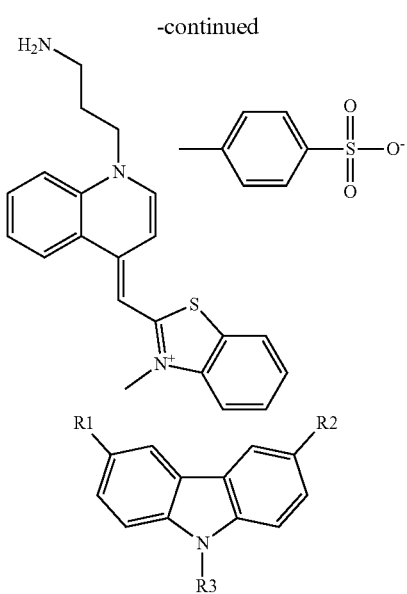

wherein at least one of R1, R2 or R3 is

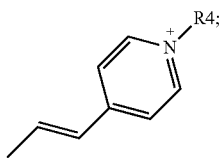

R1, R2, R3 and R4 are independently chosen from the group consisting of: optionally substituted alkyl, optionally substituted alkenyl, optionally substituted alkynyl, optionally substituted aryl, optionally substituted heteroaryl, optionally substituted cycloalkyl or optionally substituted heterocyclyl.

In the method for detecting an interaction between a protein and a ligand according to a second aspect, the fluorescent molecular rotor(s) may exhibit a change in fluorescence when the ligand binds to the protein.

There is also provided a composition according to a fifth aspect comprising a fluorescent molecular rotor, wherein the fluorescent molecular rotor is selected from the group consisting of:

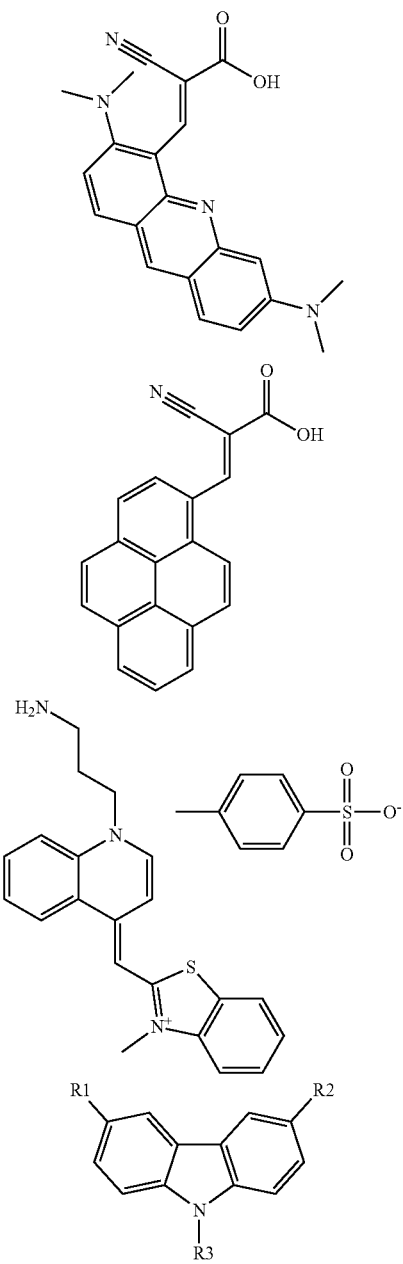

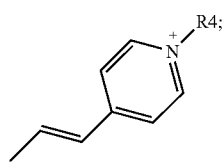

wherein at least one of R1, R2 or R3 is

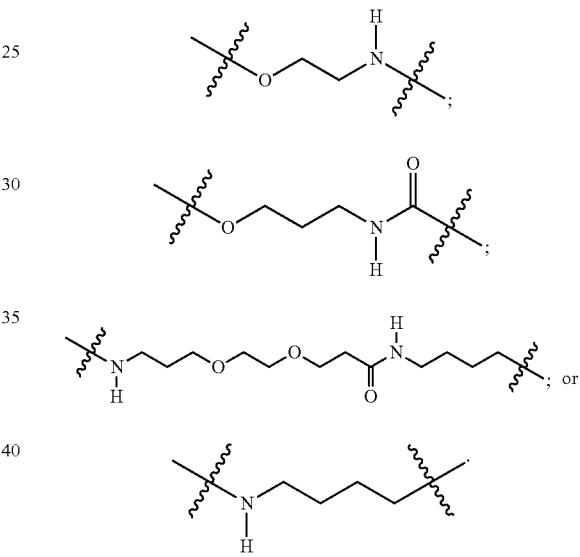

and R1, R2, R3 and R4 are independently chosen from the group consisting of: optionally substituted alkyl, optionally substituted alkenyl, optionally substituted alkynyl, optionally substituted aryl, optionally substituted heteroaryl, optionally substituted cycloalkyl or optionally substituted heterocyclyl.

The fluorescent molecular rotor(s) of the second or fifth aspects may be bound to a ligand or a protein via a linking moiety.

In one embodiment of the second or fifth aspects, the fluorescent molecular motor(s) may be bound via a linking moiety to the ligand.

In another embodiment of the second or fifth aspects, the fluorescent molecular motor(s) may be bound via a linking moiety to the protein.

The linking moiety of the second or fifth aspects may comprise 1 to 20 main chain atoms, 1 to 15 main chain atoms, 1 to 10 main chain atoms, or 1 to 5 main chain atoms.

The linking moiety of the second or fifth aspects may be a single bond or optionally substituted heteroalkyl. Said heteroalkyl may be optionally substituted heteroalkyl selected from ethers, thioethers, amines, hydroxymethyl, 3-hydroxypropyl, 1,2-dihydroxyethyl, 2-methoxyethyl, 2-aminoethyl, 2-dimethylaminoethyl, alkoxyalkylamines, alkoxyalkylamides, aminoheteroalkyl substituted with oxo or aminoalkyls. The linking moiety may be:

The optionally substituted heteroalkyl may be optionally interrupted by one or more optionally substituted cyclic groups. Said cyclic groups may be aryl, heteroaryl, cycloalkyl, cycloalkenyl or heterocycle. Cyclic groups may be selected from phenyl, biphenyl, naphthyl, phenanthrenyl, cyclopropyl, cyclopentyl, cyclohexyl, cycloheptyl, 1-decalinyl, norbornyl, adamantyl, cyclopentenyl, cyclohexenyl, cyclohepta-1,3-dienyl, norbornylenyl, piperidyl, pyrrolidinyl, piperazinyl, morpholinyl, thiomorpholinyl, thiazolidinyl, 1,4-dioxanyl, tetrahydrofuranyl, tetrahydrothiophenyl, lactam or lactone. Cyclic groups may be optionally substituted.

In one embodiment of the second or fifth aspects, the change in fluorescence may occur when the binding of protein to ligand displaces the fluorescent molecular rotor(s) from the ligand or perturbs the fluorescent molecular rotor(s).

In another embodiment of the second or fifth aspects, the change in fluorescence may occur when the binding of protein to ligand displaces the fluorescent molecular rotor(s) from the protein or perturbs the fluorescent molecular rotor(s).

The ligand of the second or fifth aspects may be a molecule that binds to protein. Accordingly, a ligand may be a small molecule, nucleic acid such as RNA or DNA, a polynucleoside or peptide. "Peptide" may refer to a peptide, dipeptide or polypeptide. A ligand variant peptide may be substantially identical to a native peptide sequence. The amino acid sequence of the variant at times is 50%, 55%, 60%, 65%, 70%, 75%, 80%, 85%, 89%, 90%, 91%, 92%, 93%, 94%, 95%, 96%, 97%, 98%, 99%, or more identical to a native peptide sequence. In one embodiment, the ligand may be a binding peptide derived from p53 protein. In another embodiment, the ligand may be a peptide selected from JP1: MPRFMDYWEGLSK or JP2: MPRFMDYWEGLNK.

In another embodiment of the second or fifth aspects, the ligand may be DNA.

In yet another embodiment of the second or fifth aspects, the ligand may be a small molecule. The small molecule may be peptidomimetics (e.g., peptoids), amino acids, amino acid analogs, polynucleotides, polynucleotide analogs, nucleotides, nucleotide analogs, organic or inorganic compounds (i.e., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. The small molecule may be biotin.

The protein of the second or fifth aspects may contain a region that interacts with a ligand. The protein may be a DNA transacting protein that a DNA molecule having a particular sequence binds to. The DNA transacting protein may be a transcription factor, polymerase, telomerase or recombinase. The protein may be wild-type or mutant p53.

In another embodiment of the second or fifth aspects, the protein may be wild-type or mutant MDM2. The wild-type or mutant MDM2 may bind to a binding peptide derived from p53 protein. The interaction between MDM2 and the binding peptide may be mapped to the N-terminal domain of MDM2 (residues 1-100) and the N-terminal domain of p53 (residues 18-26).

In yet another embodiment of the second or fifth aspects, the protein may be streptavidin.

There is further provided a screening assay according to an eight aspect for identifying an interaction between a protein and ligand, the assay comprising:
a) providing a protein to be tested for binding affinity with a candidate ligand;
b) providing candidate ligands bound to at least one fluorescent molecular rotor;
c) testing the candidate ligands for binding affinity by contacting said protein with said candidate ligands bound to at least one fluorescent molecular rotor; and
d) identifying a relevant interaction by measuring a change in fluorescence emitted by the fluorescent molecular rotor(s), wherein the fluorescent molecular rotor is selected from the group consisting of:

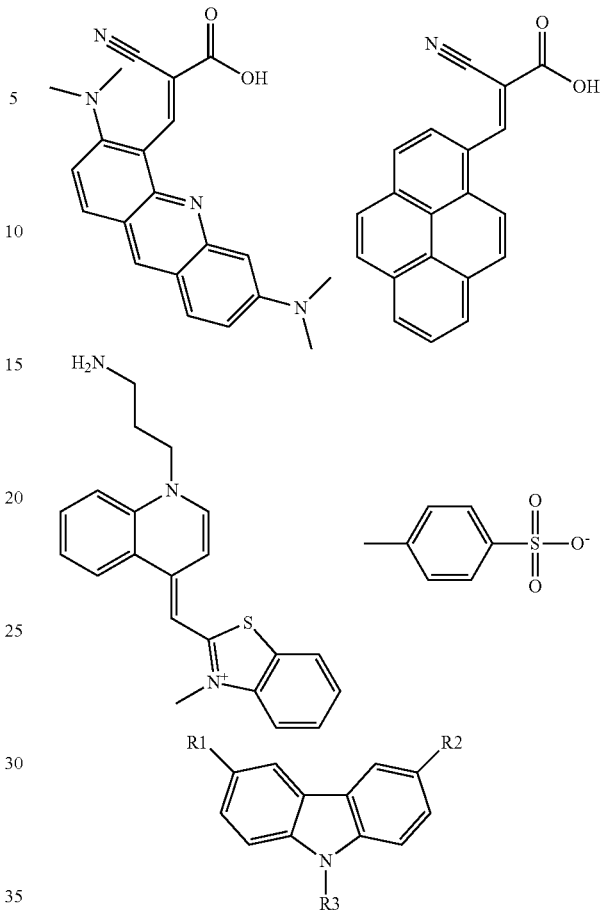

wherein at least one of R1, R2 or R3 is

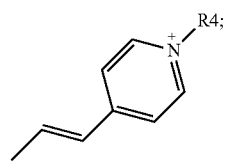

and R1, R2, R3 and R4 are independently chosen from the group consisting of: optionally substituted alkyl, optionally substituted alkenyl, optionally substituted alkynyl, optionally substituted aryl, optionally substituted heteroaryl, optionally substituted cycloalkyl or optionally substituted heterocyclyl.

There is also provided a kit according to an twelfth aspect for carrying out the disclosed method or the disclosed screening assay comprising the ligand, protein and fluorescent molecular rotor(s), and a means to detect a change in fluorescence.

There is further provided a method according to a third aspect for detecting an interaction between (a) DNA and protein, (b) MDM2 protein and a peptide, or (c) biotin and streptavidin, the method comprising:
(i) binding at least one fluorescent molecular rotor to DNA or protein of (a), peptide or MDM2 protein of (b), or biotin or streptavidin of (c); and
(ii) detecting a change in fluorescence emitted by said fluorescent molecular rotor after contact of the bound fluorescent molecular rotor with the other of said DNA or protein of (a), peptide or MDM2 protein of (b), or biotin and streptavidin of (c), thereby detecting an interaction between DNA and protein of (a), peptide and MDM2 protein of (b), or biotin or streptavidin of (c);

wherein the fluorescent molecular rotor is selected from the group consisting of:
- a rotating σ-bond;
- an electron-donating moiety;
- an electron-accepting moiety; and
- a π-conjugated linker.

In the method for detecting an interaction between (a) DNA and protein (b) MDM2 protein and a peptide, or (c) biotin and streptavidin, according to a third aspect, the fluorescent molecular rotor(s) may exhibit a change in fluorescence when the DNA of (a), peptide of (b), or biotin of (c), binds to the protein of (a), MDM2 protein of (b) or streptavidin of (c), respectively.

There is also provided a composition comprising:
a) fluorescent molecular rotor, DNA and protein;
b) fluorescent molecular rotor, peptide and MDM2 protein, or
c) fluorescent molecular rotor, biotin and streptavidin,
wherein said fluorescent molecular rotor is bound to one of DNA or protein in (a), one of peptide or MDM2 protein in (b), or one of biotin or streptavidin in (c),
and wherein the fluorescent molecular rotor(s) comprises:
- a rotating σ-bond;
- an electron-donating moiety;
- an electron-accepting moiety; and
- a π-conjugated linker.

The fluorescent molecular rotor(s) of the third or sixth aspects may be bound to DNA or protein of (a), peptide or MDM2 protein of (b), or biotin or streptavidin of (c), via a linking moiety.

In one embodiment of the third or sixth aspects, the fluorescent molecular motor(s) may be bound via a linking moiety to the DNA of (a), peptide of (b), or biotin of (c).

In another embodiment of the third or sixth aspects, the fluorescent molecular motor(s) may be bound via a linking moiety to the protein of (a), MDM2 protein of (b), or streptavidin of (c).

The linking moiety of the third or sixth aspects may comprise 1 to 20 main chain atoms, 1 to 15 main chain atoms, 1 to 10 main chain atoms, or 1 to 5 main chain atoms.

The linking of the third or sixth aspects may be a single bond or optionally substituted heteroalkyl. Said heteroalkyl may be optionally substituted heteroalkyl selected from ethers, thioethers, amines, hydroxymethyl, 3-hydroxypropyl, 1,2-dihydroxyethyl, 2-methoxyethyl, 2-aminoethyl, 2-dimethylaminoethyl, alkoxyalkylamines, alkoxyalkylamides, aminoheteroalkyl substituted with oxo or aminoalkyls. The linking moiety may be:

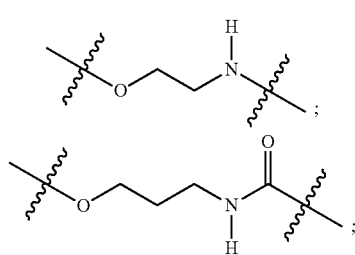

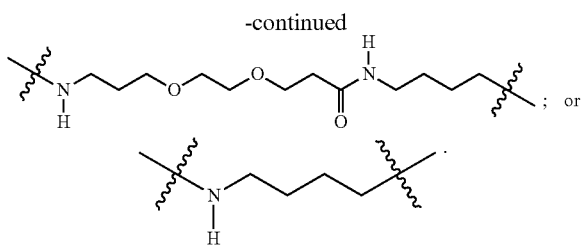

The optionally substituted heteroalkyl may be optionally interrupted by one or more optionally substituted cyclic groups. Said cyclic groups may be aryl, heteroaryl, cycloalkyl, cycloalkenyl or heterocycle. Cyclic groups may be selected from phenyl, biphenyl, naphthyl, phenanthrenyl, cyclopropyl, cyclopentyl, cyclohexyl, cycloheptyl, 1-decalinyl, norbornyl, adamantyl, cyclopentenyl, cyclohexenyl, cyclohepta-1,3-dienyl, norbornylenyl, piperidyl, pyrrolidinyl, piperazinyl, morpholinyl, thiomorpholinyl, thiazolidinyl, 1,4-dioxanyl, tetrahydrofuranyl, tetrahydrothiophenyl, lactam or lactone. Cyclic groups may be optionally substituted.

In one embodiment of the third or sixth aspects, the change in fluorescence may occur when the binding of protein to DNA of (a), MDM2 protein to peptide of (b), or streptavidin to biotin of (c), displaces the fluorescent molecular rotor(s) from the DNA or (a), peptide of (b), or biotin of (c), or perturbs the fluorescent molecular rotor(s).

In another embodiment of the third or sixth aspects, the change in fluorescence may occur when the binding of protein to DNA of (a), MDM2 protein to peptide of (b), or biotin to streptavidin, displaces the fluorescent molecular rotor(s) from the protein of (a), MDM2 protein of (b), or streptavidin of (c), or perturbs the fluorescent molecular rotor(s).

In one embodiment of the third or sixth aspects, the peptide of (b) may be a binding peptide derived from p53 protein. In another embodiment, the ligand may be a peptide selected from JP1: MPRFMDYWEGLSK or JP2: MPRFMDYWEGLNK.

The protein of (a) of the third or sixth aspects may contain a region that interacts with DNA. The protein may be a DNA transacting protein that a DNA molecule having a particular sequence binds to. The DNA transacting protein may be a transcription factor, polymerase, telomerase or recombinase. The protein may be p53 protein. The protein may be wild-type or mutant p53 protein.

In another embodiment of the third or sixth aspects, the protein of (b) may be MDM2 protein. The protein may be wild-type or mutant MDM2. The MDM2 protein may bind to a binding peptide derived from p53 protein. The interaction between MDM2 and the binding peptide may be mapped to the N-terminal domain of MDM2 (residues 1-100) and the N-terminal domain of p53 (residues 18-26).

There is further provided a screening assay according to a ninth aspect for identifying an interaction between DNA and protein, or peptide and MDM2, the assay comprising:
a) providing a protein to be tested for binding affinity with a candidate DNA or peptide;
b) providing DNA or peptide bound to at least one fluorescent molecular rotor;
c) testing the candidate DNA or peptide for binding affinity by contacting said protein with said candidate ligands bound to at least one fluorescent molecular rotor; and d) identifying a relevant interaction by measuring a change in fluorescence emitted by the fluorescent molecular rotor(s), wherein the fluorescent molecular rotor(s) comprises:

a rotating σ-bond;

an electron-donating moiety;

an electron-accepting moiety; and a π-conjugated linker.

There is also provided a screening assay according to a tenth aspect for identifying a candidate compound, comprising:

(a) providing a candidate compound to be tested for binding affinity with protein;

(b) providing a complex comprising a probe bound to protein, wherein said probe comprises at least one fluorescent molecular rotor bound to peptide;

(c) testing the candidate compound for binding affinity with said protein by contacting said candidate compound with said complex; and (d) identifying a relevant candidate compound by measuring the change in fluorescence emitted when said complex is disrupted, wherein the fluorescent molecular rotor(s) comprises:

a rotating σ-bond;

an electron-donating moiety;

an electron-accepting moiety; and a π-conjugated linker.

In one embodiment, the change in fluorescence occurs when the probe is displaced from the complex.

In a further embodiment, the probe comprises peptide selected from the group consisting of JP1: MPRFMDYWEGLSK (SEQ ID NO:1) and JP2: MPRFMDYWEGLNK (SEQ ID NO:2). The protein may be MDM2 protein.

In one embodiment of the tenth aspect, the fluorescent molecular rotor, in its unbound state, is selected from the group consisting of:

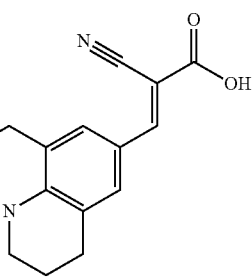

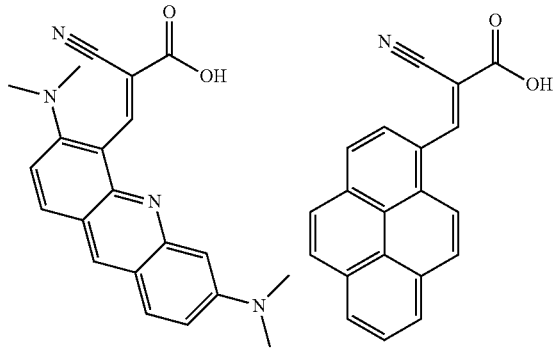

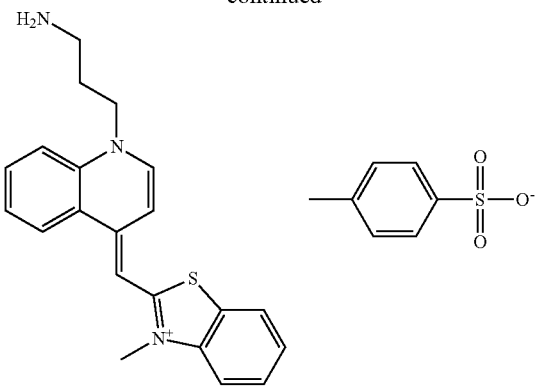

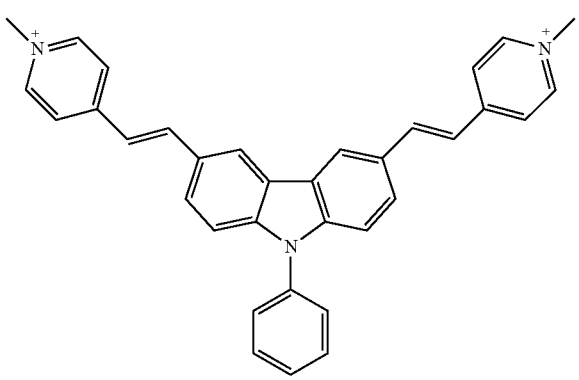

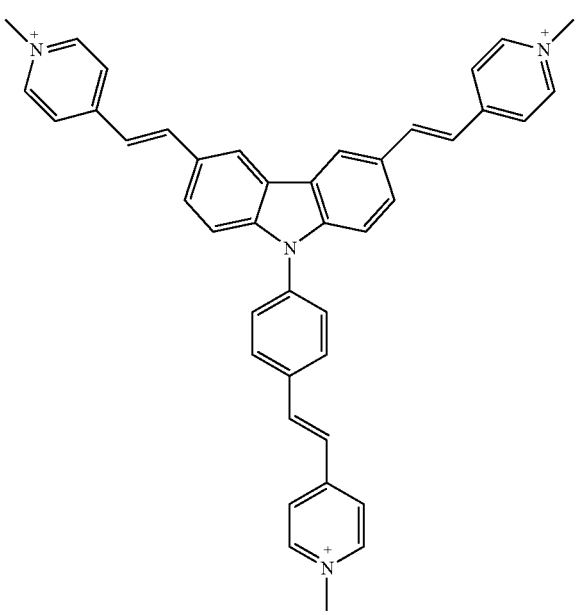

There is also provided a kit according to a twelfth aspect for carrying out the disclosed method according to a third aspect or the disclosed screening assay according to the ninth or tenth aspects, comprising the ligand, protein and fluorescent molecular rotor(s), and a means to detect a change in fluorescence.

There is further provided a chemical compound selected from the group consisting of:

(i) 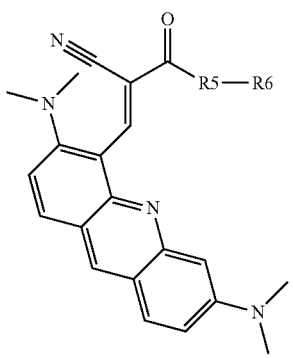

(ii) 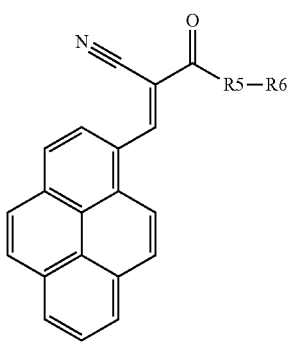

(iii) 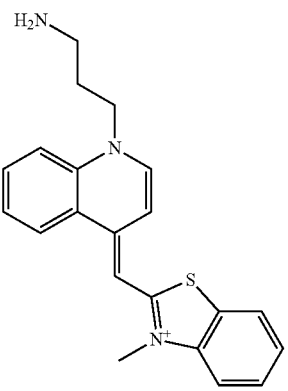

(iv) 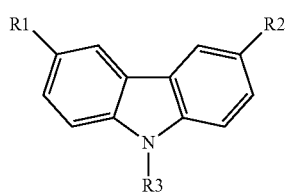

(v) 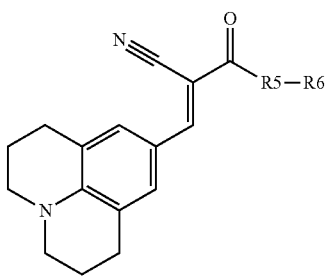

wherein at least one of R1, R2 or R3 is

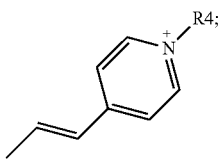

R1, R2, R3 and R4 are independently chosen from the group consisting of: optionally substituted alkyl, optionally substituted alkenyl, optionally substituted alkynyl, optionally substituted aryl, optionally substituted heteroaryl, optionally substituted cycloalkyl or optionally substituted heterocyclyl;

R5 is a OH or a linking moiety selected from the group consisting of a single bond; or optionally substituted heteroalkyl, wherein the main chain atoms of said optionally substituted heteroalkyl are optionally interrupted by one or more optionally substituted cyclic groups; and R6 is absent or a ligand, with the proviso that R5 is not OH in formula (v).

In a compound of formulas (i) or (ii), R5 may be OH or a linking moiety. R5 may be a linking moiety selected from optionally substituted heteroalkyl. Said heteroalkyl may be optionally substituted heteroalkyl selected from ethers, thioethers, amines, hydroxymethyl, 3-hydroxypropyl, 1,2-dihydroxyethyl, 2-methoxyethyl, 2-aminoethyl, 2-dimethylaminoethyl, alkoxyalkylamines, alkoxyalkylamides, aminoheteroalkyl substituted with oxo or aminoalkyls. The optionally substituted aminoalkyl may be:

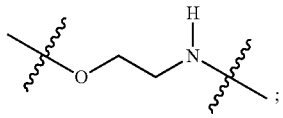

In a compound of formulas (i) or (ii), R6 may be H or absent. When R5 is OH, R6 may be absent. When R5 is a linking moiety, R6 may be a ligand.

A compound of formula (i) may be selected from:

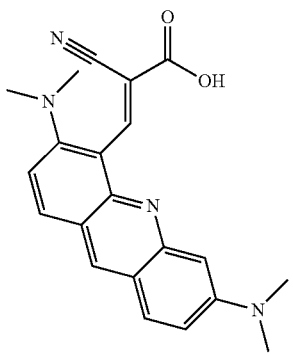

A compound of formula (ii) may be selected from:

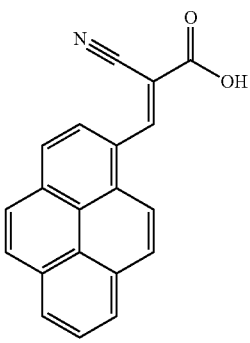

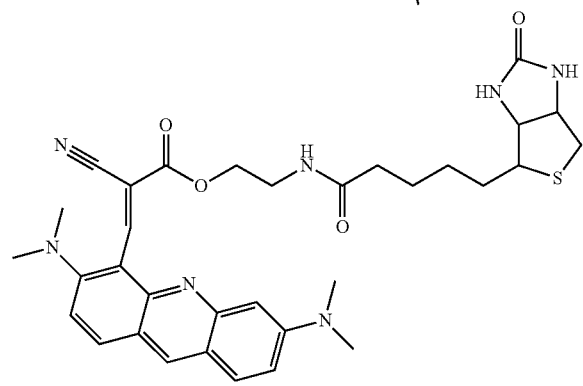

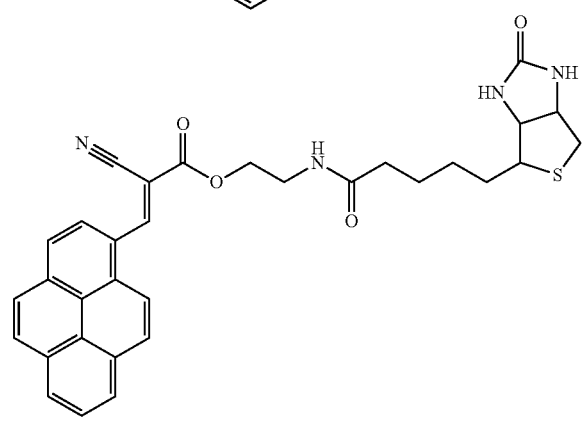

In the compound of formula (iv), R4 may be optionally substituted alkyl, optionally substituted alkenyl, optionally substituted alkynyl, optionally substituted aryl, optionally substituted heteroaryl, optionally substituted cycloalkyl or optionally substituted heterocyclyl. R4 may be alkyl selected from $C_1$-$C_6$ alkyl, such as methyl, ethyl, propyl, butyl, pentyl or hexyl. R4 may be methyl.

In the compound of formula (iv), R1 may be optionally substituted alkyl, optionally substituted alkenyl, optionally substituted alkynyl, optionally substituted aryl, optionally substituted heteroaryl, optionally substituted cycloalkyl or optionally substituted heterocyclyl. R1 may be substituted alkenyl selected from substituted $C_2$-$C_6$ alkenyl, such as substituted ethenyl, substituted propenyl, substituted butenyl, substituted pentenyl or substituted hexenyl. Said substituted alkenyl may be alkenyl substituted with optionally substituted heteroaryl selected from optionally substituted pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinylsubstituted quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl or benzothiazolyl. R1 may be

In the compound of formula (iv), R2 may be optionally substituted alkyl, optionally substituted alkenyl, optionally substituted alkynyl, optionally substituted aryl, optionally substituted heteroaryl, optionally substituted cycloalkyl or optionally substituted heterocyclyl. R2 may be substituted alkenyl selected from substituted $C_2$-$C_6$ alkenyl, such as substituted ethenyl, substituted propenyl, substituted butenyl, substituted pentenyl or substituted hexenyl. Said substituted alkenyl may be alkenyl substituted with optionally substituted heteroaryl selected from optionally substituted pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinylsubstituted quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl or benzothiazolyl. R2 may be

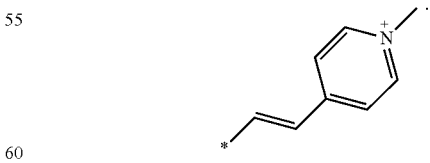

In the compound of formula (iv), R3 may be optionally substituted alkyl, optionally substituted alkenyl, optionally substituted alkynyl, optionally substituted aryl, optionally substituted heteroaryl, optionally substituted cycloalkyl or optionally substituted heterocyclyl. R3 may be phenyl. R3 may be substituted phenyl. Said substituted phenyl may be phenyl substituted with substituted alkenyl selected from substituted $C_2$-$C_6$ alkenyl, such as substituted ethenyl, substituted propenyl, substituted butenyl, substituted pentenyl or substituted hexenyl. Said substituted alkenyl may be alkenyl substituted with optionally substituted heteroaryl selected from optionally substituted pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinylsubstituted quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl or benzothiazolyl. R3 may be

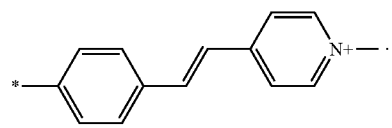 [SMILES: *c1ccc(/C=C/c2cc[n+](C)cc2)cc1]

A compound of formula (iv) may be:

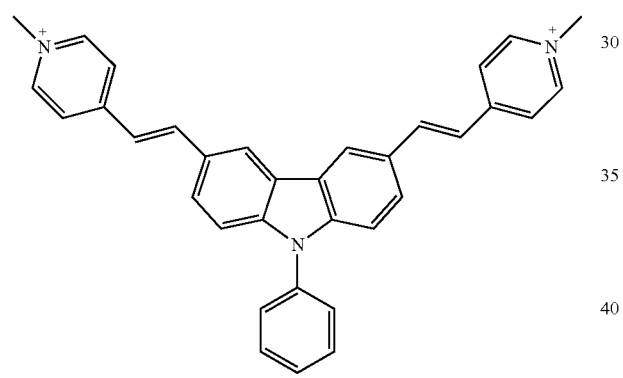

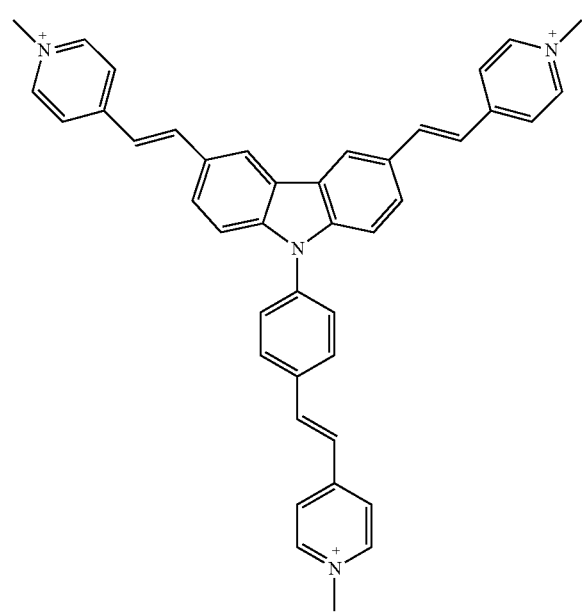

In a compound of formula (v), R5 may be a linking moiety. R5 may be a linking moiety selected from optionally substituted heteroalkyl. Said heteroalkyl may be optionally substituted heteroalkyl selected from ethers, thioethers, amines, hydroxymethyl, 3-hydroxypropyl, 1,2-dihydroxyethyl, 2-methoxyethyl, 2-aminoethyl, 2-dimethylaminoethyl, alkoxyalkylamines, alkoxyalkylamides, aminoheteroalkyl substituted with oxo or aminoalkyls. The optionally substituted aminoalkyl may be:

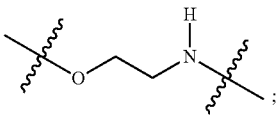

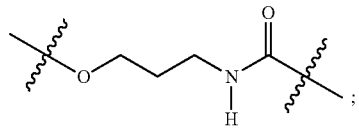

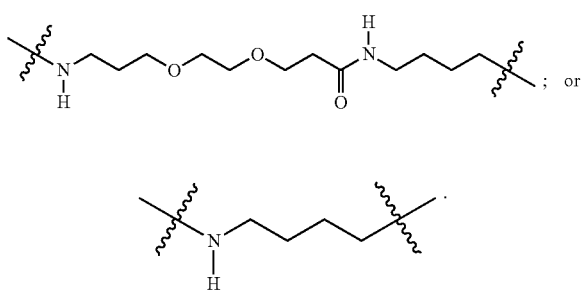

In a compound of formula (v), R6 may absent or a ligand. The ligand may be a molecule that binds to protein. Accordingly, a ligand may be a small molecule, nucleic acid such as RNA or DNA, a polynucleoside or peptide. "Peptide" may refer to a peptide, dipeptide or polypeptide. A ligand variant peptide may be substantially identical to a native peptide sequence. The amino acid sequence of the variant at times is 50%, 55%, 60%, 65%, 70%, 75%, 80%, 85%, 89%, 90%, 91%, 92%, 93%, 94%, 95%, 96%, 97%, 98%, 99%, or more identical to a native peptide sequence. In one embodiment, the ligand may be a binding peptide derived from p53 protein. In another embodiment, the ligand may be a peptide selected from JP1: MPRFMDYWEGLSK or JP2: MPRFMDYWEGLNK. The ligand may be DNA. The ligand may be a small molecule. The small molecule may be peptidomimetics (e.g., peptoids), amino acids, amino acid analogs, polynucleotides, polynucleotide analogs, nucleotides, nucleotide analogs, organic or inorganic compounds (i.e., including heterorganic and organometallic compounds) having a molecular weight less than about 10,000 grams per mole, organic or inorganic compounds having a molecular weight-less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. The ligand may be biotin.

A compound of formula (v) may be:
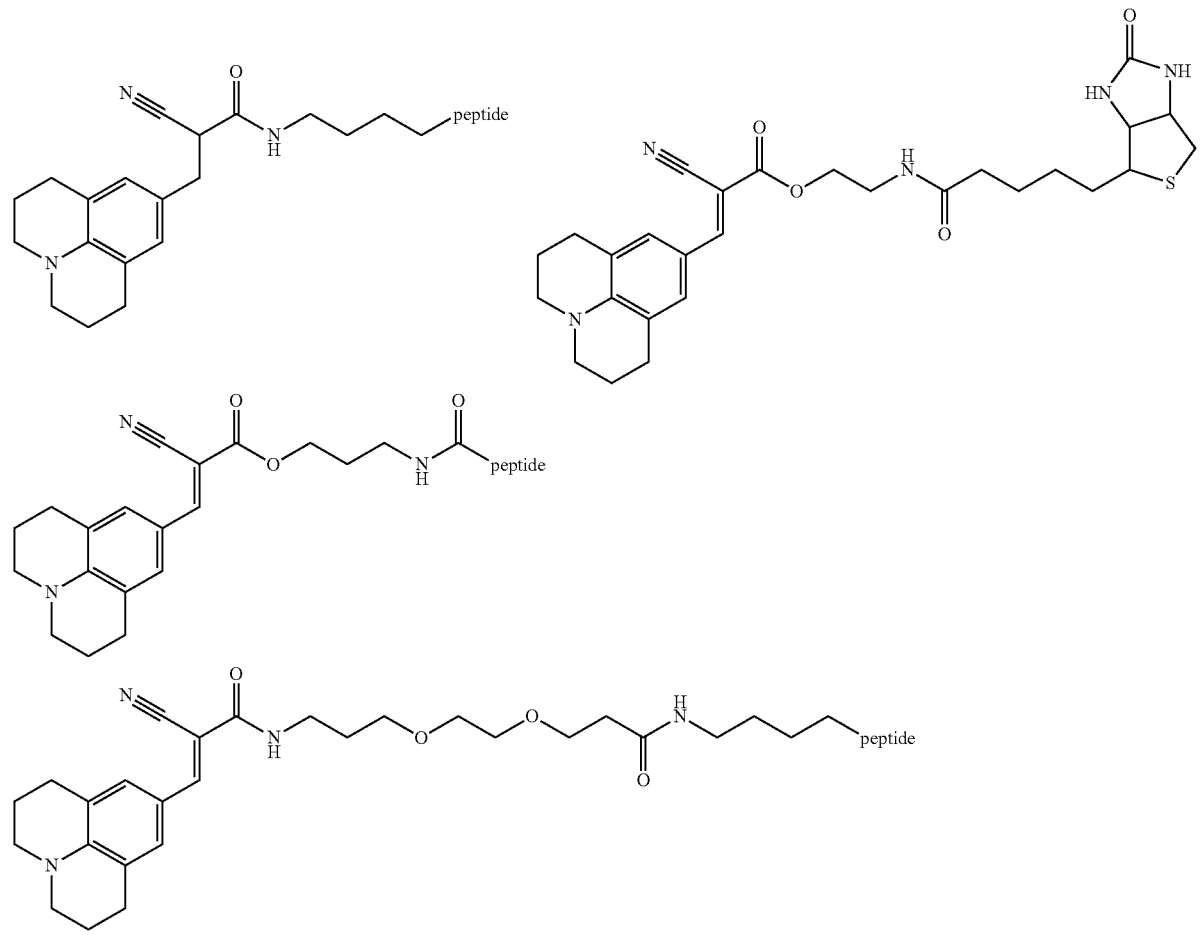
(SEQ ID NO: 1)
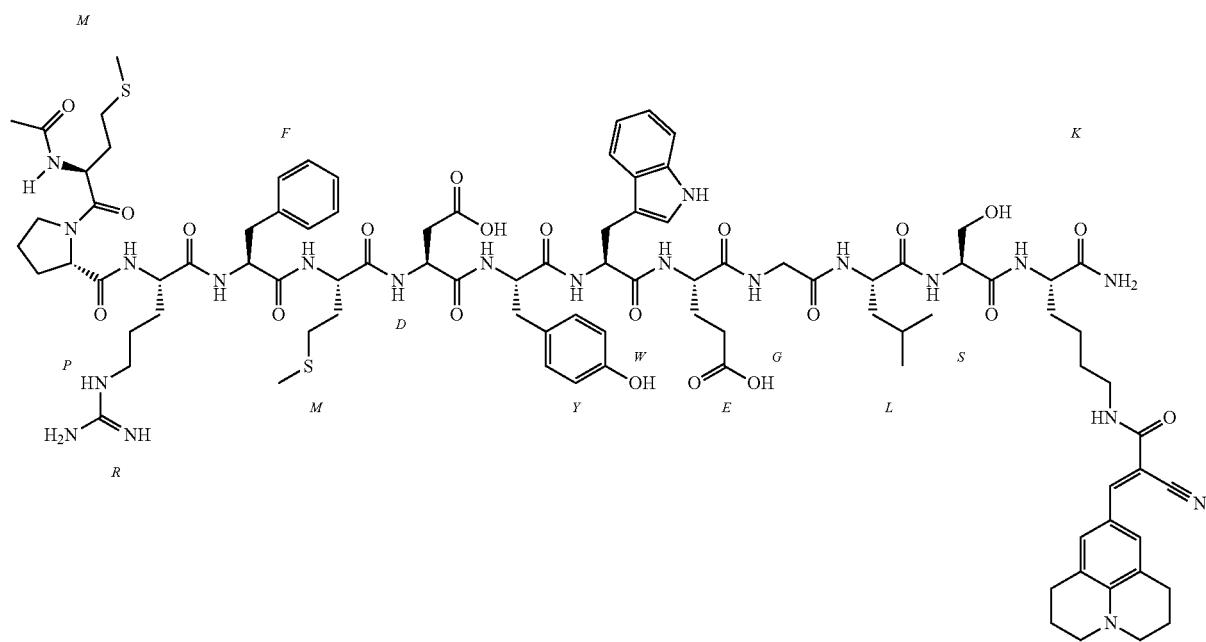

(SEQ ID NO: 2)

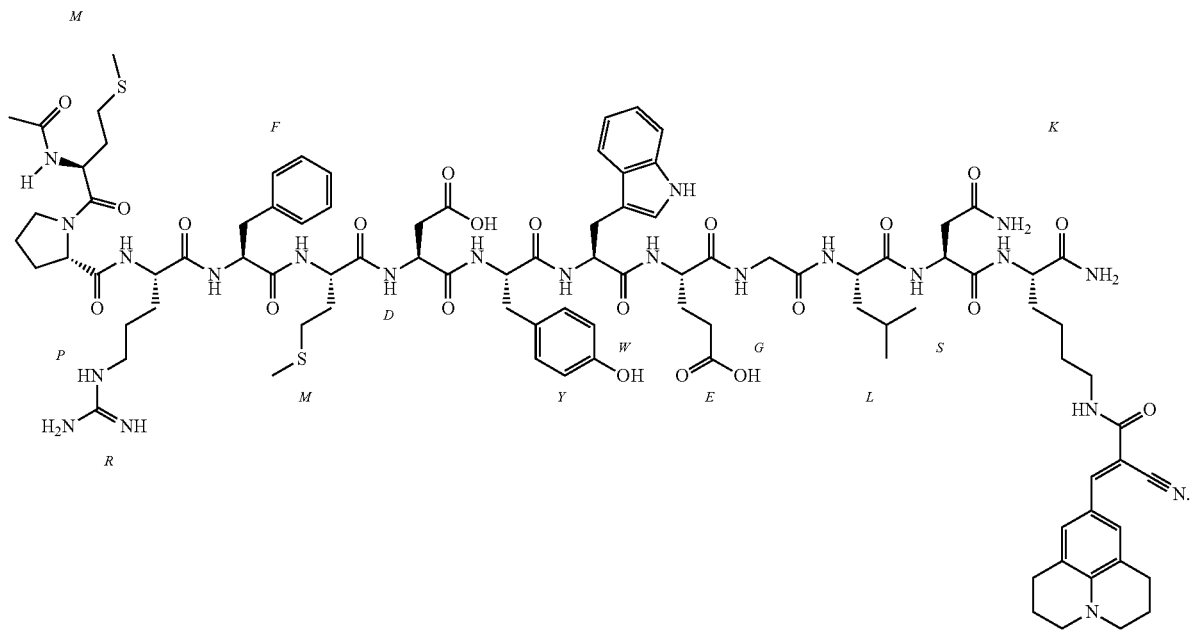

In a further embodiment of the first to fourteenth aspects, fluorescent molecular rotor(s) may be further modified to tune their electronic properties. An amino electron donor group may be replaced with a weaker electron donor results in a blue shift in both the excitation and emission maxima. The conjugation length of the linker moiety may be lengthened, resulting in longer the emission wavelength and a larger Stokes shift. The replacement of a nitrile electron acceptor moiety with methyl ester or phenyl sulfonyl will result in an increase in the emission quantum yield due to the stabilization of the excited state brought about by the change in dipole moment.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIGS. 3a to 3c show that fluorescent molecular rotors of the present invention display an increase in fluorescence upon increase in viscosity. % indicate % of glycerol in ethylene glycol. Viscosity of glycerol>ethylene glycol. Experiments were performed with rotors at a concentration of 100 μM.

FIG. 3a depicts a viscosity experiment with julolidine-based molecular rotor.

FIG. 3b depicts a viscosity experiment with a pyrene-based fluorescent molecular rotor.

FIG. 3c depicts a viscosity experiment with acridine-based, thiazole orange-based and carbazole-based fluorescent molecular rotors.

FIG. 4a depicts the emission spectra of a CCVJ molecular rotor bound to biotin with Streptavidin. Fluorescence increase upon addition of streptavidin to biotin conjugated with CCVJ. 40 μM of rotor-biotin conjugate was incubated for 15 min with 50 μg of streptavidin. Fluorescence emission spectrum was measured using an excitation wavelength ($\lambda_{ex}$) of 433 nm.

FIG. 4b depicts the emission spectra of a pyrene-based fluorescent molecular rotor bound to biotin with Streptavidin.

EXAMPLES

Figure 1A:
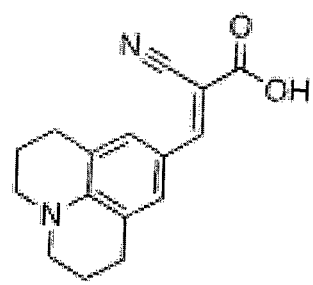
FIG. 1a shows a julodine-based fluorescent molecular rotor, 9-(2-carboxy-2-cyanovinyl) julolidine (CCVJ), corresponding to a disclosed formula (v).
Figure 1B:
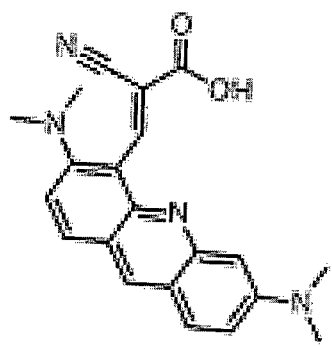
FIG. 1b shows an acridine-based fluorescent molecular rotor corresponding to a disclosed formula (i).
Figure 1C:
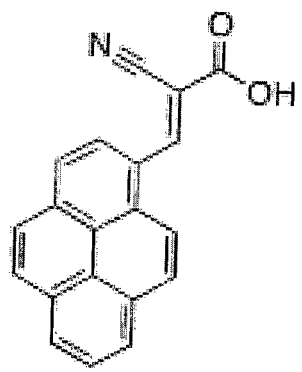
FIG. 1c shows a pyrene-based fluorescent molecular rotor corresponding to a disclosed formula (ii).
Figure 1D:
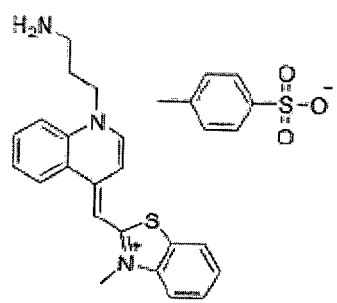
FIG. 1d shows a thiazole-based fluorescent molecular rotor corresponding to a disclosed formula (iii).
Figure 1E:
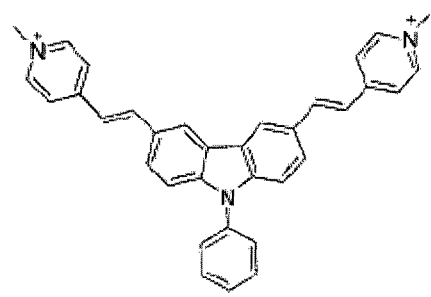
FIG. 1e shows a carbazole-based (2-arm) fluorescent molecular rotor corresponding to a disclosed formula (iv).
Figure 1F:
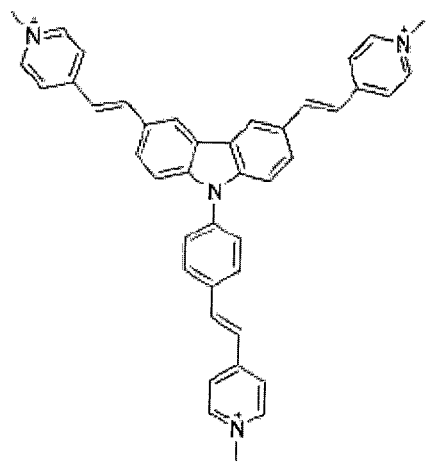
FIG. 1f shows a carbazole-based (3-arm) fluorescent molecular rotor corresponding to a disclosed formula (iv).
Figure 2:
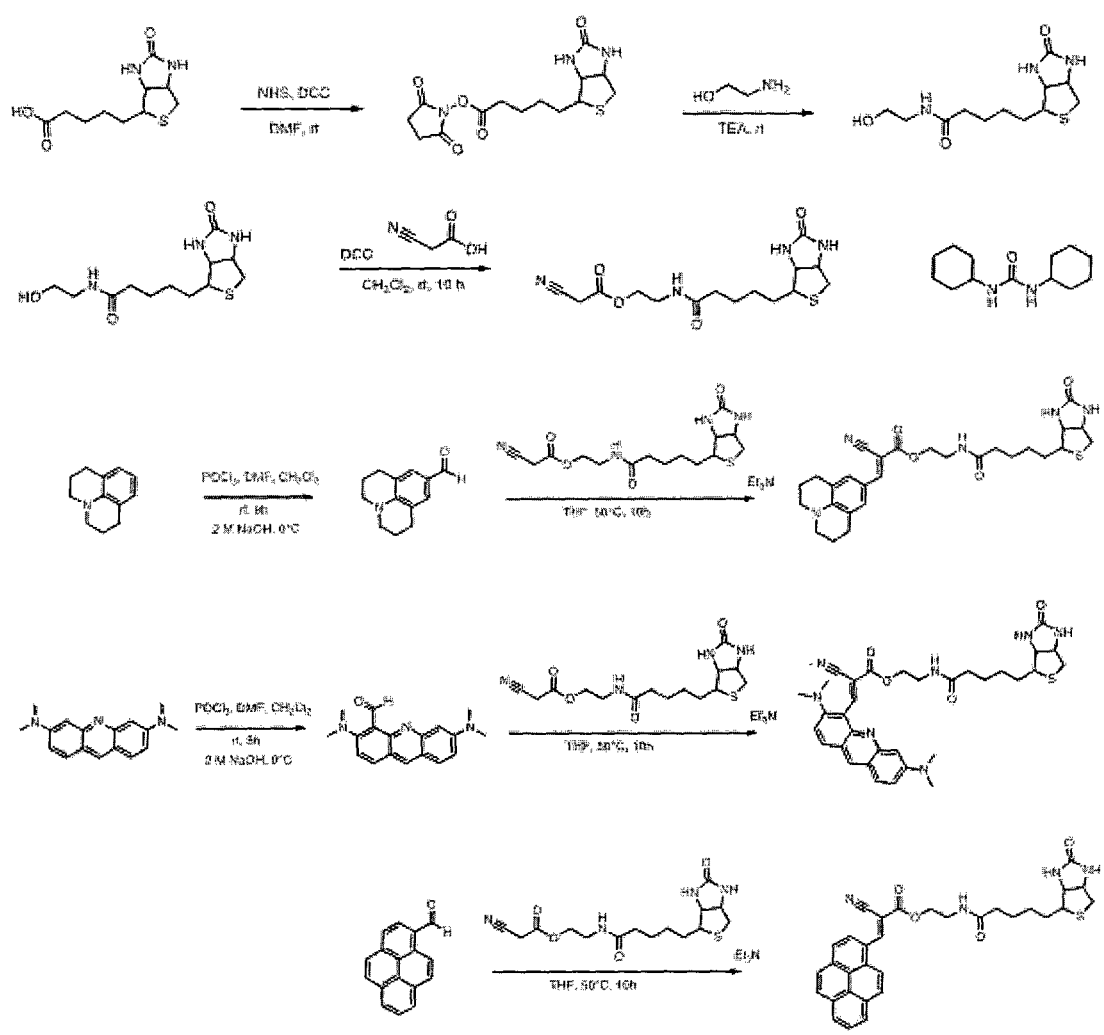
FIG. 2 shows a schematic diagram for the synthesis of fluorescent molecular rotors conjugated with biotin.
Figure 3A:
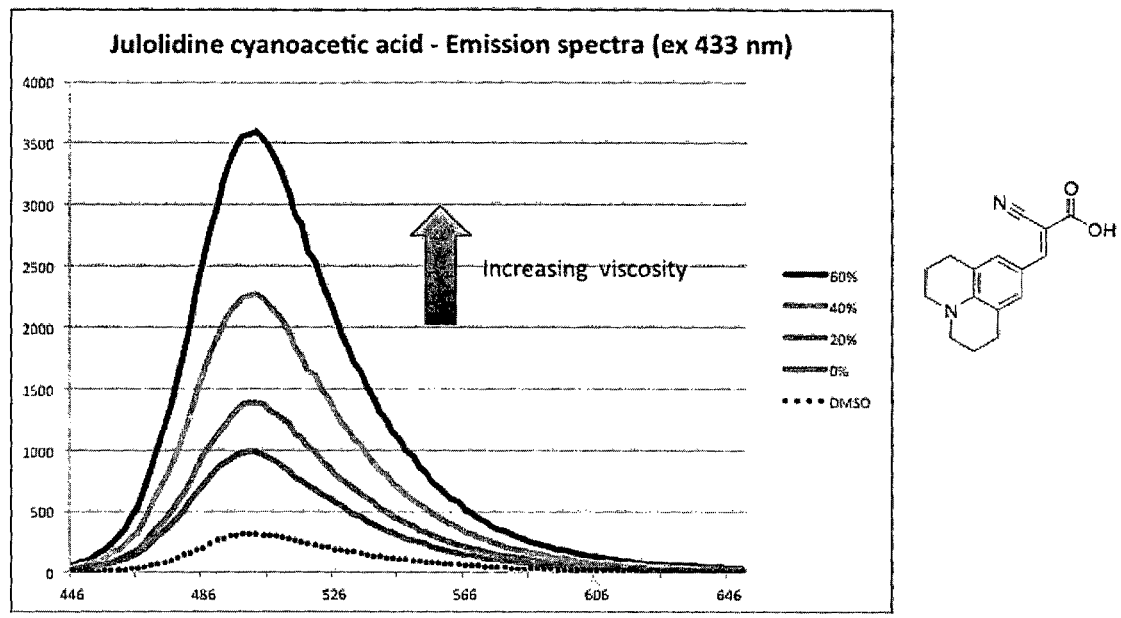
Figure 3A:
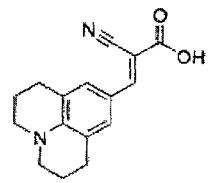
Figure 3B:
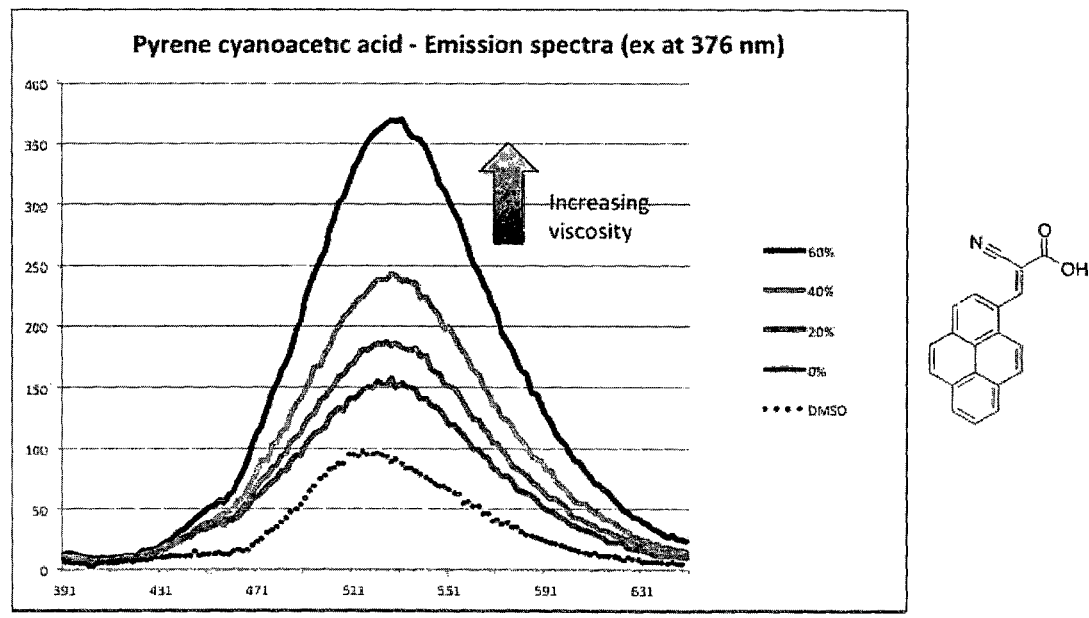
Figure 3B:
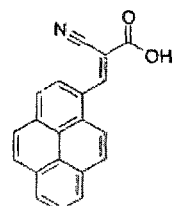

Non-limiting examples of the invention will be further described in greater detail by reference to specific Examples, which should not be construed as in any way limiting the scope of the invention.

Materials and Methods
HPLC Purification

All HPLC runs were carried out using an Agilent 1260 infinity and C18 semi-prep column. Solvent eluant systems are of water (+0.065% TFA) and acetonitrile (+0.05% TFA), from 5%-65% in 35 mins. Fractions were then dried and dissolved in water/ACN (1:1). Concentration of samples was obtained through NanoDrop 2000C spectrophotometer absorbance.

Expression and Purification of MDM2

Hexahistidine-MDM2 recombinant protein (residues 18-125) was purified. Briefly, cDNA encoding residues 18-125 of MDM2 was cloned into pET19b (Novagen), transformed into *E. coli* BL21 (DE3) and induced with 1 mM IPTG. Bacterial cells were then disrupted and first purified using a Ni-nitrilotriacetic acid (NTA) column (eluted with a 1M imidazole gradient), followed by cation-exchange chromatography (eluted using a 1M NaCl gradient).

Determination of Dissociation Constant

The dissociation constants for rotor-peptide conjugates binding to MDM2 (18-125) were determined by titrating JP1-R, or JP2-R, against 100 nM of recombinant MDM2 protein, and fitting experimental data (after subtracting background fluorescence of unbound rotor-peptide conjugates) to the following 1:1 binding model (equation 1)[2] where [P] is the MDM2 protein concentration, $[L_R]$ is the concentration of the reporter ligand (rotor-peptide conjugate), $K_{dR}$ is the dissociation constant. f is the fluorescence signal measured, $f_0$ is the fluorescence of free unbound rotor-peptide conjugate, $f_b$ is the fluorescence of bound JP-R/MDM2 complex.

$$f = f_0 + (f_b - f_0) \times \frac{(K_{dR} + [L_R] + [P]) - \sqrt{(K_{dR} + [L_R] + [P])^2 - 4[L_R][P]}}{2[L_R]} \quad \text{Equation 1}$$

The determined apparent dissociation constant of JP1-R binding to MDM2 ($K_{dR}$=16.01±7.52) was later used to determine the apparent $K_d$s, using competitive binding experiments, of several known MDM2-p53 inhibitor molecules (Racemic Nutlin, Nutlin-3b and sMTide-02). Inhibitor molecules were titrated against a fixed concentration of JP1-R (80 nM) and MDM2 (200 nM) in triplicates and the resulting data points were fitted to equations 2-6[2, 3] where $[L_c]$ and $[L_R]$ denote concentrations of competitive ligand (inhibitor molecules) and reporter ligand (JP1-R), respectively, and $K_{dC}$ is the dissociation constant of the competitive molecule.

$$f = f_0 + (f_b - f_0) \times \frac{2\sqrt{(d^2 - 3e)} \cos\left(\frac{\theta}{3}\right) - d}{3K_{dR} + 2\sqrt{(d^2 - 3e)} \cos\left(\frac{\theta}{3}\right) - d} \quad \text{Equation 2}$$

$$d = K_{dR} + K_{dC} + [L_C] + [L_R] - [P] \quad \text{Equation 3}$$

$$e = ([L_R] - [P])K_{dR} + ([L_C] - [P])K_{dC} + K_{dR}K_{dC} \quad \text{Equation 4}$$

$$g = -K_{dR}K_{dC}[P] \quad \text{Equation 5}$$

$$\theta = \cos^{-1}\left[\frac{-2d^3 + 9de - 27g}{2\sqrt{(d^2 - 3e)^3}}\right] \quad \text{Equation 6}$$

Curve fitting and calculations for respective $K_d$ values were performed using the software Prism 5.03 (Graphpad).

Fragment Library Screen with Rotor-Peptide Probe, JP1-R

Unless otherwise stated, binding reactions involving rotor-peptide conjugates were all performed using black 96-well polypropylene plates (Corning), in a PBS reaction buffer solution containing 0.005% Tween-20 (v/v). For reactions involving Zenobia fragment library compounds, 10% DMSO was added to increase solubility of compounds. Fluorescence activity was measured using the EnVision Multilabel reader (Perkin Elmer) at 435/505 (ex/em) nm.

A small-fragment library (Zenobia Therapeutics) was sampled in our compound screen using JP1-R. The library consists of 352 fragment molecules with decorated-ring structures and an average molecular weight of 154.2 Da. The screen was performed by first aliquoting a pre-made mixture containing 80 nM JP1-R and 200 nM MDM2 (18-125) onto a 96-well plate, and allowing it to equilibrate to room temperature (15 min) before a first reference reading was measured. Next, 500 µM of each fragment compound was added into the JP1-R/MDM2 reaction mixture, and incubated for another 30 min before a second measurement was taken. The final result was interpreted as a percentage change of the second measurement from the first reference measurement, of which a decrease in fluorescence would indicate a positive hit (from displacing JP1-R off MDM2). The displacement threshold was set, for this study, at 20% reduction from the reference fluorescence value.

Fluorescence Polarization Assay

Fluorescence polarization was performed as previously described, except in a reaction buffer containing PBS, 10% DMSO (v/v), 0.005% Tween-20 (v/v). Briefly, a mixture containing 50 nM of FAM-labeled 12.1 peptide (RFMDY- WEGLNK) and 250 nM of recombinant MDM2 was constituted before adding 500 µM of respective fragment library compound. The reactions were then incubated at room temperature for 30 min before measuring on the EnVision plate reader (Perkin Elmer).

Pull-Down Assay and Western Blotting 650 ng of MDM2 (18-125) recombinant protein was first incubated with either 500 µM of the respective fragment compound, 100 µM Nutlin, or DMSO (in a reaction buffer containing PBS, 10% DMSO (v/v), 0.005% Tween-20 (v/v), 0.2% BSA (w/v) for 15 min at room temperature before adding to 5 µL of IVT-translated p53 protein for another 30 min. p53 protein was synthesized using the PURESYSTEM (NEB) in-vitro transcription/translation kit as previously described, but reconstituted with 6× binding buffer (150 mM NaPi, pH 7.2, 600 mM NaCl, 24 mM DTT) upon completion of IVT reaction. To capture the MDM2/p53 complex, pre-blocked (2% BSA/PBS for 2 hours at room temperature) Dynabeads® His-Tag Isolation & Pulldown (Life Technologies) beads were added to the compound/MDM2/IVTp53 mixture and rotated at room temperature for 15 min. After which, beads were washed 4× with wash buffer (PBS, 0.1% BSA (w/v), 0.1% Tween-20 (v/v), 5 mM imidazole), once with PBS (15s vortex at 1600 r.p.m. on MS2 minishaker, IKA) and eluted with 25 µL LDS at 95° C. for 7 min. Western blotting of the pull-down eluates were performed as previously described, and probed with either DO-1 (anti-p53) or 4B1 (anti-MDM2) primary antibodies.

Molecular Modeling Studies a) Molecular Dynamics Simulations

The initial structure of MDM2-peptide complex was taken from the crystal structure of high affinity peptide bound to MDM2 (PDB code 3EQS, resolved at 1.7 Å). Peptides were modeled using Modeller[7] was used to model the peptides using PMI peptide as template. The structure used included residues 25-109 of the N-terminal domain of human MDM2 and residues 1-13 of the peptides JP1-R ([1]MPRFMDYWEGLSK[13]-rotor) and JP2-R ([1]MPRFMDYWEGLNK[13]-rotor). Rotor was modeled in the Xleap module in AMBER; RESP atomic charges for the peptides were derived using the RED server. To keep the ends capped and neutral, the N- and C-termini of MDM2 were capped with acetyl (ACE) and N-methyl (NME) moieties respectively, while the N- and C-termini of the peptide were capped with acetyl (ACE) and amidate ($NH_2$) respectively. Molecular dynamics simulations were performed with the SANDER module of the AMBER11 package employing the all-atom ff99SB force field. Each system was simulated for 100 ns at constant temperature (300 K) and pressure (1 atm), and structures were stored every 10 ps. Simulations were carried out for the complexes of MDM2 with the rotor analogs JP1-R and JP2-R. DSSP was used to calculate the secondary structures of the peptides. The simulation protocol was the same as reported earlier.

b) Replica Exchange Molecular Dynamics Simulations

We used Replica Exchange Molecular Dynamics (REMD) to investigate the stability of the helicity of the peptides. This REMD approach involves evolving a number of copies of the system in parallel at different temperatures and periodically exchanging the configurations between trajectories. This insures proper canonical sampling at all temperatures, with high-temperature simulations facilitating barrier crossings and low temperature simulations to explore local free energy minima. The systems were prepared and relaxed as described earlier. In each case, 24 replicas of the system were evolved in parallel for 20 ns at constant NVT, with temperatures evenly spaced between 300 and 400K in approximately 4-K intervals. After the first 100 ps, replica exchanges between each pair of nearest neighbor trajectories were attempted every 12 ps to equilibrate the system. The configurations were saved in 1-ps intervals over 20 ns of each simulation, providing an aggregate 480 ns of sampling for reach system with the exchange acceptance range of 36% to 45%.

Viscosity Experiment General Procedure

The rotors were dissolved in spectroscopy-grade DMSO to obtain a concentrated stock solution of 100 mM. The solution was vortexed to ensure complete dissolution.

For each rotor, 6 uL of the 100 mM stock was dissolved in 1200 uL of ethylene glycol in each 1.5 mL tube.

3 mL of glycerol was then heated in a boiling bath to reduce viscosity and improve pipetting.

In 5 separate tubes, add 200 uL of stained ethylene glycol to 800 uL of unstained ethylene glycol; 200 uL of stained ethylene glycol, 600 uL of unstained ethylene glycol to 200 uL glycerol; 200 uL of stained ethylene glycol, 400 uL of unstained ethylene glycol to 400 uL of glycerol; 200 uL of stained ethylene glycol, 200 uL of unstained ethylene glycol to 600 uL glycerol; and 200 uL of stained ethylene glycol to 800 uL glycerol. The fluids will then have a glycerol content of 0%, 20%, 40%, 60%, 80% respectively.

The five tubes were then placed on an inverting mixer and allowed to mix for at least 2 hours while the temperature equilibrate to room temperature.

Measurements were taken using 96-well Corning Flat-bottom Black plate and Tecan Infinite M-1000 Spectrophotometer.

Experiment with DNA/p53/Rotors. General Procedure.

For the first set with DNA only, 1×PBS buffer and p53 6× binding buffer were first added to the wells. Subsequently, rotor was added. Lastly, DNA was added. The combined solutions were mixed in each well and allowed to incubate in the dark at room temperature for, half an hour before data on fluorescence intensity was gathered.

For the second set with p53 only, 1×PBS buffer and p53 6× binding buffer were first added to the wells. Subsequently, rotor was added. Lastly, p53 was added. The combined solutions were mixed in each well and allowed to incubate in the dark at room temperature for half an hour before data on fluorescence intensity was gathered.

For the third set with DNA and p53, 1×PBS buffer and p53 6× binding buffer were first added to the wells. Subsequently, rotor was added and DNA was added. The combined solutions were mixed in each well and allowed to incubate in the dark at room temperature for half an hour before p53 was added. The combined solutions were then allowed to incubate in the dark at room temperature for another half an hour before data on fluorescence intensity was gathered.

6× binding buffer consists: 150 mM sodium phosphate buffer, 600 uM KCl, 24 mM DTT.

Measurements were taken using Greiner 384 black flat-clear-bottom for 18 uL mixtures, Corning 96 flat-black half-area for 80 uL and 100 uL mixtures, and Tecan Infinite M-1000 Spectrophotometer.

TABLE 1

Experimental data for Rotor/DNA/P53

| Compound | Acridine-based rotor | | | Thiazole-based rotor | | | Carbazole-based (2-arm) rotor | | Carbazole-based (3-arm) rotor | |
|---|---|---|---|---|---|---|---|---|---|---|
| Emission wavelength (nm) | 526 | | | 552 | | | 572 | | 582 | |
| Excitation wavelength (nm) | 480 | | | 510 | | | 458 | | 456 | |
| | 2X | 3.33X | 9.1X | 3.33X | 15X | 3.33X | 15X | 3.33X | | 15X |
| Final rotor concentration (uM) | 8 | 8 | 8 | 0.13 | 0.6 | 4 | 4 | — | | 1.5 |
| Final DNA concentration (uM) | 4 | 2.4 | 0.88 | 0.04 | 0.04 | 1.2 | 0.27 | — | | 0.1 |
| Final p53 Concentration (uM) - 4.16X of DNA | 16.64 | 9.98 | 3.66 | 0.17 | 0.17 | 4.99 | 1.12 | — | | 0.42 |
| Total volume (uL) | | 18 | | | 100 | | 18 | | 80 | |

TABLE 2

Experimental data for Rotor/DNA

| Compound | Acridine-based rotor | Thiazole-based rotor | Carbazole-based (2-arm) rotor | Carbazole-based (3-arm) rotor |
|---|---|---|---|---|
| Emission wavelength (nm) | 526 | 552 | 572 | 582 |
| Excitation wavelength (nm) | 480 | 510 | 458 | 456 |
| Final rotor concentration (uM) | 8 | Varies | Varies | Varies |
| Final DNA concentration (uM) | Varies | 0.04 | 4 | 0.1 |
| Total volume (uL) | 100 | 100 | 100 | 80 |

TABLE 3

Experimental data for Rotor viscosity test

| Compound | Acridine-based rotor | Thiazole-based rotor | Carbazole-based (2-arm) rotor | Carbazole-based (3-arm) rotor |
|---|---|---|---|---|
| Emission wavelength (nm) | 526 | 552 | 572 | 582 |
| Excitation wavelength (nm) | 480 | 510 | 458 | 510 (From Em spectra, should be 456 nm.) |
| Final rotor concentration (uM) | 10 | 100 | 100 | 100 |
| Total volume (uL) | 100 | 100 | 100 | 100 |

Modeling Results

TABLE 4

Helical propensity of JP1-R and JP2-R probes in their unbound conformations

| JP1-R | % Helicity | JP2-R | % Helicity |
|---|---|---|---|
| M | 0 | M | 0 |
| P | 5 | P | 1 |
| R | 26 | R | 20 |
| F | 44 | F | 45 |
| M | 51 | M | 52 |
| D | 54 | D | 59 |
| Y | 44 | Y | 49 |
| W | 49 | W | 50 |
| E | 42 | E | 44 |
| G | 43 | G | 35 |
| L | 34 | L | 22 |
| S | 12 | N | 5 |
| K | 0 | K | 0 |

TABLE 5

Components of binding free energy (in kcal/mol) of MDM2 with JP1-R and JP2-R peptides

| | MDM2-JP1-R | | MDM2 | | JP1-R | | Delta |
|---|---|---|---|---|---|---|---|
| ELE | −2910.6 | 65.2 | −2400.8 | 64.3 | −355.1 | 20.8 | −154.7 |
| VDW | −410.6 | 16.4 | −304.9 | 14.7 | −11.8 | 5.5 | −94.0 |
| GAS | −1015.6 | 69.3 | −761.5 | 66.9 | −4.0 | 23.4 | −250.2 |
| GBSOL | −1348.9 | 60.5 | −1249.2 | 60.4 | −279.7 | 20.1 | 180.1 |
| GBTOT | −2364.5 | 32.6 | −2010.7 | 29.1 | −283.7 | 12.0 | −70.1 |
| TSTOT | 1244.1 | 6.5 | 1056.6 | 3.8 | 228.3 | 5.2 | −40.8 |
| $\Delta G_{bind}$ | | | | | | | −29.3 |

| | -MDM2-JP2-R | | MDM2 | | JP2-R | | Delta |
|---|---|---|---|---|---|---|---|
| ELE | −2822.7 | 68.3 | −2383.4 | 59.7 | −288.0 | 30.0 | −151.3 |
| VDW | −409.4 | 17.3 | −304.9 | 14.9 | −14.9 | 6.6 | −89.6 |
| GAS | −933.8 | 72.9 | −742.8 | 64.3 | 51.2 | 33.1 | −242.2 |
| GBSOL | −1356.1 | 61.6 | −1265.3 | 53.0 | −266.9 | 29.6 | 176.2 |
| GBTOT | −2289.9 | 31.9 | −2008.2 | 29.1 | −215.7 | 12.0 | −66.0 |
| TSTOT | 1240.5 | 5.6 | 1058.3 | 5.1 | 225.8 | 6.2 | −43.5 |
| $\Delta G_{bind}$ | | | | | | | −22.5 |

TABLE 6

Residue wise energy contributions (in kcal/mol) of JP1-R peptides for their interactions with MDM2

| Residue | TVDW | TELE | TGAS | TGB | TGBSUR | TGBSOL | TGBTOT |
|---|---|---|---|---|---|---|---|
| M | −0.8 | −0.1 | −0.9 | 0.6 | −0.1 | 0.5 | −0.4 |
| P | −0.9 | 0.5 | −0.4 | 0.2 | −0.1 | 0.2 | −0.2 |
| R | −1.4 | 28.9 | 27.5 | −27.9 | −0.1 | −27.9 | −0.5 |
| F | −7.1 | −3.9 | −10.9 | 4.8 | −0.8 | 4.0 | −6.9 |
| M | −3.1 | −1.8 | −4.8 | 2.6 | −0.4 | 2.1 | −2.7 |
| D | −0.3 | −38.7 | −39.0 | 39.2 | 0.0 | 39.2 | 0.3 |
| Y | −4.0 | −1.9 | −5.9 | 3.7 | −0.4 | 3.3 | −2.6 |
| W | −6.9 | −4.3 | −11.2 | 5.9 | −0.7 | 5.2 | −6.0 |
| E | −0.6 | −45.4 | −46.0 | 46.4 | −0.1 | 46.4 | 0.4 |
| G | −0.4 | −1.1 | −1.5 | 1.6 | 0.0 | 1.6 | 0.1 |
| L | −4.6 | −3.8 | −8.3 | 4.1 | −0.5 | 3.6 | −4.7 |
| S | −3.0 | −1.6 | −4.6 | 3.8 | −0.3 | 3.5 | −1.0 |
| K | −2.6 | −1.0 | −3.6 | 1.4 | −0.2 | 1.2 | −2.4 |
| Rotor | −4.2 | −0.6 | −6.1 | 0.9 | −0.5 | 0.4 | −5.7 |

TABLE 7

Residue wise energy contributions (in kcal/mol) of JP2-R peptides for their interactions with MDM2

| Residue | TVDW | TELE | TGAS | TGB | TGBSUR | TGBSOL | TGBTOT |
|---|---|---|---|---|---|---|---|
| M | −0.7 | −0.3 | −1.0 | 0.9 | −0.1 | 0.8 | −0.2 |
| P | −0.6 | −0.1 | −0.8 | 0.6 | −0.1 | 0.5 | −0.3 |
| R | −1.2 | 27.5 | 26.3 | −26.9 | −0.1 | −27.0 | −0.7 |
| F | −6.8 | −3.7 | −10.4 | 4.8 | −0.8 | 4.0 | −6.4 |
| M | −2.9 | −1.6 | −4.5 | 2.4 | −0.4 | 2.0 | −2.5 |
| D | −0.2 | −37.1 | −37.3 | 37.5 | 0.0 | 37.5 | 0.2 |
| Y | −3.7 | −3.0 | −6.6 | 5.0 | −0.4 | 4.6 | −2.1 |
| W | −6.7 | −4.1 | −10.8 | 5.7 | −0.7 | 4.9 | −5.8 |
| E | −0.6 | −44.0 | −44.5 | 45.0 | 0.0 | 44.9 | 0.4 |
| G | −0.3 | −1.0 | −1.3 | 1.5 | 0.0 | 1.5 | 0.2 |
| L | −4.5 | −1.4 | −5.9 | 2.9 | −0.5 | 2.4 | −3.5 |
| N | −3.1 | −3.8 | −6.9 | 6.8 | −0.3 | 6.5 | −0.3 |
| K | −2.7 | −0.8 | −3.5 | 1.3 | −0.2 | 1.0 | −2.5 |
| Rotor | −2.9 | −0.7 | −4.8 | 1.4 | −0.5 | 1.8 | −3.0 |

TABLE 8

Figure 24:
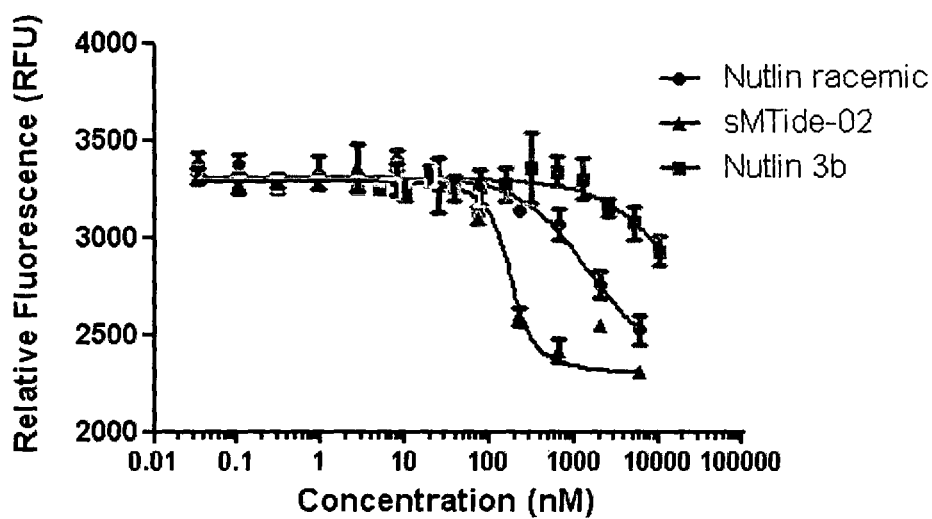
FIG. 24 shows that the JP1-R reporter is sensitive to several known inhibitors of p53-Mdm2 interaction. (A) Titration of known p53-Mdm2 inhibitors onto pre-bound Mdm2-JP1-R reactions (B) Calculated $K_d$s using JP1-R of compound inhibitors correlated well with previous reports of $K_d$.

Calculated $K_d$s using JP1-R of compound inhibitors correlated well with previous reports of $K_d$ (FIG. 24).

| Compound | Previous reported $K_d$ (nM) | Apparent $K_d$ using JP$_1$-R (nM) |
|---|---|---|
| Racemic Nutlin | 201.61 ± 60.85 (ITC) | 164.8 ± 29.43 |
| sMTide-02 | 34.35 ± 2.03 (FP) | 13.01 ± 4.29 |
| Nutlin-3b | N.A. | 2461 ± 687.3 |

TABLE 9

Amino acid sequence and dissociation constants of disclosed peptide variants

| Peptide ID | Aminoacid sequence | $K_d$[#] |
|---|---|---|
| JP1 | MPRFMDYWEGLSK | 18.83 ± 5.03 (SEQ ID NO: 1) |
| JP2 | MPRFMDYWEGLNK | 239.81 ± 53.79 (SEQ ID NO: 2) |

[#]Without lysine residue at C-terminus

Example 1a: Synthesis of Acridine-Based Fluorescent Molecular Rotor

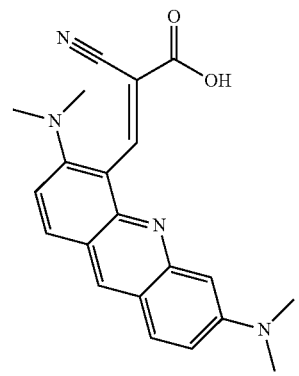

Acridine Orange Aldehyde (0.12 g, 0.42 mmol, 1 eq.) and cyanoacetic acid (0.053 g, 0.63 mmol, 1.5 eq.) was weighed into a 25 mL round-bottom flask flushed with argon. Triethylamine (0.29 mL, 2.09 mmol) was then added to the reaction mixture after solvating in anhydrous DMF. The reaction mixture was heated to 55° C. overnight, then evaporated to dryness and purified via column chromatography to yield orange solids (1.69 mg, 1%).

¹H NMR (CDCl₃, 400 MHz) δ 1.26 (s, 3H), 3.05 (s, 3H), 3.24 (s, 6H), 7.06 (dd, 1H, J=2.4, 9.3 Hz), 7.31 (s, 1H), 7.47 (s, 1H), 7.60 (d, 1H, J=9.0 Hz), 7.69 (d, 1H, J=9.4 Hz), 8.36 (s, 1H). ¹³C NMR (100 MHz, CDCl₃) δ 154.8, 154.6, 143.7, 142.8, 141.5, 130.4, 130.3, 117.8, 117.2, 115.2, 95.4, 93.8, 40.6, 30.4, 29.9.

Example 1b: Synthesis of Acridine Rotor-Biotin

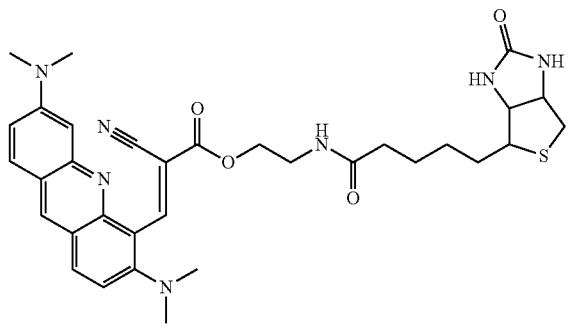 [SMILES: CN(C)c1ccc2cc3ccc(N(C)C)c(/C=C(\C#N)C(=O)OCCNC(=O)CCCCC4SCC5NC(=O)NC54)c3nc2c1]

Acridine Orange aldehyde (0.0190 g, 0.065 mmol, 1.0 eq.) and Biotin-CN (0.023 g, 0.065 mmol, 1.0 eq.) was weighed into a 25 mL round-bottom flask flushed with argon. Triethylamine (0.065 mL, 0.47 mmol, 7.0 eq.) was then added to the reaction mixture after solvating in anhydrous THF. The reaction mixture was then heated to 55° C. overnight, then evaporated to dryness and purified via column chromatography to yield pale orange solids.

¹H NMR (CDCl₃, 400 MHz) δ 0.87 (m, 1H), 1.24 (m, 3H), 1.54 (m, 2H), 2.70 (m, 2H), 2.91 (s, 6H), 2.98 (s, 6H), 3.02 (d, 2H, J=5.0 Hz), 3.23 (d, 3H, J=3.4 Hz), 3.29 (m, 1H), 4.26 (t, 1H, J=6.8 Hz), 6.77 (d, 1H, J=2.4 Hz), 7.01 (d, 1H, J=8.3 Hz), 7.18 (d, 1H, J=2.4 Hz), 7.34 (d, 1H, J=8.6 Hz), 7.49 (d, 1H, J=8.3 Hz), 8.06 (dd, 1H, J 9.5, 1.4 Hz), 8.26 (d, 1H, J=9.6 Hz). ¹³C NMR (100 MHz, CDCl₃) δ 171.8, 155.1, 152.3, 151.0, 139.4, 136.8, 134.5, 131.4, 130.8, 120.2, 117.5, 117.2, 115.4, 115.3, 114.9, 113.7, 101.9, 95.3, 77.4, 56.8, 46.0, 45.4, 40.6, 38.4, 36.7, 29.8, 27.9, 24.9, 20.4, 16.2. HRMS (TOF MS ES+): calcd for C₃₃H₃₉KN₇O₄S [M+K]⁺ 668.2421. found 668.9434.

Example 2: Synthesis of Thiazole-Based Fluorescent Molecular Rotor

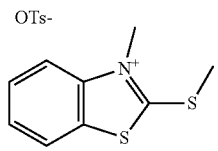

Preparation of 3-methyl-2-(methylthio) benzo[d]thiazol-3-ium 4-methylbenzenesulfonate 2-methylthiobenzothiazole (5.00 g, 27.62 mmol, 1 eq.) was weighed into a 25 mL round bottom flask under argon. Methyl p-toluenesulfonate (4.58 mL, 30.39 mmol, 1.1 eq.) was then added and the reaction mixture was allowed to stir at 130° C. for 1 hour. Acetone was then added after cooling to 70° C. until white precipitate appeared. The mixture was then refluxed for another 30 minutes before cooling to room temperature. Precipitate was collected by filtration and dried to yield pale yellow solids (10.02 g, 99%).

¹H NMR (CH₃OD, 400 MHz) δ 2.35 (s, 3H), 3.12 (s, 3H), 4.15 (s, 3H), 7.19 (d, 2H, J=4.0 Hz), 7.67 (d, 2H, J=8.0 Hz), 7.73 (t, 1H, j=8.0 Hz), 7.85 (t, 1H, J=8.0 Hz), 8.07 (d, 1H, J=8.0 Hz), 8.22 (d, 1H, J=8.0 Hz). ¹³C NMR (CH₃OD, 100 MHz) δ 183.3, 144.2, 143.7, 141.6, 130.8, 130.0, 129.8, 128.6, 127.0, 124.7, 116.5, 36.9, 21.3, 18.5.

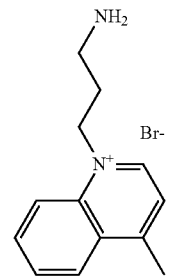

Preparation of 1-(3-aminopropyl)-4-methylquinolin-1-ium bromide 3-bromopropylamine hydrobromide (6.06 g, 27.68 mmol, 1.46 eq.) was weighed into an argon-flushed 25 mL round-bottom flask. Ethanol (5 mL) was then added to dissolve. Upon addition of Lepidine (2.5 mL, 18.91 mmol, 1 eq.), the reaction mixture was heated to 40° C. overnight. Pale pink precipitate (1.67 g, 32%) formed was filtered, washed and dried.

¹H NMR (D₂O, 400 MHz) δ2.55 (quin, 2H, J=8.0 Hz), 3.10 (s, 3H), 3.29 (t, 2H, J=8.0 Hz), 5.16 (t, 2H, J=8.0 Hz), 7.98 (d, 1H, J=4.0 Hz), 8.11 (t, 1H, J=4.0 Hz), 8.32 (t, 1H, J=8.0 Hz), 8.46 (d, 1H, J=8.0 Hz), 8.60 (d, 1H, J=8.0 Hz). ¹³C NMR (100 MHz, D₂O) δ 160.6, 147.3, 137.2, 135.6, 129.8, 127.3, 122.6, 118.2, 54.3, 36.5, 27.0 19.6.

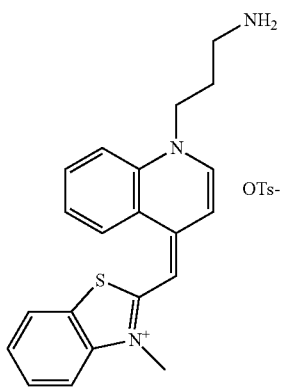 [SMILES: C[n+]1c(/C=C2/C=CN(CCCN)c3ccccc32)sc2ccccc21]

Preparation of Thiazole Orange Scaffold.

3-methyl-2-(methylthio)benzo[d]thiazol-3-ium 4-methylbenzenesulfonate (1.05 g, 2.86 mmol, 1 eq.) and 1-(3-aminopropyl)-4-methylquinolin-1-ium bromide (0.8 g, 2.86 mmol, 0.1 eq.) was weighed into 25 mL round-bottom flask under argon. 30 mL of ethanol was added to dissolve. Triethylamine (0.8 mL) was then added and the reaction was stirred at room temperature for 1 hour. Red precipitate (0.16 g, 11%) formed upon addition of ether was filtered, washed and dried.

¹H NMR (CH₃OD, 400 MHz) δ1.21 (t, 1H, J=8.0 Hz), 2.31 (td, 2H, J=Hz), 3.00 (s, 3H), 3.18 (m, 3H), 3.88 (s, 3H), 6.70 (t, 1H, J=8.0 Hz), 6.74 (s, 1H), 6.77 (d, 1H, J=8.0 Hz), 6.90 (td, 1H, J=4.0, 8.0 Hz), 7.14 (d, 1H, J=8.0 Hz), 7.23 (dd, 1H, J=4.0, 8.0 Hz), 7.32 (t, 1H, J=8.0 Hz), 7.50-7.71 (m, 4H), 7.88 (t, 1H, J=8.0 Hz), 8.08 (d, 1H, J=8.0 Hz), 8.29 (d, 1H, J=8.0 Hz), 8.54 (d, 1H, J=8.0 Hz). ¹³C NMR (100 MHz, CH₃OD) δ 162.1, 158.4, 150.8, 145.3, 142.2, 141.9, 139.1, 134.3, 129.4, 128.1, 127.5, 126.5, 123.7, 123.3, 122.1, 119.4, 113.6, 110.0, 109.5, 89.1, 55.2, 52.3, 34.0, 30.5, 30.2.

Example 3: Synthesis of Carbozole-Based (2-Arm) Fluorescent Molecular Rotor

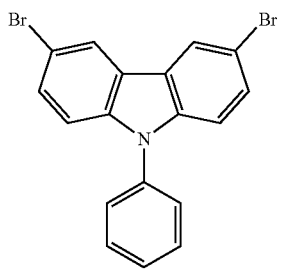 [SMILES: Brc1ccc2c(c1)c1cc(Br)ccc1n2-c1ccccc1]

Preparation of 3,6-dibromo-9-phenyl-9H-carbazole 9-phenyl-9H-carbazole (0.3 g, 1.23 mmol, 1 eq.) was dissolved in DMF. N-Bromosuccinimide (0.44 g, 2.47 mmol, 2 eq.) was then added slowly and the resultant mixture was allowed to stir at room temperature overnight. The reaction mixture was then poured into brine and extracted with DCM. The organic extracts were then dried with Na₂SO₄ and concentrated. Crude product was then re-precipitated with methanol and THF gave white solids as 3,6-dibromo-9-phenyl-9H-carbazole (0.32 g, 64%).

¹H NMR (CDCl₃, 400 MHz) δ 7.24 (s, 1H), 7.48-7.52 (m, 5H), 7.59-7.64 (m, 2H), 8.20 (d, 2H, J=2.0 Hz). ¹³C NMR (100 MHz, CDCl₃) δ 140.1, 137.0, 130.3, 129.5, 128.3, 127.2, 124.1, 123.4, 113.2, 111.7.

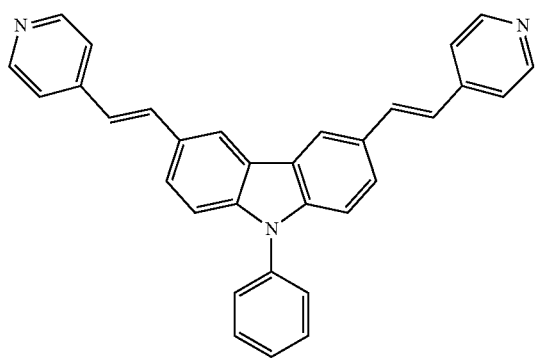 [SMILES: C(=C\c1ccc2c(c1)c1cc(/C=C/c3ccncc3)ccc1n2-c1ccccc1)/c1ccncc1]

Preparation of 9-phenyl-3,6-bis((E)-2-(pyridin-4-yl)vinyl)-9H-carbazole 3,6-dibromo-9-phenyl-9H-carbazole (96.4 mg, 0.24 mmol, 1 eq.), palladium diacetate (5 mg, 22.5 µmol, 0.09 eq.), tris-o-tolylphosphine (12.2 mg, 0.04 mmol, 0.16 eq.) and 4-vinylpyridine (0.17 mL, 1.55 mmol, 6.2 eq.) were added to triethylamine dissolved in degassed THF. The reaction mixture was then heated for 4 days at 110° C. in a sealed tube, and subsequently, diluted in DCM and filtered over celite after cooling to room temperature. The filtrate was washed with brine, dried over Na₂SO₄ and evaporated to dryness to afford a brown paste that was purified by column chromatography to yield yellow solids (80.8 mg, 72%).

¹H NMR (CDCl₃, 400 MHz) δ 7.10 (d, 2H, J=16.0 Hz), 7.39 (s, 1H), 7.42 (d, 5H, J=4.0 Hz), 7.51-7.59 (m, 6H), 7.63-7.67 (m, 4H), 8.34 (s, 2H), 8.59 (d, 4H, J=4.0 Hz). ¹³C NMR (100 MHz, CDCl₃) δ 150.3, 145.3, 141.9, 134.7, 134.0, 130.3, 129.1, 127.2, 125.7, 124.1, 123.9, 123.7, 120.8, 119.5, 110.7. HRMS (TOF MS ES+): calcd for C₃₂H₂₃N₃Na [M+Na]⁺472.1784. found 472.1779.

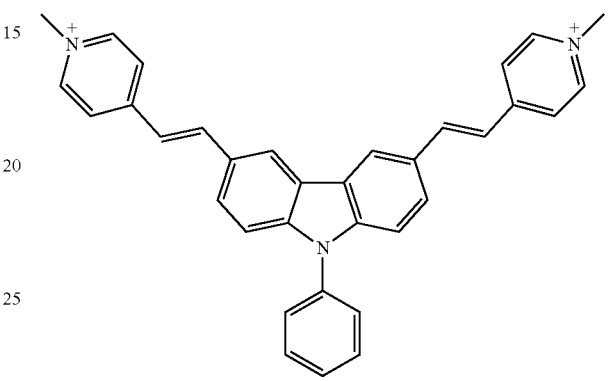

Preparation of 4,4'-((1E,1'E)-(9-phenyl-9H-carbazole-3,6-diyl)bis(ethene-2,1-diyl))bis(1-methylpyridin-1-ium)

9-phenyl-3,6-bis((E)-2-(pyridin-4-yl)vinyl)-9H-carbazole (80.8 mg, 0.18 mmol) was weighed into round bottom flask and dissolved in a DCM/MeOH (1:1 v:v) mixture. Methyl iodide (2 mL, 32.13 mmol) was then added. The solution was heated at reflux for 3 days and cooled to room temperature. The red precipitate (111.3 mg, 84%) was filtered and dried.

¹H NMR (DMSO, 400 MHz) δ 4.27 (s, 6H), 7.50 (d, 2H, J=8.0 Hz), 7.57-7.64 (m, 3H), 7.65-7.78 (m, 4H), 7.93 (d, 2H, J=8.0 Hz), 8.23 (d, 5H, J=8.0 Hz), 8.27 (s, 1H), 8.72 (s, 2H), 8.84 (D, 4H, J=4.0 Hz). ¹³C NMR (100 MHz, DMSO) δ 152.8, 144.9, 142.0, 141.5, 135.8, 130.4, 128.5, 128.2, 127.2, 126.8, 123.2, 123.1, 121.2, 110.9, 46.8.

Example 4: Synthesis of Carbozole-Based (3-Arm) Fluorescent Molecular Rotor

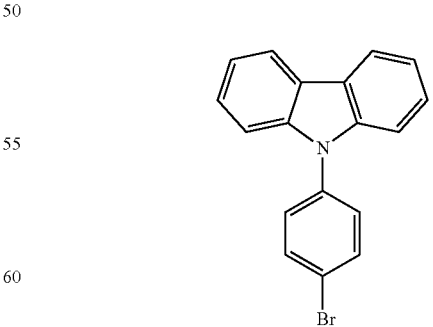

Preparation of 9-(4-bromophenyl)-9H-carbazole

Copper (II) sulphate (1.35 g, 8.48 mmol, 0.8 eq.), potassium carbonate (2.93 g, 21.20 mmol, 2 eq.), dibromobenzene (5.00 g, 21.20 mmol, 2 eq.) and carbazole (1.77 g, 10.60 mmol, 1 eq.) were heated in a round-bottom flask at 210° C. overnight under argon. After cooling to room temperature, water was added to stop the reaction and the mixture was extracted with DCM. The organic layer was dried with $Na_2SO_4$, concentrated in vacuo and purified via column chromatography to yield white crystals (1.05 g, 31%).

$^1$H NMR ($CDCl_3$, 400 MHz) δ 7.28-7.59 (m, 9H), 7.74 (d, 1H, J=8.6 Hz), 8.14 (d, 1H, J=7.8 Hz), 8.19 (d, 1H, J=7.8 Hz). $^{13}$C NMR (100 MHz, $CDCl_3$) δ 140.8, 137.0, 133.3, 128.9, 126.2, 123.7, 121.1, 120.5, 120.4, 109.7. HRMS (TOF MS ES+): calcd for $C_{18}H_{12}$ BrNK $[M+K]^+$ 359.9790. found 359.2444.

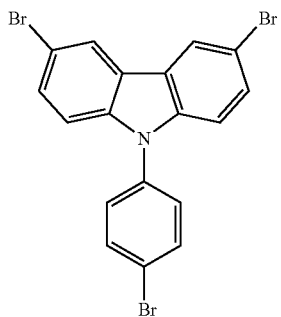 [SMILES: Brc1ccc(-n2c3ccc(Br)cc3c3cc(Br)ccc32)cc1]

Preparation of 3,6-dibromo-9-(4-bromophenyl)-9H-carbazole

To a solution of 9-(4-bromophenyl)-9H-carbazole (0.1 g, 0.31 mmol, 1 eq.) in DMF (3.5 mL), N-Bromosuccinimide (0.12 g, 0.69 mmol, 2.2 eq.) in DMF (3.5 mL) was added dropwise and the mixture was allowed to stir at room temperature for 3 hours. Water was then added to give white precipitate which was recrystallized with hexane to yield white solids (0.082 g, 55%).

$^1$H NMR ($CDCl_3$, 400 MHz) δ 7.20 (d, 2H, J=8.5 Hz), 7.37 (d, 2H, J=8.6 Hz), 7.50 (dd, 2H, J=1.9, 8.7 Hz), 7.73 (d, 2H, J=8.5 Hz). $^{13}$C NMR (100 MHz, $CDCl_3$) δ 139.8, 136.0, 133.5, 129.7, 128.7, 124.2, 123.5, 121.9, 113.5, 111.4. HRMS (TOF MS ES+): calcd for $C_{18}H_{10}$ $Br_3N$ $[M]^+$ 478.8338. found 478.8349.

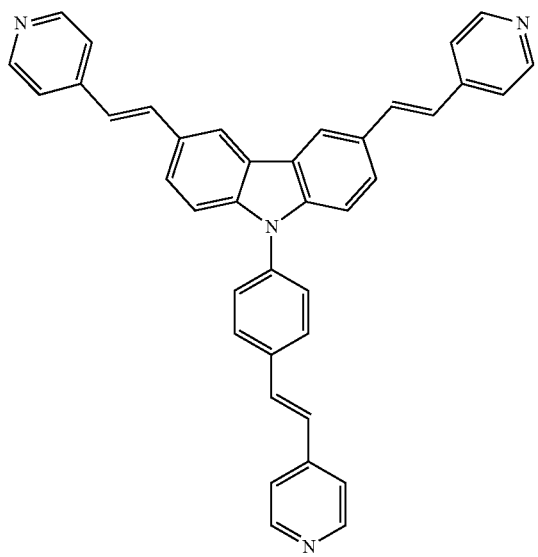 [SMILES: C(=C\c1ccc(-n2c3ccc(/C=C/c4ccncc4)cc3c3cc(/C=C/c4ccncc4)ccc32)cc1)/c1ccncc1]

Preparation of 3,6-bis((E)-2-(pyridin-4-yl)vinyl)-9-(4-((E)-2-(pyridin-4-yl)vinyl)phenyl)-9H-carbazole 3,6-dibromo-9-(4-bromophenyl)-9H-carbazole (0.082 g, 0.17 mmol, 1 eq.), palladium diacetate (4.8 mg, 21.4 μmol, 0.13 eq.), tris-o-tolylphosphine (14.2 mg, 21.4 μmol, 0.27 eq.) and 4-vinylpyridine (0.17 mL, 1.59 mmol, 9.3 eq.) were added to triethylamine dissolved in degassed THF. The reaction mixture was then heated for 4 days at 110° C. in a sealed tube, and subsequently, diluted in DCM and filtered over celite after cooling to room temperature. The filtrate was washed with brine, dried over $Na_2SO_4$ and evaporated to dryness to afford a brown paste that was purified by column chromatography to yield orange solids.

$^1$H NMR ($CDCl_3$, 400 MHz) δ 7.08 (t, 5H, J=16.1 Hz), 7.36-7.41 (m, 15H), 7.77 (d, 2H, J=8.4 Hz), 8.31 (s, 2H), 8.54 (d, 6H, J=6.1 Hz).

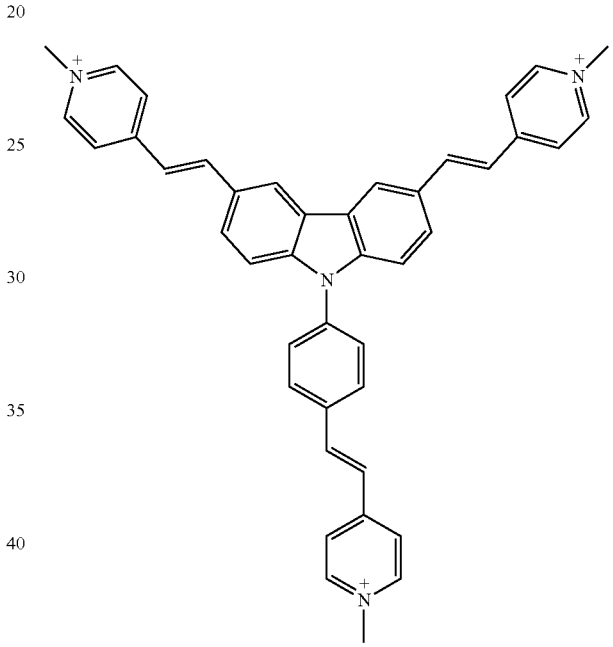

Preparation of 4,4'-((1E,1'E)-(9-(4-((E)-2-(1-methyl-pyridin-1-ium-4-yl)vinyl)phenyl)-9H-carbazole-3,6-diyl)bis(ethene-2,1-diyl))bis(1-methylpyridin-1-ium)

3,6-bis((E)-2-(pyridin-4-yl)vinyl)-9-(4-((E)-2-(pyridin-4-yl)vinyl)phenyl)-9H-carbazole (176.5 mg, 0.32 mmol) was weighed into round bottom flask and dissolved in a DCM/MeOH (1:1 v:v) mixture. Methyl iodide (6 mL, 96.39 mmol) was then added. The solution was heated at reflux for 3 days and cooled to room temperature. The red precipitate (108.3 mg, 35%) was filtered and dried.

$^1$H NMR (DMSO, 400 MHz) δ4.28 (s, 6H), 4.31 (s, 3H), 7.59-7.71 (m, 5H), 7.87 (d, 2H, J=8.0 Hz), 7.96 (d, 2H, J=2, 9.2 Hz), 8.11 (d, 1H, J=8.0 Hz), 8.17-8.21 (m, 2H), 8.25 (d, 4H, J=8.0 Hz), 8.28 (s, 1H), 8.30 (d, 2H, J=4.0 Hz), 8.69 (s, 1H), 8.76 (s; 1H), 8.86 (d, 5H, J=8.0 Hz), 8.93 (d, 2H, J=8.0 Hz). $^{13}$C NMR (100 MHz, DMSO) δ 152.7, 145.3, 145.0, 141.7, 139.3, 135.0, 130.0, 128.6, 127.2, 124.4, 123.7, 123.5, 123.1, 121.4, 111.1, 47.0, 46.8.

Example 5a: Synthesis of Pyrene-Based Fluorescent Molecular Rotor

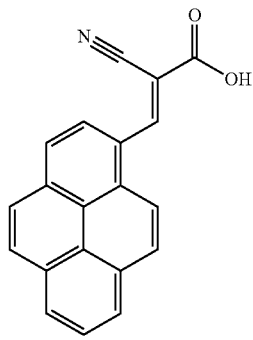 [SMILES: N#C/C(=C\c1ccc2ccc3cccc4ccc1c2c34)C(=O)O]

Pyrenecarboxaldehyde (0.5 g, 2.17 mmol, 1.0 eq.) and cyanoacetic acid (0.277 g, 3.26 mmol, 1.5 eq.) was weighed into a 25 mL round-bottom flask flushed with argon. Triethylamine (0.60 mL, 4.34 mmol, 2.0 eq.) was then added to the reaction mixture after solvating in anhydrous THF. The reaction mixture was then heated to 55° C. overnight, then evaporated to dryness and purified via column chromatography to yield pale orange solids (0.2 g, 31%).

$^1$H NMR (DMSO, 400 MHz) δ8.14 (t, J=7.6 Hz, 1H), 8.23 (d, 1H, J=8.9 Hz), 8.30 (d, 1H, J=8.7 Hz), 8.34 (d, 1H, J 7.5 Hz), 8.39 (m, 3H), 8.57 (d, 1H, J=8.1 Hz), 9.00 (s, 1H). $^{13}$C NMR (100 MHz, DMSO) δ 162.8, 145.8, 132.2, 130.7, 130.1, 129.1, 128.8, 127.9, 127.1, 126.7, 126.3, 126.1, 125.8, 124.9, 123.8, 123.6, 122.6, 120.4, 118.9.

Example 5b: Synthesis of Pyrene Rotor-Biotin

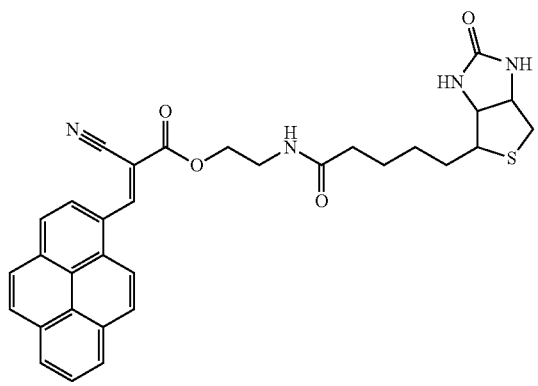 [SMILES: N#C/C(=C\c1ccc2ccc3cccc4ccc1c2c34)C(=O)OCCNC(=O)CCCCC1SCC2NC(=O)NC21]

Preparation of Pyrene Biotin.

Pyrenecarboxaldehyde (21.7 mg, 0.094 mmol, 1.0 eq.) and Biotin-CN (0.05 g, 0.141 mmol, 1.5 eq.) was weighed into a 25 mL round-bottom flask flushed with argon. Triethylamine (0.065 mL, 0.47 mmol, 5 eq.) was then added to the reaction mixture after solvating in anhydrous THF. The reaction mixture was then heated to 55° C. overnight, then evaporated to dryness and purified via column chromatography to yield pale orange solids (29.2 mg, 55%).

$^1$H NMR (MeOD, 400 MHz) δ 0.85 (m, 2H), 1.24 (s, 4H), 2.00 (m, 4H), 2.55 (m, 2H), 3.05 (m, 2H), 5.33 (t, 1H, J=4.8 Hz), 8.14 (t, J=7.6 Hz, 1H), 8.23 (d, 1H, J=8.9 Hz), 8.30 (d, 1H, J=8.7 Hz), 8.34 (d, 1H, J=7.5 Hz), 8.39 (m, 3H), 8.56 (d, 1H, J=8.3 Hz), 8.95 (s, 1H). HRMS (TOF MS ES+): calcd for $C_{32}H_{30}KN_4O_4S$ [M+K]$^+$ 605.1988. found 604.9648.

Example 6a: Synthesis of Julodine-Based Fluorescent Molecular Rotor (CCVJ)

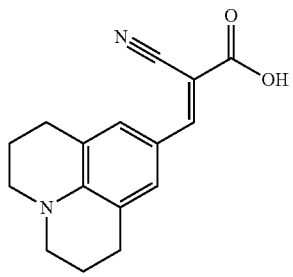 [SMILES: N#C/C(=C\c1cc2c3c(c1)CCCN3CCC2)C(=O)O]

Julolidine-carboxaldehyde (0.5 g, 2.48 mmol, 1.0 eq.) and cyanoacetic acid (0.3170 g, 3.73 mmol, 1.5 eq.) was weighed into a 25 mL round-bottom flask flushed with argon. Triethylamine (0.69 mL, 4.97 mmol, 2.0 eq.) was then added to the reaction mixture after solvating in anhydrous THF. The reaction mixture was then heated to 55° C. overnight, then evaporated to dryness and purified via column chromatography to reddish-brown solids (0.18 g, 27%).

$^1$H NMR (DMSO, 400 MHz) δ1.87 (m, 3H), 2.67 (t, J=6.3 Hz, 1H), 3.31 (t, J=5.9 Hz, 1H), 7.48 (s, 2H), 7.84 (s, 2H). $^{13}$C NMR (100 MHz, DMSO) δ 165.1, 152.8, 147.1, 130.7, 120.4, 119.5, 118.5, 117.5, 104.5, 49.4, 27.0, 20.6.

Example 6b: Synthesis of Julodine Rotor-Biotin

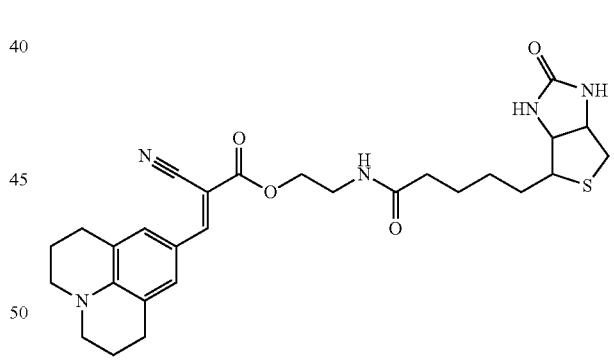

Julolidine-carboxaldehyde (0.05 g, 0.25 mmol, 1.0 eq.) and Biotin-CN (0.1 g, 0.28 mmol, 1.13 eq.) was weighed into a 25 mL round-bottom flask flushed with argon. Triethylamine (0.07 mL, 0.5 mmol, 2.0 eq.) was then added to the reaction mixture after solvating in anhydrous THF. The reaction mixture was then heated to 50° C. overnight, then evaporated to dryness and purified via column chromatography to yield yellowish orange solids (27.8 mg, 18%).

$^1$H NMR (CDCl$_3$, 400 MHz) δ 1.42 (m, 2H), 1.59 (m, 4H), 1.98 (m, 2H), 2.25 (m, 1H), 2.31 (m, 1H), 2.75 (t, 2H, J=6.3 Hz), 2.97 (dd, 1H, J=13.8, 5.4 Hz), 3.19 (m, 1H), 3.36 (m, 4H), 3.56 (m, 1H), 3.68 (m, 1H), 4.13 (d, 1H, J=8.0 Hz), 4.22 (t, 1H, J=5.9 Hz), 4.27 (m, 1H), 4.35 (dd, 2H, J=5.7, 4.3

Hz), 5.98 (s, 1H), 6.78 (s, 1H), 7.52 (m, 2H), 7.70 (dd, 1H, J=5.7, 3.3 Hz), 7.94 (s, 1H). $^{13}$C NMR (100 MHz, CDCl$_3$) δ 173.6, 165.1, 162.1, 155.0, 148.4, 132.0, 121.1, 118.3, 114.0, 90.0, 64.4, 62.2, 57.5, 54.9, 50.4, 39.1, 37.9, 36.6, 34.0, 27.7, 27.2, 25.4, 25.1, 21.1. HRMS (TOF MS ES+): calcd for $C_{28}H_{35}N_5NaO_4S$ [M+Na]$^+$ 560.2302. found 560.2321.

Example 7: Fluorescent Molecular Rotors Bound to Ligands

Molecular rotors can be modified to incorporate a targeting molecule or short targeting peptides. For example, biotin was attached to the molecular rotors and an increase in fluorescence was observed upon binding to the streptavidin protein.

Molecular rotors may be conjugated to targeting peptides via a 3-carbon linker. Amide linkage may be used to conjugate the rotors via a lysine residue at the carboxy-terminus of targeting peptides.

Example 8: Viscosity Experiments with Fluorescent Molecular Rotors

FIGS. 3a to 10 illustrate the emission spectras of fluorescent molecular rotors. It is shown that these fluorescent molecular rotors display an increase in fluorescence upon increase in viscosity. For all the rotors synthesized (julodine-based, aciridine-based, pyrene-based, thiazole-based and carbozole-based (2-arm and 3-arm)), the viscosity tests showed good sensitivity and trend.

Example 9: Binding of Rotor-Small Molecule with Protein

Figure 4A:
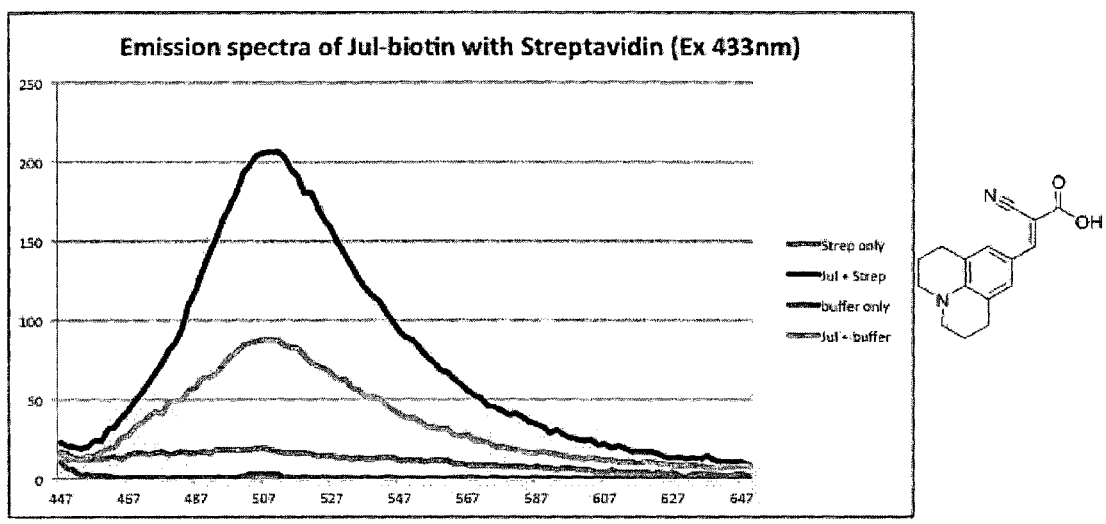
FIGS. 4a and 4b show that fluorescent molecular rotors of the present invention display an increase in fluorescence upon binding to Streptavidin protein.

A fluorescent julodine-based molecular rotor, 9-(2-carboxy-2-cyanovinyl) julolidine (CCVJ) was conjugated to biotin and changes in fluorescence was measured upon binding to streptavidin. A 2-fold fluorescence increase was measured upon the addition of streptavidin, demonstrating the utility of the biotin-rotor probe (FIG. 4a).

Figure 4B:
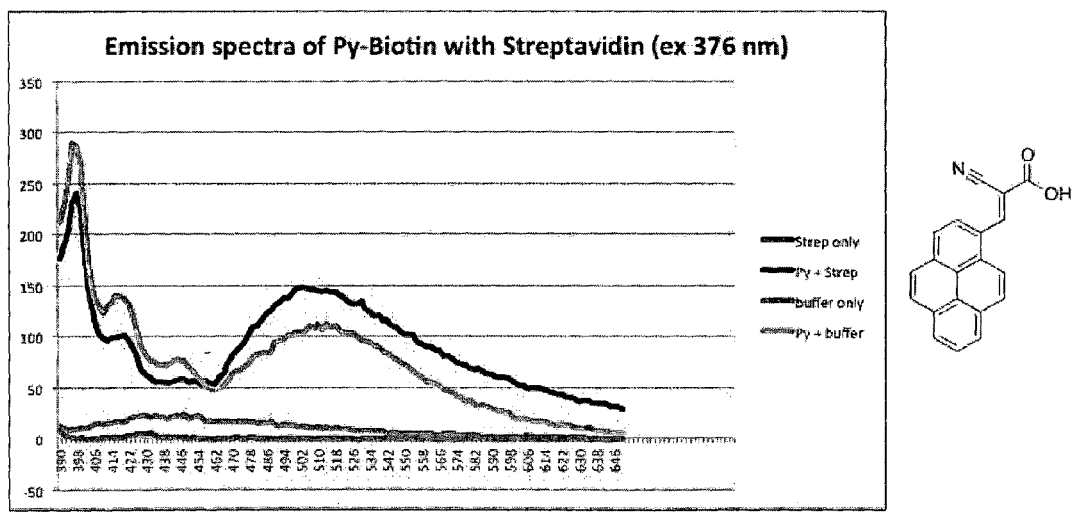

A pyrene-based molecular rotor was also tested and displayed fluorescence increase upon binding to streptavidin (FIG. 4b).

Example 10: Binding of Rotor-DNA with Protein

DNA Intercalation of Molecular Rotors

Figure 6:
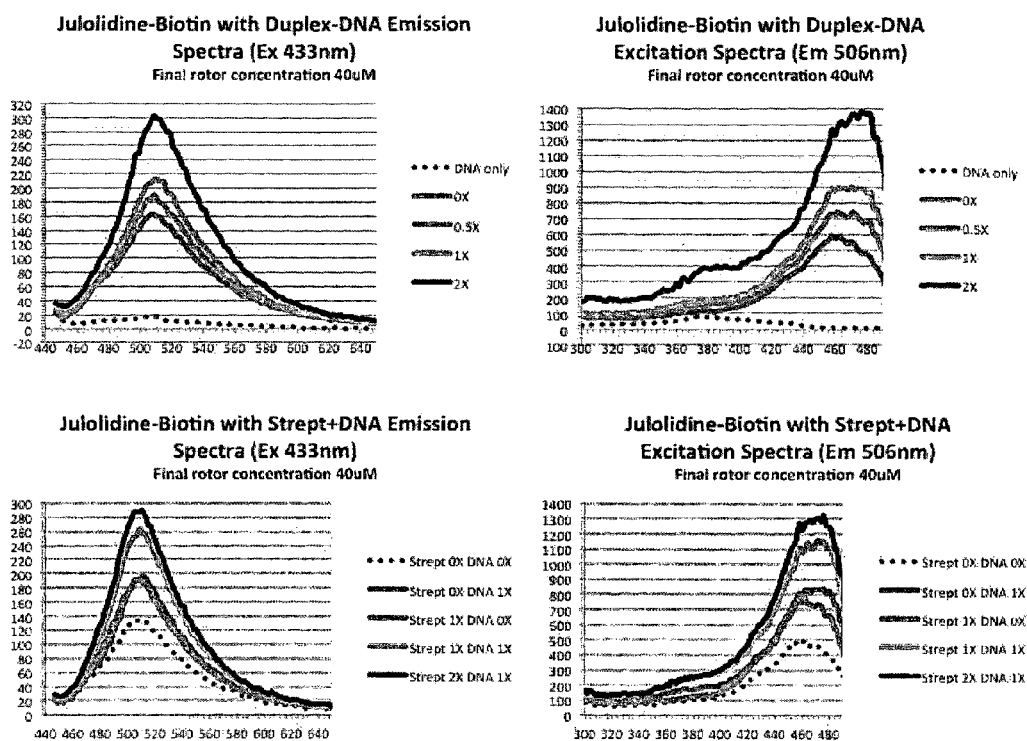
FIG. 6 shows the emission and excitation spectrums of CCVJ-Biotin with Streptavidin, DNA and both Streptavidin and DNA.
Figure 7:
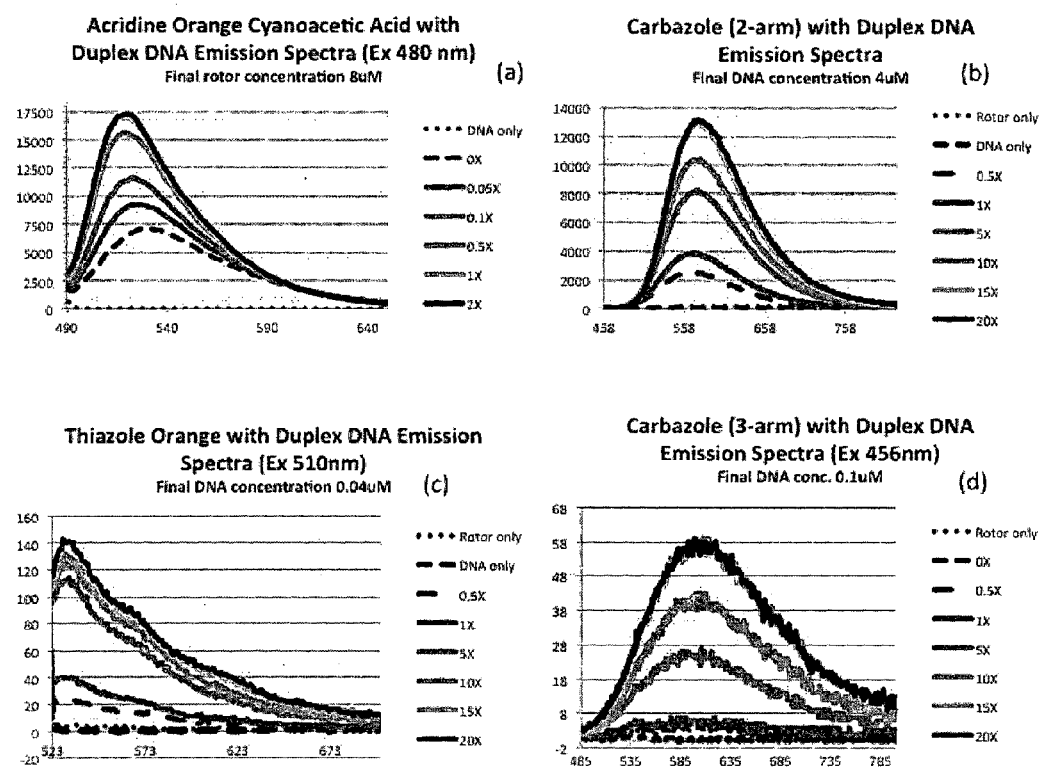
FIG. 7 shows the emission spectras of selected rotors with p53 binding sequence duplex DNA (a) rotor concentration constant at 8 uM with varying DNA ratios, b-d) DNA constant at 4 uM, 0.04 uM, 0.1 uM for b, c and d respectively with varying rotor concentration.)
Figure 16:
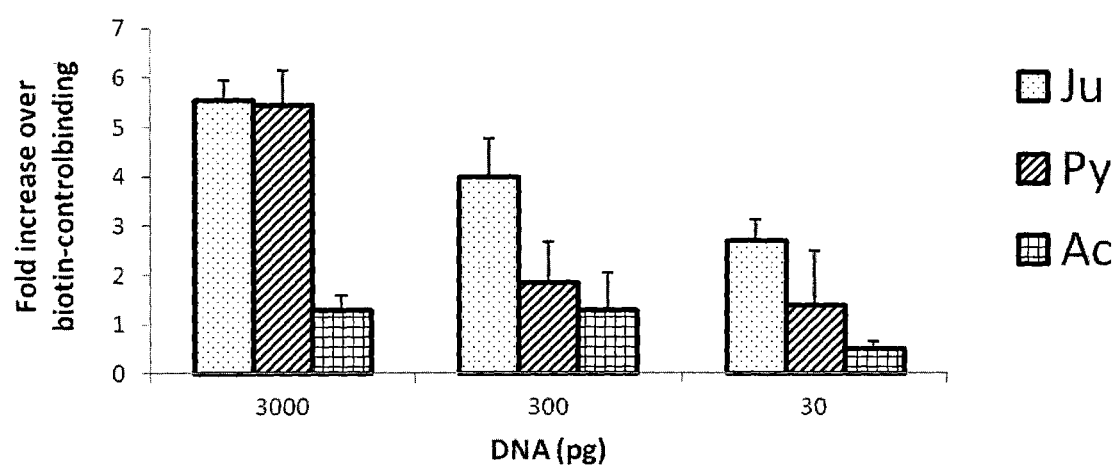
FIG. 16 shows a biotinylated-rotor DNA pulldown. Commercial streptavidin coated plates were incubated with 50 ul of each biotinylated rotor, or free-biotin (20 uM in PBS) for 20 mins at r.t., washed (2xPBST, 2xPBS) and blocked with 3% BSA/PBS for 30 mins before adding DNA (450 bp PCR fragment in PBS) across a concentration range (30, 300, or 3000 pg) for a further 20 mins at r.t. Wells are then washed again (3xPBST, 3xPBS) before DNA was eluted with 150 mM NaOH. Eluate was then neutralized (with 150 mM HCl and 50 mM Tris-Cl, pH 7.4) and used for real-time PCR quantification of template DNA. Data shows fold-increase of rotor captured DNA over background binding in free-biotin control wells. Error depicts S.D. of 2 separate binding reactions.
Figure 17:
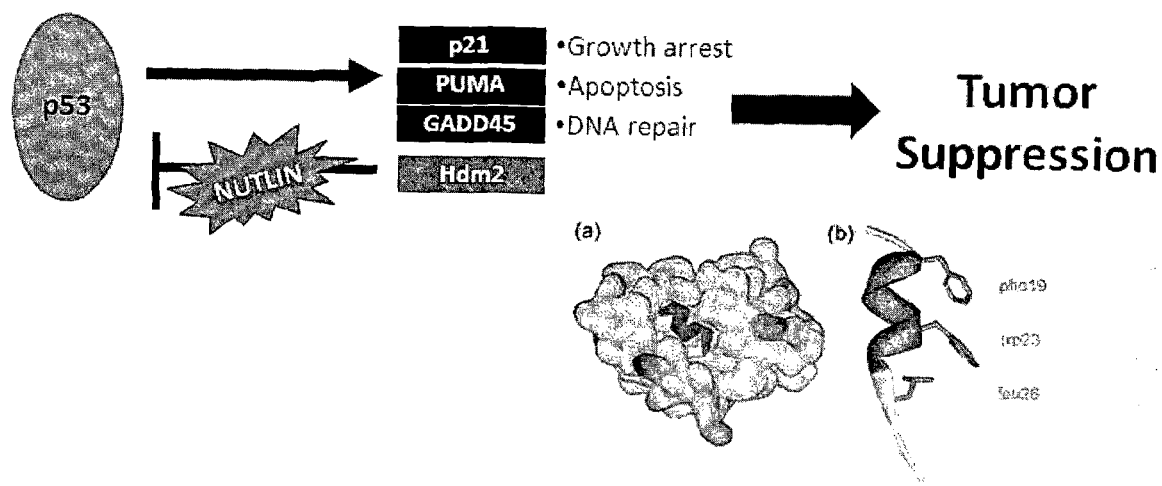
FIG. 17 schematically depicts p53 function in cells. p53 transcribes target proteins to suppress cancer/cellular transformation. (a) Diagram showing p53 peptide (shaded ribbon) binding to MDM3 N-terminal hydrophobic pocket. (b) Ribbon diagram showing amino acid side-chain projections important for critical contacts in MDM2 binding pocket.
Figure 18:
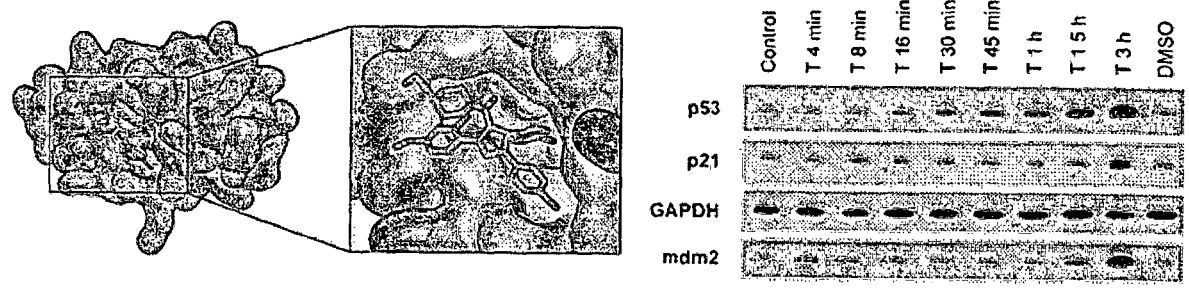
FIG. 18 depicts (top left) Nutlin binding to MDM2 pocket. (top right) Western blot showing cellular levels of p53 target proteins (p21, MDM2) in response to Nutlin treatment.
Figure 19:
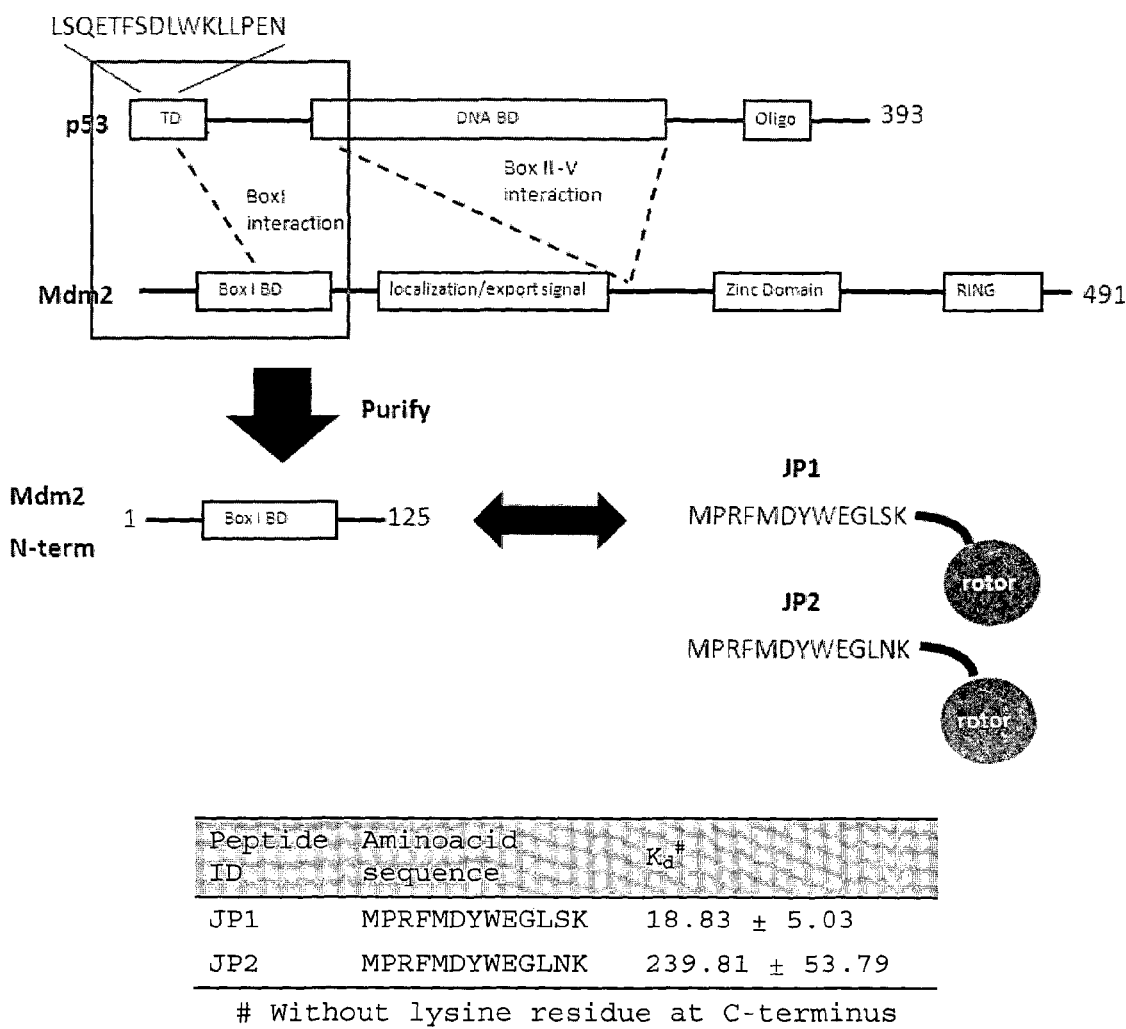
FIG. 19 schematically shows the design rationale of model system. The box I interaction domain between MDM2 and p53 is used and involves the N-terminal domains of both proteins. MDM2 N-term (18-125) is purified and used for binding with rotor conjugated to either JP1 (SEQ ID NO:1) or JP2 (SEQ ID NO:2) peptide sequences.

Intercalation of DNA with fluorescent molecular rotors displayed a strong increase in fluorescence signal. The intercalating interaction with DNA was further exemplified through a pull-down assay with biotin-conjugated rotors and streptavidin beads (FIGS. 6, 7 and 16).

FIGS. 4a and 4b illustrate that julodine-based and pyrene-based molecular rotors display an increase in fluorescence upon binding to Streptavidin protein demonstrating the usefulness of fluorescent molecular rotors as a probe for streptavidin protein.

Molecular Rotors in Detection of p53-DNA Binding

Figure 5:
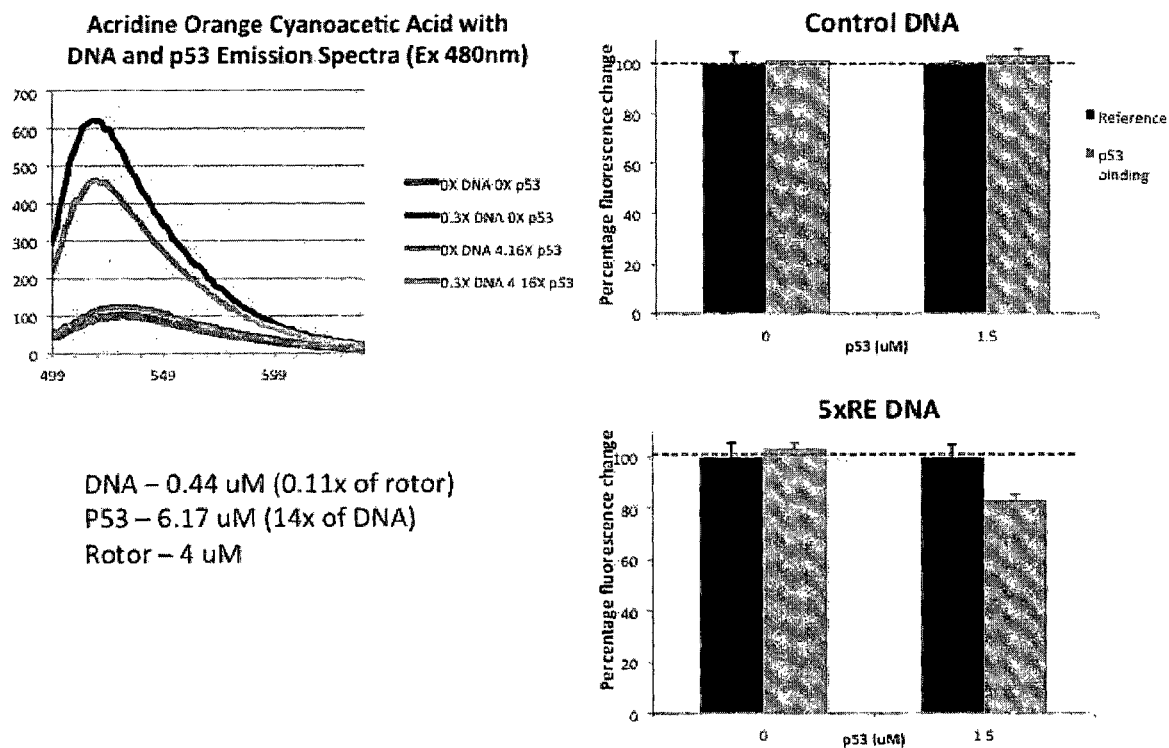
FIG. 5 shows a fluorescence displacement assay using a fluorescent molecular rotor of formula (ii) upon binding of p53 protein to DNA. A decrease in fluorescence signal can be observed upon protein binding. DNA—0.44 μM (0.11× of rotor); p53—6.17 μM (14× of DNA); Fluorescent molecular rotor—4 μM.

An acridine-based rotor was used in a fluorescence displacement assay to report on the binding of p53 protein to DNA. A decreased fluorescence signal was observed upon protein binding (FIG. 5).

Protein-DNA Interactions

The intercalating activity of fluorescent molecular rotors was tested on the binding sequence of p53 protein. It was shown that the fluorescence intensity of the rotors increase steadily until they reached saturation at 0.5× rotor for acridine-based rotor, and 15× rotor for thiazole-based and carbazole-based (2-arm and 3-arm) rotors (FIG. 7).

From the trend given by the emission spectras of rotor with DNA, it can be concluded that the rotors do intercalate or bind to the DNA shown by the increase in fluorescence intensity due to the restriction of rotor motion upon intercalating or binding.

The use of rotors in protein-DNA interactions was then tested.

Figure 8:
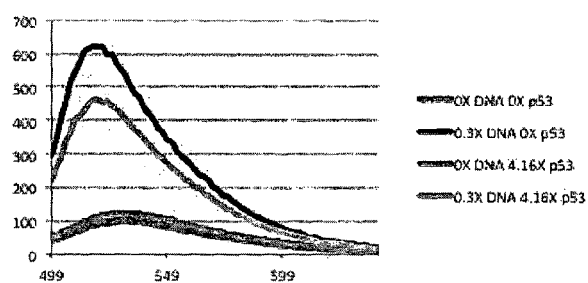
FIG. 8 shows the emission spectras of acridine-based rotor with p53 and its binding sequence duplex DNA.
Figure 8:
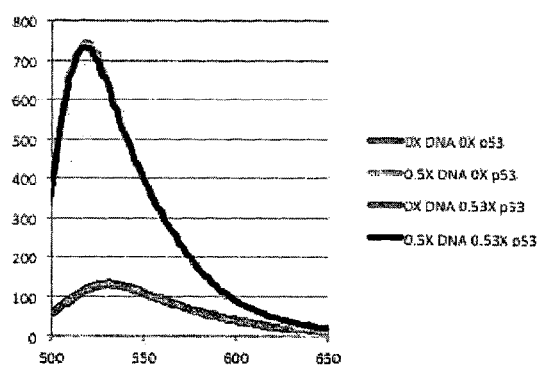
Figure 8:
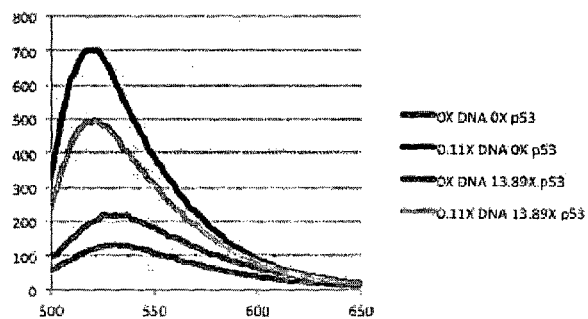
Figure 9:
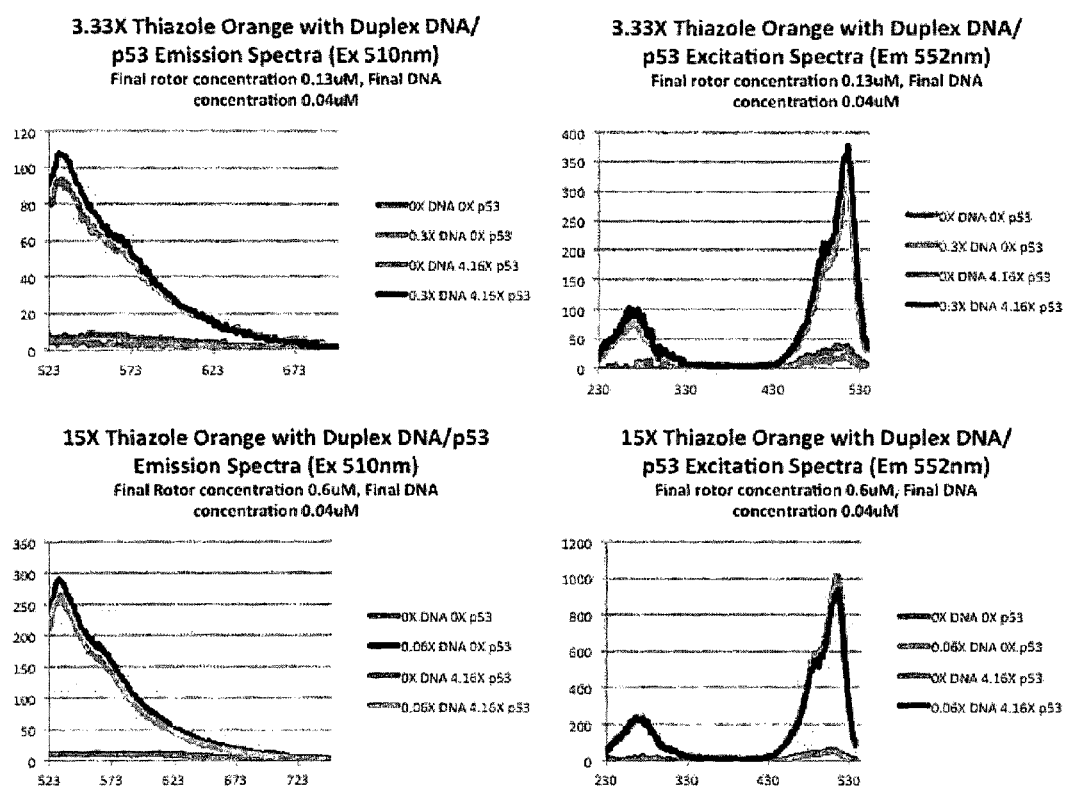
FIG. 9 shows the emission and excitation spectras of thiazole-based rotor with p53 and its binding sequence duplex DNA.
Figure 10:
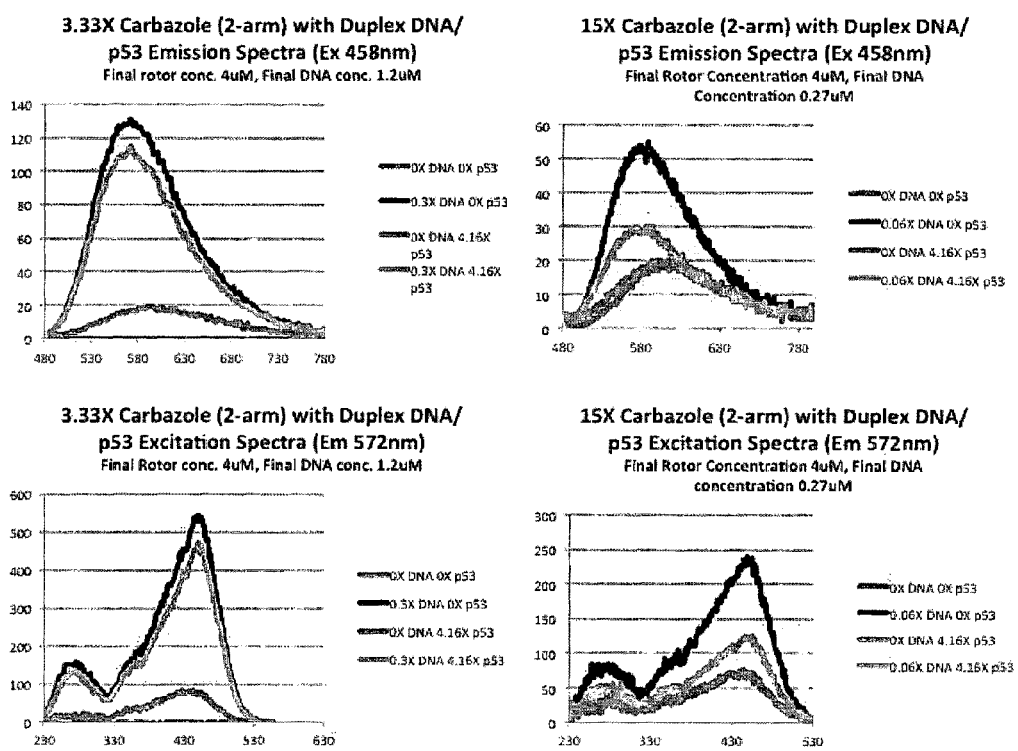
FIG. 10 shows the emission and excitation spectras of Carbazole-based (2-arm) rotor with p53 and its binding sequence duplex DNA.

When a significant portion of p53 protein was added to acridine-based rotor bound to DNA, the fluorescence intensity dropped. It is hypothesized that upon interaction and binding of p53 with the DNA, the bulky acridine-based rotor intercalator was freed from the intercalating site, resulting in the reduction of fluorescence intensity (FIG. 8).

p53 protein was added to carbazole-based (2-arm) rotor bound to DNA. A turn-off effect was observed when p53 was added, with effect most significant when the DNA was saturated with the 15× compound (FIG. 10).

Figure 12:
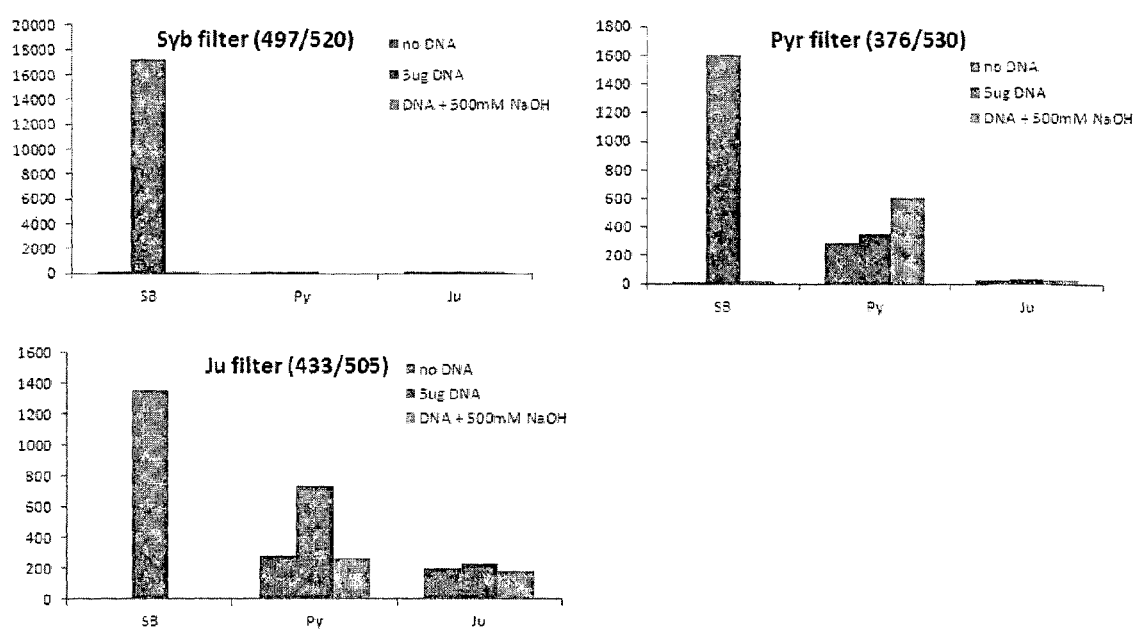
FIG. 12 shows the fluorescence of Sybr green rotor, CCVJ rotor and pyrene-based rotor. 100 uM of Sybr green, Pyrene or CCVJ rotors were each added to either 5 ug plasmid DNA, 5 ug DNA with 500 mM NaOH, or PBS buffer only. Resulting fluorescence for each reaction mixture were then compared across the respective filters (Sybr 497/520, Pyrene 376/530, Julolidine 433/505). A weak signal was observed for julolidine and was dropped for further experiments.
Figure 13:
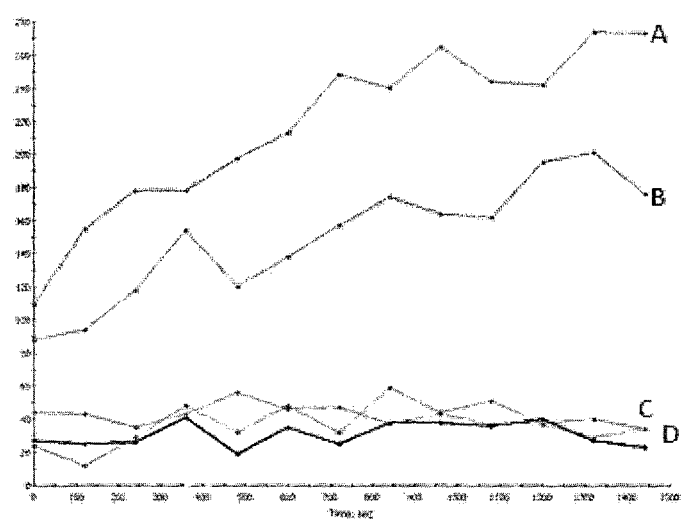
FIG. 13 shows the time course measurement of 10 uM (top) or 100 uM (bottom) of a pyrene-based rotor with 5 ug plasmid DNA under various conditions, (A) DNA only (B) DNA+40 mM NaOH (C) DNA+120 mM (D) DNA+200 mM NaOH (E) rotor in buffer only (black trace).
Figure 13:
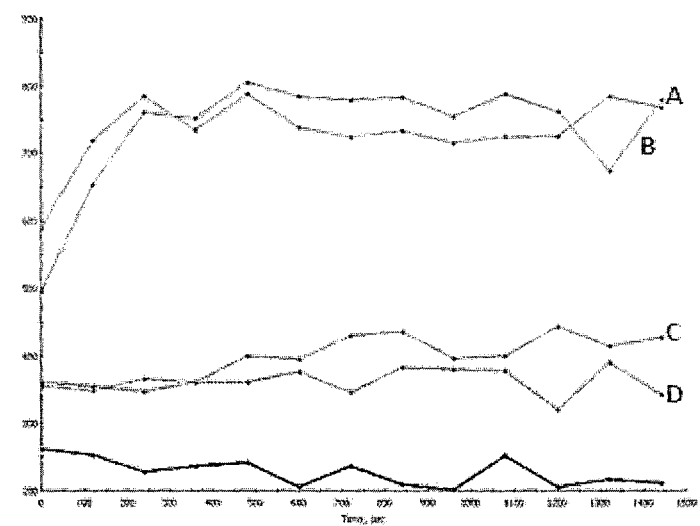
Figure 14:
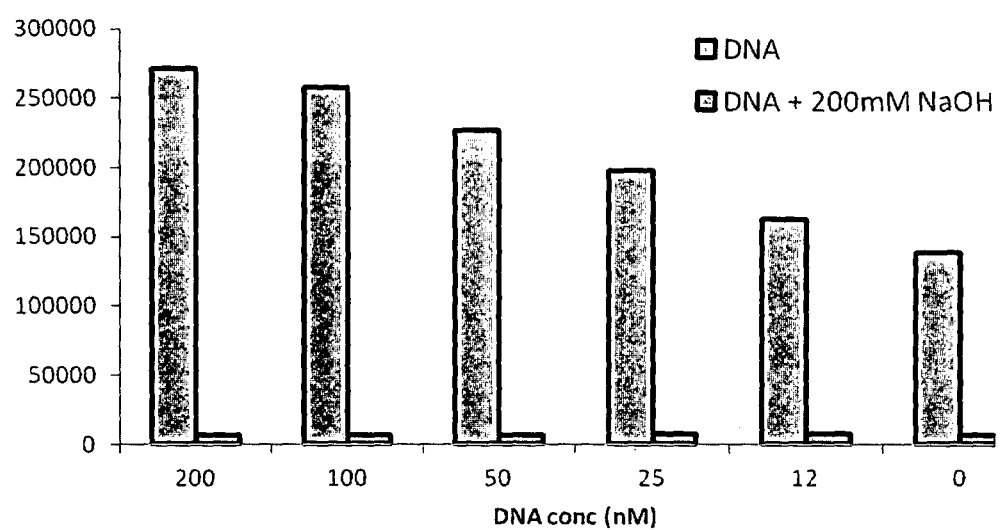
FIG. 14 shows the fluorescence of acrydine-based rotor with DNA and with or without NaOH. Measurements at 480/520 using 50 uM Acrydine with increasing concentration of a 450 bp DNA fragment (PetF and R). Red bars show fluorescence after addition of NaOH to reaction mix.

The behavior of rotors when incubated with DNA was also examined (FIG. 12).

Figure 15:
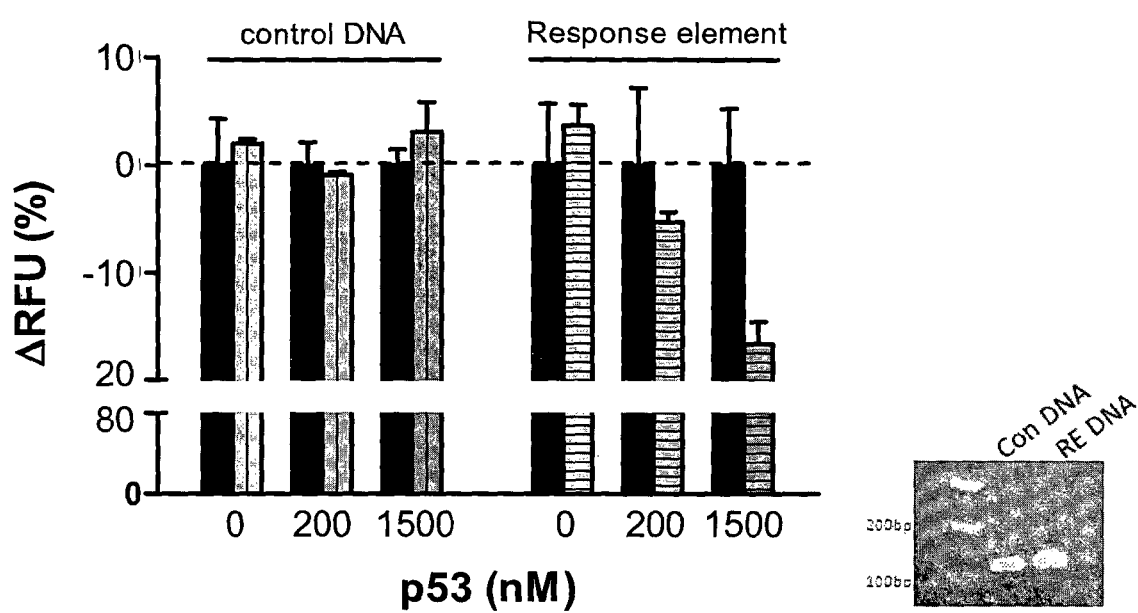
FIG. 15 shows a fluorescent molecular rotor displacement assay. Reference readings for reaction mixes consisting of 50 uM Acrydine with 150 nM of either control or response element DNA was first taken in the absence of p53 protein. p53 protein was then added at varying concentrations (0, 200 or 500 nM) and incubated at r.t. for 60 minutes before a second measurement was taken. Data is presented as percentage change in fluorescence after the addition of p53 protein (Grey and blue bars) normalized to respective reference measurements (100%, Black bars). Inset shows relative sizes of control- and 5xRE-DNA at 125 and 130 bp, respectively. Error bar shows S.D. of 2 separate binding reactions. Red hashed-line indicates reference signal before p53 addition at 100%. 30 uL reaction sample contains 5 uL DNA or buffer blank (75 ng/uL in 10 mM Tris pH 8.0), 4 uL of p53 protein or buffer blank (23 uM in 100 mM Tris pH8.0, 7 mM DTT, 20 mM NaCl) in p53 binding buffer (25 mM phosphate pH7.2, 150 mM KCl, 4 mM DTT).

Whether the binding of a protein (p53) to DNA (with rotor bound) resulting in any fluorescence change due to displacement of the rotor by the protein was also examined. P53 protein was added to either control DNA (not containing a p53 binding motif) or DNA containing the p21 response element which p53 is known to bind. The data indicates that p53 binding to p21 can result in displacement of the rotor with concomitant reduction in fluorescence (FIG. 15).

Whether biotin modification would affect binding to DNA was examined. It was also examined whether the addition of biotin would make rotors useful for affinity purification of DNA. Biotinylated versions of the rotors were incubated with DNA and complexes captured on streptavidin plates. Captured DNA was then quantified by real-time PCR. The results in FIG. 16 indicate that these rotors can be used as reagent for affinity purification of DNA. The fluorescent properties of the biotinylated rotor changed upon binding to streptavidin (FIG. 6), presumably due to steric constraints imposed upon binding of the biotin.

Example 11: Binding of Rotor-Peptide with Protein

Synthesis of Rotor-Peptide Probes, JP1-R and JP2-R

Figure 25A:
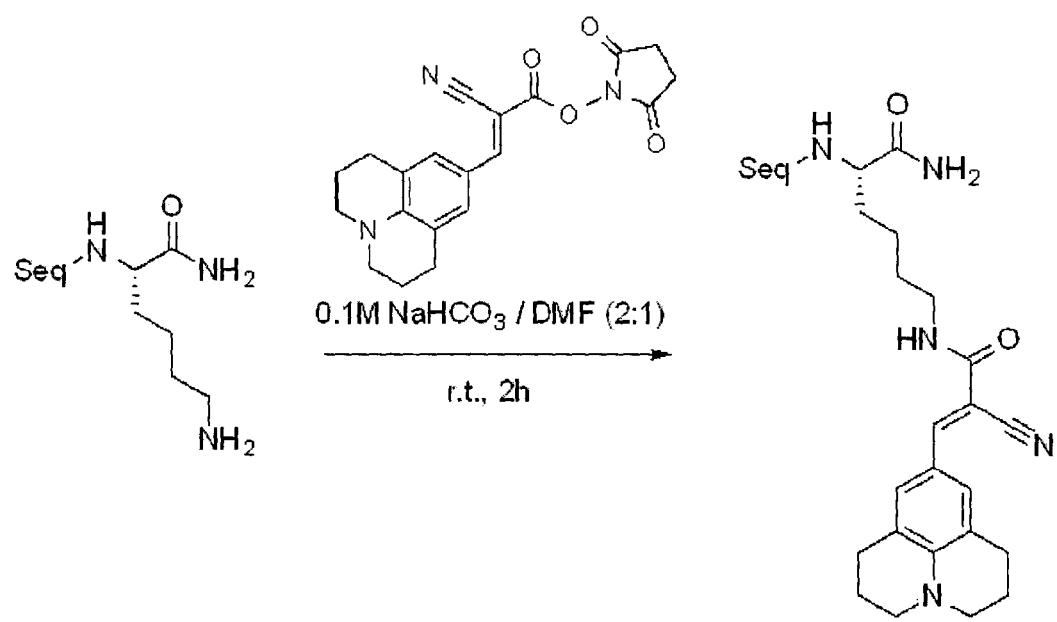
FIG. 25a shows a synthetic scheme for rotor-peptide conjugates.

A julodine-based rotor, CCVJ, was conjugated to two peptides derived from a phage display screen, JP1 and JP2, which differ by only a single amino acid but have a fold difference in binding affinities (Table 9). An additional lysine residue was added to the C-termini of both peptide sequences, then reacted with the N-hydroxysuccinimidyl-activated ester of CCVJ to make the rotor-peptide probes (FIG. 25a).

Unmodified peptides JP1 and JP2 were synthesized by Genscript USA Inc. Chemicals and solvents were purchased from Sigma Aldrich and TCI Chemicals Japan.

JP1 (2 mg) was weighed into a 1.5 mL vial and dissolved in 0.3 mL of 0.1M NaHCO$_3$ buffer. NHS-protected CCVJ (4 equiv.) was also weighed into another 1.5 mL vial and dissolved in 0.1 mL dry DMF, before being added to the JP1 that was dissolved in buffer. The reaction mixture was allowed to stir at room temperature for 2 hours before HPLC purification to obtain the pure rotor-peptide, JP1-R (9%). MALDI-TOF MS [M]+ Calculated 1949.8957. Obtained 1946.6082.

JP2 (2 mg) was weighed into a 1.5 mL vial and dissolved in 0.3 mL of 0.1M NaHCO$_3$ buffer. NHS-protected CCVJ (4 equiv.) was also weighed into another 1.5 mL vial and dissolved in 0.1 mL dry DMF, before being added to the JP2 that was dissolved in buffer. The reaction mixture was allowed to stir at room temperature for 2 hours before HPLC purification to obtain the pure rotor-peptide, JP2-R (4%). MALDI-TOF MS [M+K]$^+$ Calculated 2015.8703. Obtained 2017.6360.

JP2 (2 mg) was weighed into a 1.5 mL vial and dissolved in 0.3 mL of 0.1M NaHCO$_3$ buffer. NHS-protected CCVJ rotor (4 equiv.) was also weighed into another 1.5 mL vial and dissolved in 0.1 mL dry DMF, before being added to the JP2 that was dissolved in buffer. The reaction mixture was allowed to stir at room temperature for 2 hours before HPLC purification to obtain the pure rotor-peptide, JP2-R (4%). MALDI-TOF MS [M+K]$^+$ Calculated 2015.8703. Obtained 2017.6360.

Figure 25B:
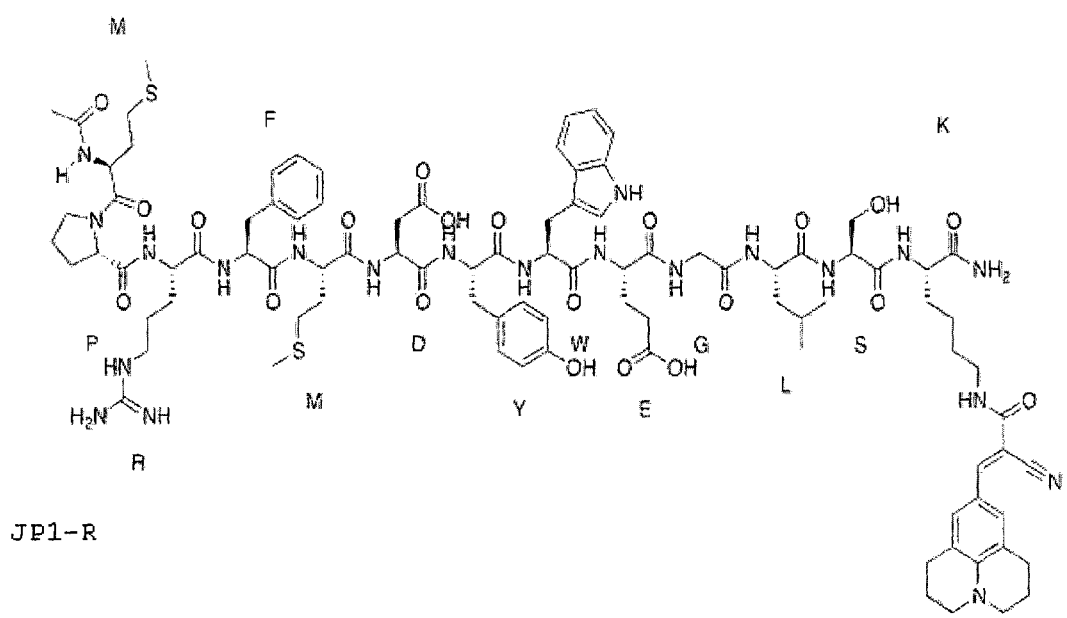
FIG. 25b depicts the structure of CCVJ rotor conjugated with JP1 peptide (JP1-R) (SEQ ID NO:1).
Figure 25C:
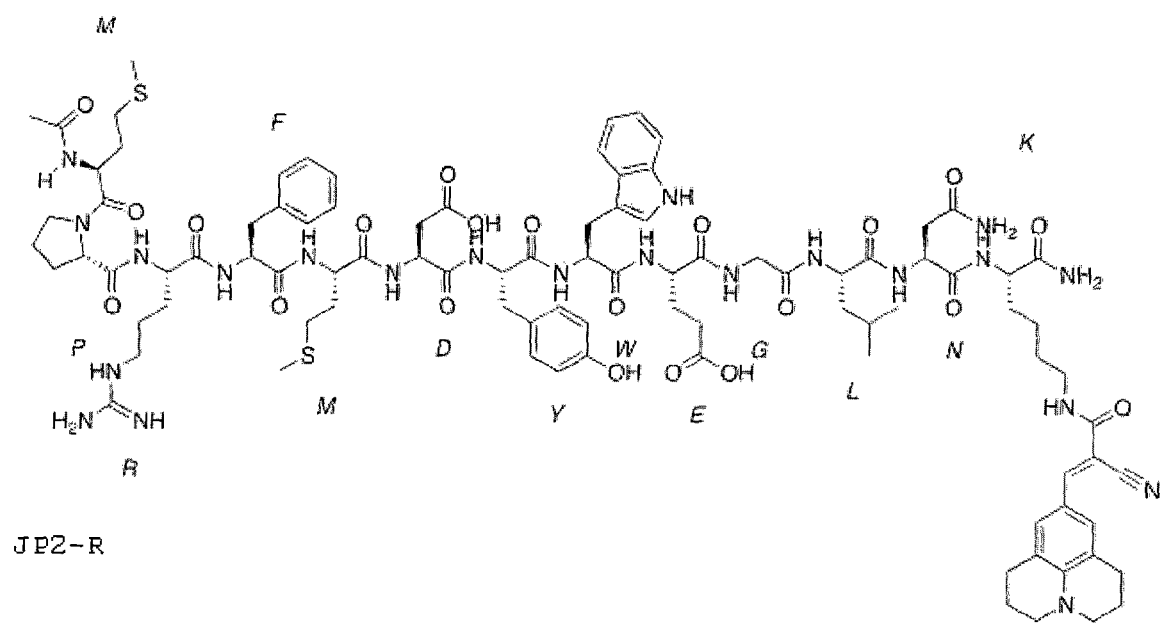
FIG. 25c depicts the structure of CCVJ rotor conjugated with JP2 peptide (JP2-R) (SEQ ID NO:2).

Rotor-peptide probes, JP1-R and JP2-R, are shown in FIGS. 25b and 25c.

Binding of Rotor-Peptide Conjugates to a Protein

Figure 20A:
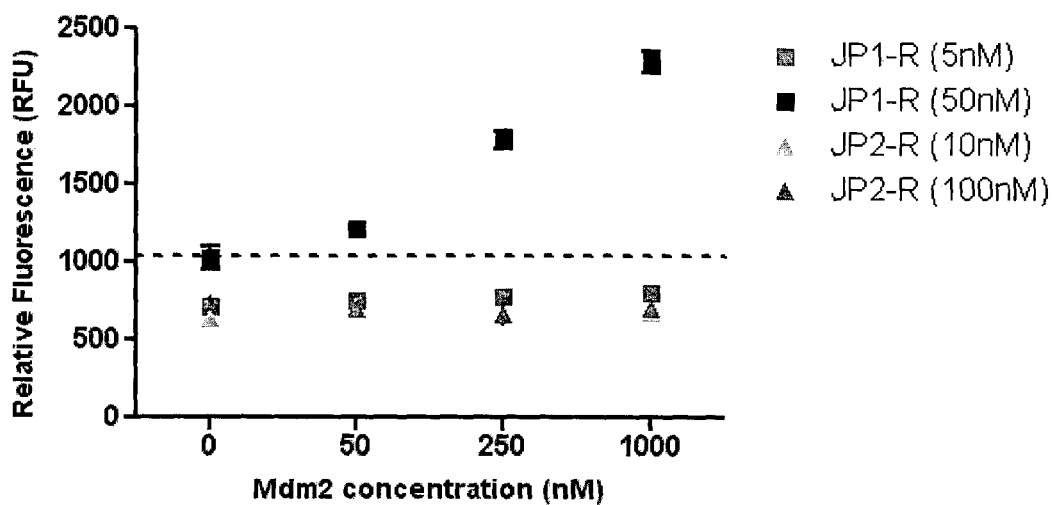
FIG. 20a shows that the fluorescence of JP1-R increases when bound specifically to recombinant Mdm2 (residues 18-125) (Top) Rotor-peptide conjugates, JP1-R and JP2-R were added individually to indicated concentrations of Mdm2. (Bot) Fluorescence from binding between Mdm2 and JP1-R was ablated with the addition of Nutlin (50 µM). Black hashed-line shows the background fluorescence from 50 nM JP1-R only. Error shows average±S.D. (n=2). (C) JP1-R (50 nM) was added to increasing amounts of Mdm2 (residues 18-125), eiF4e, BSA and IgG. Black hashed-line shows background fluorescence from JP1-R only (50 nM). Error shows average±S.D. (n=2)
Figure 20A:
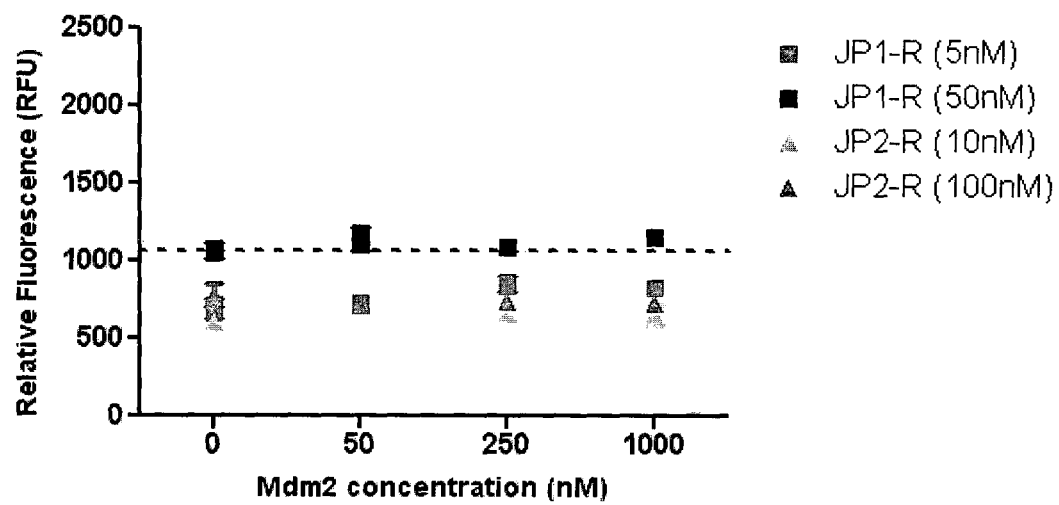

Affinity purified recombinant MDM2 protein (residues 18-125) was used to test the functionality of the rotor-peptide conjugates. Co-incubation of JP1-rotor conjugate, JP1-R, with MDM2 protein, led to a concentration dependent increase in fluorescence activity (FIG. 20a (top)).

Nutlin-3, an MDM2 agonist, binds MDM2 at the N-terminal hydrophobic cleft and abrogates this interaction by occluding p53-MDM2. Addition of 50 uM of Nutlin to the JP1-R-MDM2 complex MDM2 completely abrogated the florescence signal seen before (FIG. 20a, Bottom), presumably due to the displacement of JP1 from MDM2. JP2-R did not display any significant changes in fluorescence intensity upon adding MDM2. This lack of signal May be ascribed to the non-constrained orientation of the rotor upon binding of the peptide to MDM2.

Figure 20B:
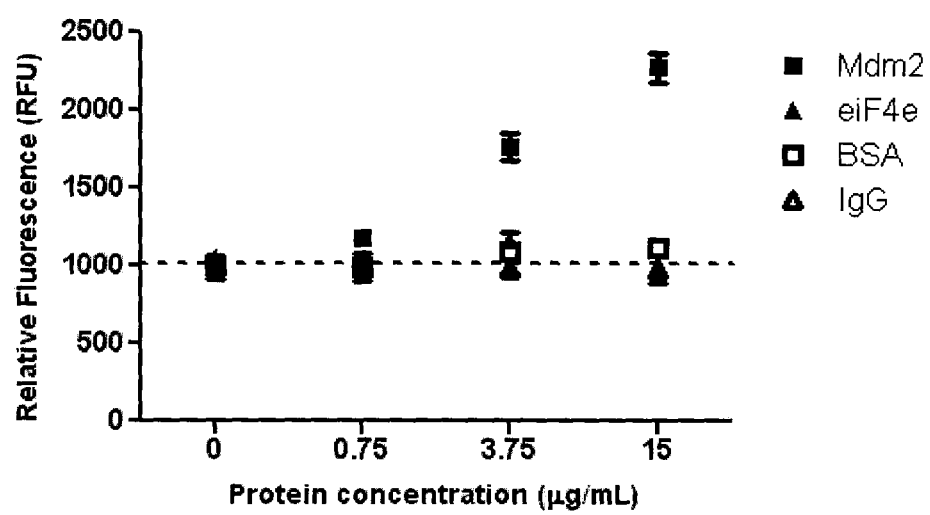
FIG. 20b shows that the fluorescence of JP1-R increases when bound specifically to recombinant Mdm2 (residues 18-125) JP1-R (50 nM) was added to increasing amounts of Mdm2 (residues 18-125), eiF4e, BSA and IgG. Black hashed-line shows background fluorescence from JP1-R only (50 nM). Error shows average±S.D. (n=2).

To further demonstrate that fluorescence activation was due to a concomitant steric restriction of the appended rotor during protein-specific interaction, JP1-R was added to non-specific proteins, eIF4E, BSA and IgG. No fluorescence increase was observed with all 3 proteins across the same concentrations range (FIG. 20b).

Based on the JP1-R fluorescence measurements, an apparent $K_d$ of 16.01±7.52 nM for MDM2 binding was calculated (FIG. 21a), correlating well to a previously reported value of 18.83±5.03 nM (Table 9) determined using ITC. The calculated apparent $K_d$ of JP2-R, was 3365±640.6 nM, approximately 14-fold lower than the previously reported value of 239.81±53.79 nM.

Figure 27:
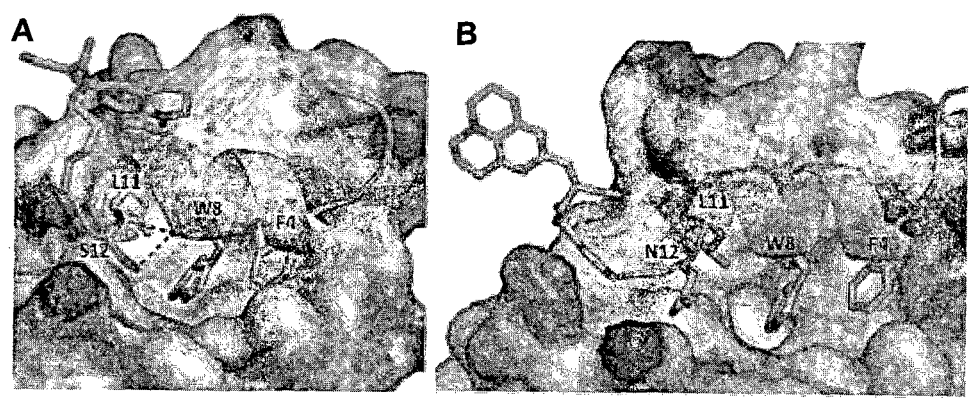
FIG. 27 shows the in-silico model of rotor-peptide conjugates, (A) JP1-R and (B) JP2-R bound to MDM2 pocket. Hydrogen bond interactions of W8 backbone with S12 backbone and side chain are shown in red-dashed lines. Rotor moiety depicted in green.

To further understand the fluorescence-derived apparent dissociation constants of JP1-R and JP2-R, an in-silico modeling of their respective interactions with the MDM2 protein was performed. Molecular dynamics simulations suggest that the C-terminal end of JP1-R adopts a helical turn due to the constraints from the hydrogen bonds between the hydroxyl sidechain and backbone of S12 and the backbone carbonyl of W8. A similar feature was also seen in prior experimental and computational studies for a similar peptide. The replacement of S12 by N12 in JP2-R does not afford this constraint. The Asn sidechain is longer and is unable to form hydrogen bonds with the backbone, resulting in an extended C-terminus (FIG. 27). Replica exchange simulations exploring the conformational space of the unbound rotor-peptides (Table 4) show that JP1-R is more helical than JP2-R. The constrained JP1-R (FIG. 27) also embeds deeper into MDM2 and interacts stronger than JP2-R (by ~7kT, Table 5). The major contribution arises from improved packing of S12 (by 1.2kT, Tables 6, 7), L11 (embeds deeper into MDM2 by ~2kT) and the rotor (~2kT). The rotor packs between H96 of MDM2 and the peptide in JP1-R while JP2-R packs into a recently characterized second binding site in MDM2. This tighter association of JP1-R restricts the rotational freedom of the rotor sufficiently to bring about a detectable fluorescence turn-on signal.

Example 12: Drug Screening Applications

Figure 11:
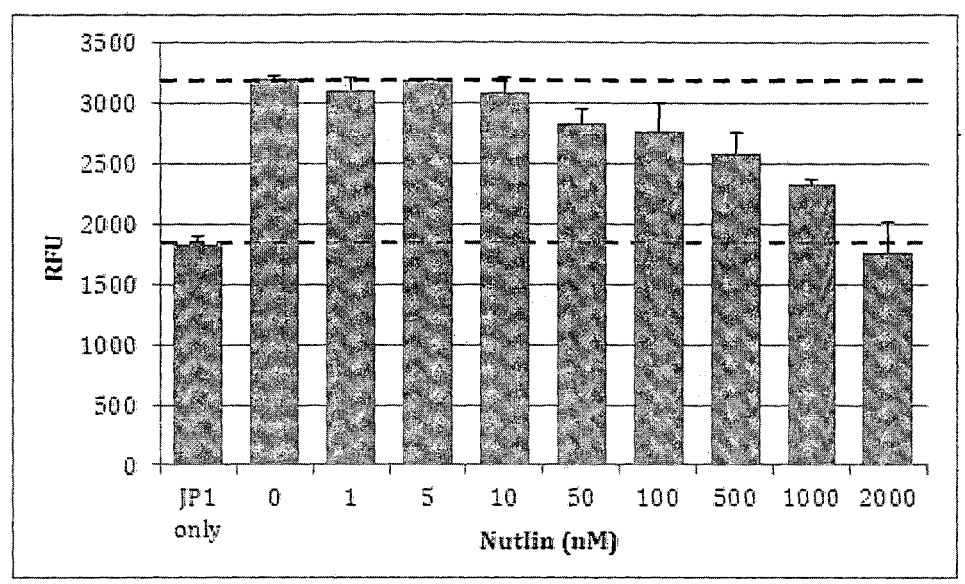
FIG. 11 shows that nutlin dependent inhibition of binding between MDM2 (500 nM) and JP1 (250 nM) results in a concentration dependent decrease in fluorescence activity. Error shows S.D. +/− triplicate readings from duplicate binding reactions. Black and red hashed lines denote maximum fluorescence and background fluorescence from rotor-peptide conjugate, respectively.

Rotor-peptide may have potential use in drug-screening applications. Small molecule inhibitor nutlin was titrated and a disruption of the rotor-peptide-MDM2 complex at concentrations as low as 10 nM was observed (FIG. 11). The results indicate highly sensitive detection of nutlin binding to MDM2, suggesting the rotor-peptide assay may have use in primary drug screens for disruption of a peptide-protein interaction.

Rotor-Peptide Conjugate as a Biosensor for Small Molecules that Inhibit p53-MDM2 Interaction A concentration-dependent drop in fluorescence was seen when nutlin was titred into a pre-incubated mix containing 500 nM of MDM2 and 250 nM of JP1 (FIG. 11). Complete ablation of JP1-MDM2 dependent fluorescence was observed at 2 uM of Nutlin treatment, but a significant decrease can be seen at 50 nM. The sensitivity and specificity of such peptide-rotor conjugates make them ideal for development into screening platforms for identifying molecules that inhibit p53-MDM2 binding.

Application of Rotor-Peptide in Small Molecule Drug Screening (E.G. Inhibitors of MDM2)

Figure 21:
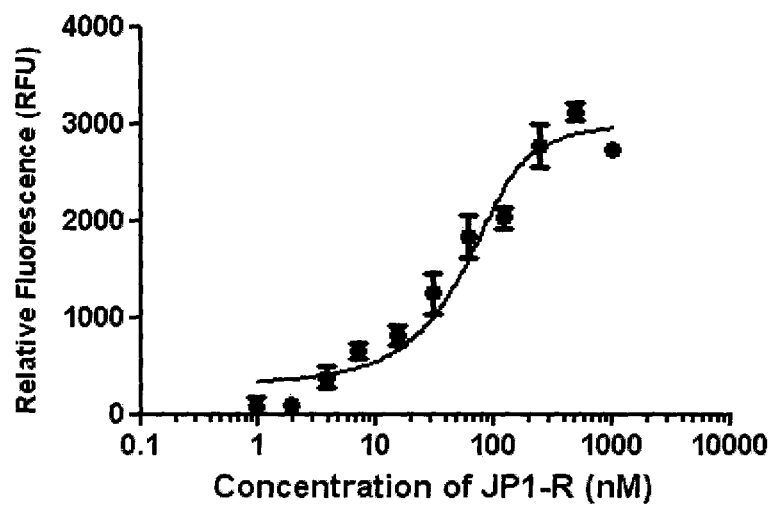
FIG. 21 shows the non-linear fit and calculated apparent $K_d$s of rotor-peptide conjugates to Mdm2. Fluorescence measurements were taken by titrating either JP1-R (top) or JP2-R (bottom), across a concentration range into solutions containing 100 nM of Mdm2 (18-125). Apparent $K_d$ was calculated using a 1:1 non-linear binding fit model described above. Calculated apparent $K_d$ of Mdm2 to JP1-R or JP2-R, was 16.01±7.52 nM and 3365±640.6 nM, respectively.
Figure 21:
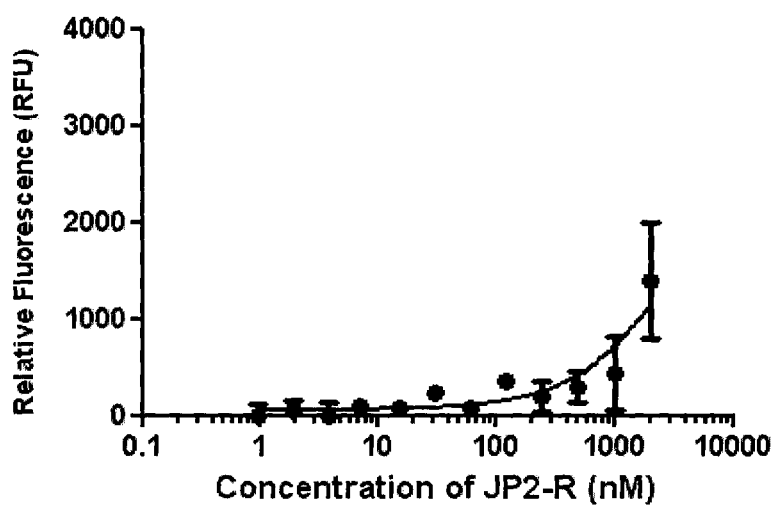
Figure 22:
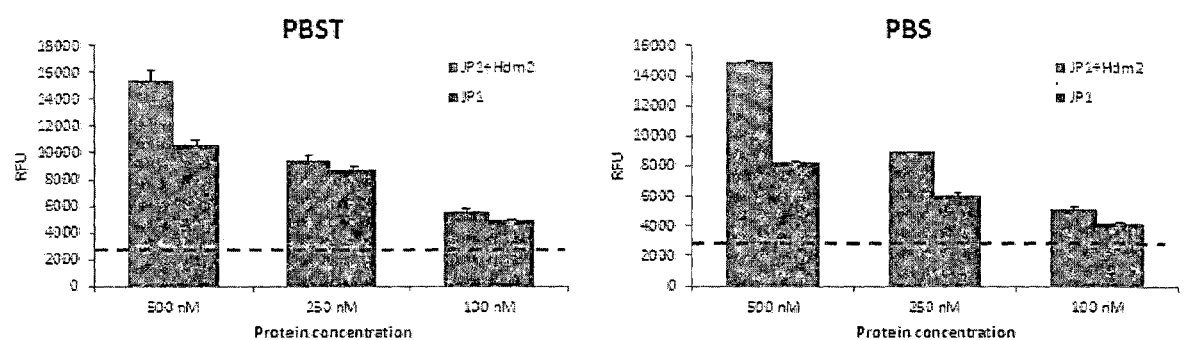
FIG. 22 shows an increase in non-specific background fluorescence (JP1-R only) when 0.1% Tween-20 detergent (typical concentration used) was added to PBS binding buffer. However because Tween was needed to give a more consistent measurement, it was subsequently used at 0.005%.
Figure 23:
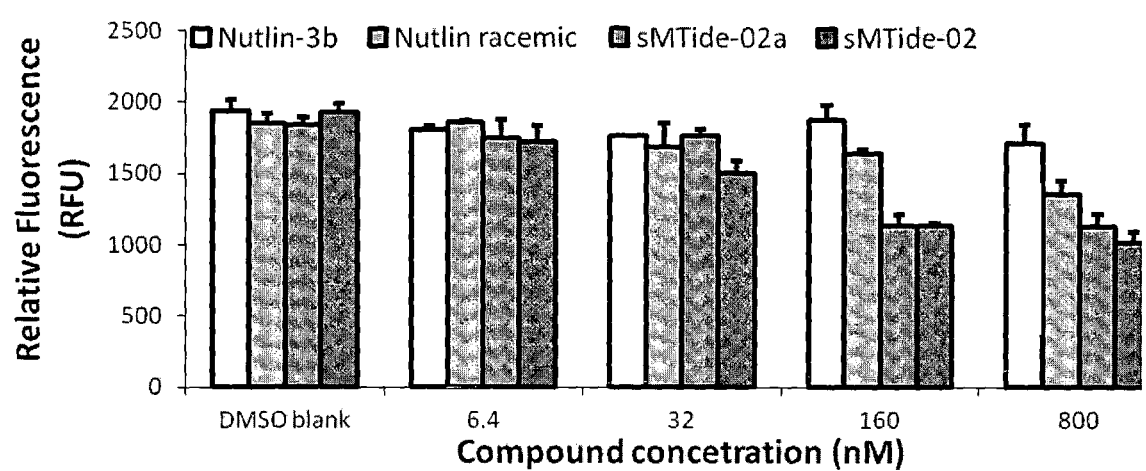
FIG. 23 shows that JP1-R is sensitive to known inhibitors of Mdm2-p53 interaction, as shown in displacement assay using inhibitors. Four different inhibitors of p53-Mdm2: Nutlin-3b ($K_d$~1.5 µM), Nutlin racemic ($K_d$=201.6±61 nM), sMTide-02 ($K_d$=34.4±2 nM) and sMTide-02a ($K_d$=6.76±2 nM), were added to reaction mixtures containing 200 nM of Mdm2 and 80 nM of JP1-R, at concentrations up to 800 nM. Values indicate average±S.D. (n=3).

The inhibition of p53-MDM2 interaction is a common strategy for cancer treatment. A rotor is attached to the JP1 peptide (a sequence that binds the MDM2 protein at the same site as p53) to investigate if the JP1 peptide-rotor conjugate will act as a reporter for compounds that displace it from MDM2. FIG. 23 shows that such a displacement can be seen when various known p53-MDM2 inhibitors are added to the JP1/MDM2 complex. Calculated $K_d$ from MDM2 against JP1 titration indicates that rotor-moeity does not obstruct peptide-protein interaction (FIG. 21a).

To demonstrate the utility of the rotor-peptide probe in small molecule drug screening, the sensitivity of the rotor-peptide to known small molecule and stapled-peptide inhibitors of the p53-MDM2 interaction was explored. These inhibitors target the same hydrophobic cleft in MDM2 as JP1-R, and were able to disrupt the MDM2-probe complex in the expected manner, resulting in a decrease in fluorescence as the probe was displaced (FIG. 24 and Table 8).

Figure 26A:
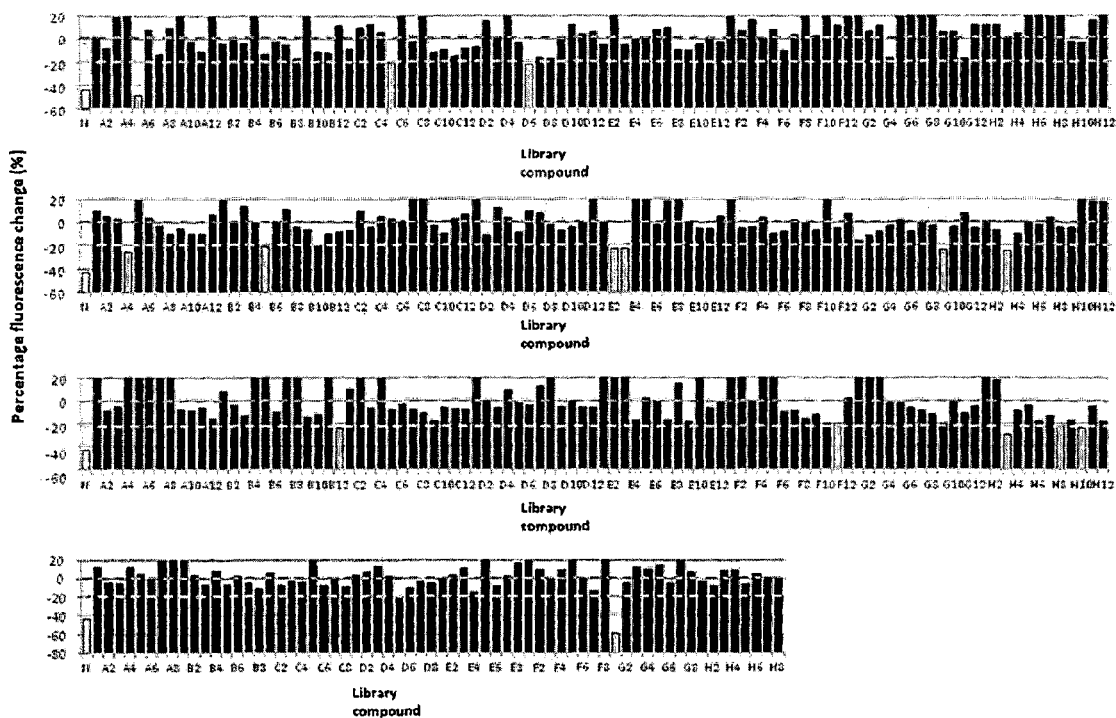
FIG. 26a shows a fragment library screen and lead validation for p53-MDM2 inhibition.
Figure 26B:
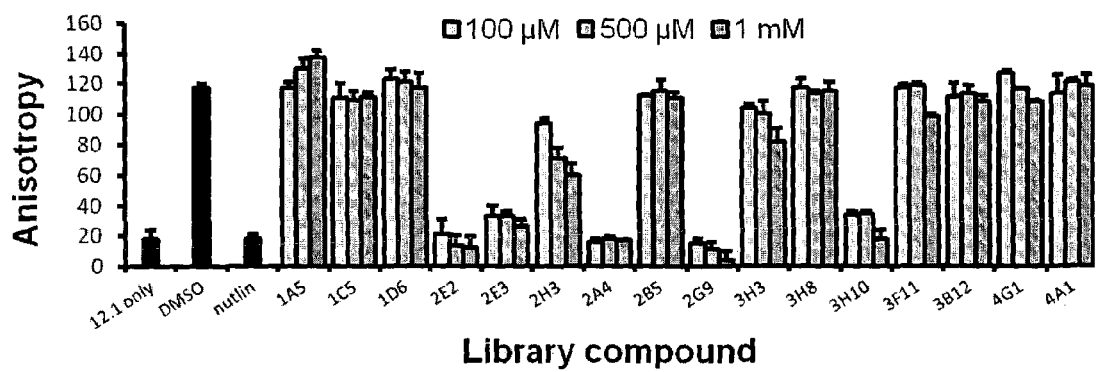
FIG. 26b shows that ten out of fifteen hits were validated by fluorescence polarization assay, showing ligand-dependent (100 µM, 500 µM or 1 mM) displacement. Black bars depict control measurements of FAM-labeled 12.1 peptide, DMSO negative control and 1 µM Nutlin positive control. Inactive compound 4A1, used at same concentrations, shows negative displacement control. Error shows S.D. of triplicate measurements.
Figure 26C:
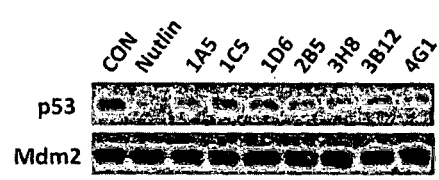
FIG. 26c shows that weaker inhibitor fragments were further assessed through their ability to displace in vitro translated full-length p53 protein bound to recombinant Mdm2-immobilised on cobalt beads. Western blot shows levels of p53 (upper panel) captured in the presence of indicated compounds (500 uM). Control lanes 1 and 2-show negative control (inactive 4A1 fragment) and positive (100 µM Nutlin) displacement events, respectively. Lower panel indicates input Mdm2 levels eluted off beads.
Figure 26D:
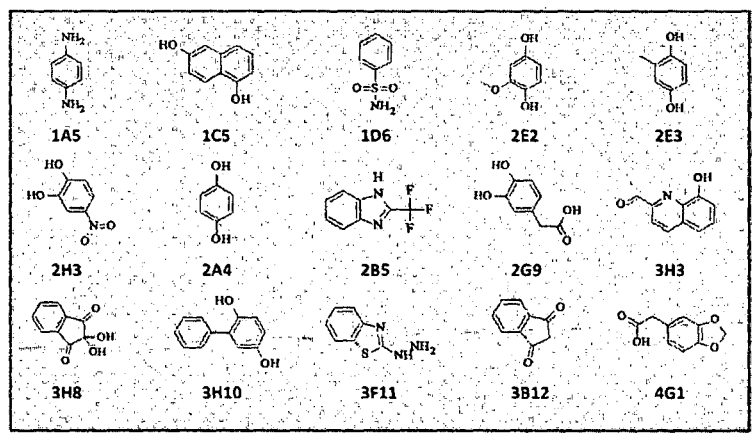
FIG. 26d shows the chemical structures of positive lead compounds.

Given the high sensitivity and specificity of the JP1-R conjugate, it was used to screen a small molecule fragment library (n=352) for candidates that potentially disrupt p53-MDM2 binding. Based on the results, fifteen hits were selected for further validation and ten compounds were further confirmed as genuine inhibitors (FIG. 26b). The seven disparate compounds showing no activity in the FP assay were therefore assessed in a pull-down assay which measured the direct interaction levels of p53 and MDM2. All seven compounds inhibited p53-MDM2 interaction, further validating these as genuine hits not identified by the FP assay (FIG. 26c). As subtle intermolecular twisting of the rotor profoundly effects signal generation, it is possible that partial displacement of the peptide by the weak inhibitors led to their identification. In the FP assay, these would have been missed, as the anisotropy measurement is largely attendant on full displacement of peptide from MDM2.

Together, these results demonstrate the utility of molecular rotors in binding assays for detecting peptide-protein interactions and for drug screening applications. Using the TICT property of the molecular rotor, its free volume is decreased upon binding interaction to a protein. This simple fluorescence turn-on signal upon protein binding allows the development of highly sensitive and facile assays to measure protein-ligand binding in a high-throughput fashion. More importantly, it is shown that a molecular rotor-based screening assay identified validated hits that were missed by fluorescence polarization assay in a fragment-based screen, suggesting its utility in identifying lower affinity hits in fragment based screening.

APPLICATIONS

The disclosed fluorescent molecular rotors may be used to detect protein-ligand interactions, such as protein-DNA, protein-peptide and protein-small molecule interactions, for example, to investigate the interaction of p53 protein with DNA, interaction of MDM2 with peptides. The disclosed fluorescent molecular rotors may also be conjugated to biotin to give a streptavidin detection reagent.

The disclosed fluorescent molecular rotors may be used as viscosity probes, displaying an increase in fluorescence when viscosity of the solution is increased.

The disclosed fluorescent molecular rotors may be used in drug screening applications. The disclosed fluorescent molecular rotors may be used to screen for active compounds that bind to a target protein, for example, inhibitors of MDM2.

The disclosed screening applications may not require the use of expensive instrumentation. Thus, the disclosed screening applications may serve as a cost-effective means for drug screening.

The disclosed screening applications may be single-well, low volume with minimal pipetting steps and may not require multiple washing steps. Thus, the disclosed screening applications may be non-laborious and optimal for high-throughput screening.

The disclosed screening applications may not require the use of radioisotopes for labelling. Thus, the disclosed screening applications may be non-radioactive.

The disclosed screening applications may be used in small molecule drug screening and may be used to identify small molecules which may be missed in traditional assays, such as fluorescence polarization.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:
1. A chemical compound of formula (i):

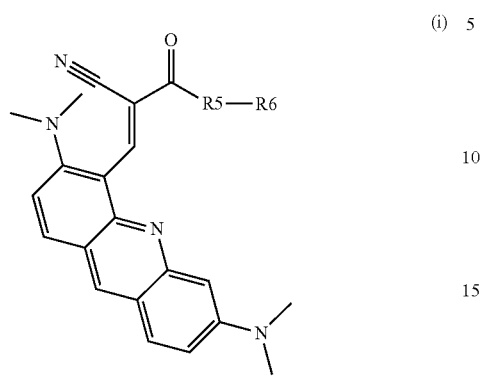

wherein R5 is a OH or a linking moiety selected from the group consisting of a single bond; or optionally substituted heteroalkyl, wherein the main chain atoms of said optionally substituted heteroalkyl are optionally interrupted by one or more optionally substituted cyclic groups; wherein R6 is absent or a ligand, and when R5 is OH, R6 is absent.

* * * * *